US012673088B2

(12) United States Patent
Triebel et al.

(10) Patent No.: US 12,673,088 B2
(45) **Date of Patent: *Jul. 7, 2026**

(54) COMBINED PREPARATIONS FOR THE TREATMENT OF CANCER OR INFECTION

(71) Applicant: IMMUTEP S.A.S., Orsay (FR)

(72) Inventors: Frederic Triebel, Versailles (FR); Chrystelle Brignone, Chatenay-Malabry (FR)

(73) Assignee: IMMUTEP S.A.S., Orsay (FR)

( * ) Notice: Subject to any disclaimer, the term of this patent is extended or adjusted under 35 U.S.C. 154(b) by 733 days.

This patent is subject to a terminal disclaimer.

(21) Appl. No.: 17/929,888

(22) Filed: Sep. 6, 2022

(65) Prior Publication Data

US 2023/0074746 A1 Mar. 9, 2023

Related U.S. Application Data

(60) Continuation of application No. 17/072,612, filed on Oct. 16, 2020, now Pat. No. 11,684,654, which is a division of application No. 15/542,466, filed as application No. PCT/EP2016/050321 on Jan. 8, 2016, now Pat. No. 10,874,713.

(30) Foreign Application Priority Data

Jan. 9, 2015 (GB) ..................................... 1500374

(51) Int. Cl.

| | |
|---|---|
| ***A61K 39/00*** | (2006.01) |
| ***A61K 38/17*** | (2006.01) |
| ***A61K 39/395*** | (2006.01) |
| ***A61P 31/16*** | (2006.01) |
| ***A61P 31/22*** | (2006.01) |
| ***A61P 35/04*** | (2006.01) |
| ***C07K 16/28*** | (2006.01) |

(52) U.S. Cl.

CPC ........ *A61K 38/1774* (2013.01); *A61K 38/177* (2013.01); *A61K 39/3955* (2013.01); *A61P 31/16* (2018.01); *A61P 31/22* (2018.01); *A61P 35/04* (2018.01); *C07K 16/2818* (2013.01); *A61K 39/39558* (2013.01); *A61K 2300/00* (2013.01); *C07K 2317/70* (2013.01); *C07K 2317/76* (2013.01); *C07K 2319/30* (2013.01); *C07K 2319/32* (2013.01); *Y02A 50/30* (2018.01)

(58) Field of Classification Search

CPC .............. A61K 38/1774; A61K 38/177; A61K 39/39558; A61K 2300/00; A61P 35/04; C07K 2317/70; C07K 2317/76

See application file for complete search history.

(56) References Cited

U.S. PATENT DOCUMENTS

| | | | |
|---|---|---|---|
| 5,078,996 | A | 1/1992 | Conlon, III et al. |
| 5,098,702 | A | 3/1992 | Zimmerman et al. |
| 5,225,348 | A | 7/1993 | Nagata et al. |
| 5,266,491 | A | 11/1993 | Nagata et al. |
| 5,436,146 | A | 7/1995 | Shenk et al. |
| 5,539,084 | A | 7/1996 | Geysen |
| 5,637,483 | A | 6/1997 | Dranoff et al. |
| 5,665,577 | A | 9/1997 | Sodroski et al. |
| 5,700,907 | A | 12/1997 | Hercend et al. |
| 5,753,500 | A | 5/1998 | Shenk et al. |
| 5,773,578 | A | 6/1998 | Hercend et al. |
| 5,785,973 | A | 7/1998 | Bixler et al. |
| 5,798,231 | A | 8/1998 | Hercend et al. |
| 5,817,511 | A | 10/1998 | Hercend et al. |
| 5,830,758 | A | 11/1998 | Hercend et al. |
| 5,840,839 | A | 11/1998 | Wang et al. |
| 5,872,005 | A | 2/1999 | Wang et al. |
| 5,874,250 | A | 2/1999 | Hercend et al. |
| 5,904,920 | A | 5/1999 | Dranoff et al. |
| 5,955,300 | A | 9/1999 | Faure et al. |
| 5,955,331 | A | 9/1999 | Danos et al. |
| 5,976,877 | A | 11/1999 | Hercend et al. |
| 5,981,276 | A | 11/1999 | Sodroski et al. |
| 5,985,290 | A | 11/1999 | Jaffee et al. |
| 6,033,674 | A | 3/2000 | Jaffee et al. |
| 6,037,177 | A | 3/2000 | Snyder |

(Continued)

FOREIGN PATENT DOCUMENTS

| | | | |
|---|---|---|---|
| CA | 2 391 927 | A1 | 5/2001 |
| CN | 101873864 | A | 10/2010 |

(Continued)

OTHER PUBLICATIONS

Guo, Z.S. et al., "Evaluation of Promoter Strength for Hepatic Gene Expression In Vivo Following Adenovirus-Mediated Gene Transfer", Gene Therapy 3(9):802-810 (1996).

Harvey, R.D., "Immunologic and Clinical Effects of Targeting PD-1 in Lung Cancer", Clinical Pharmacology & Therapeutics 96(2):214-223 (Aug. 2014).

Hatam, L.J. et al., "Immune Suppression in Premalignant Respiratory Papillomas: Enriched CD-1+Foxp3+ Regulatory T Cells and PD-1/PD-LI/L2 Expression", Clinical Cancer Research 18(7):1925-1935 (2012).

(Continued)

*Primary Examiner* — Lei Yao

(74) *Attorney, Agent, or Firm* — Scully, Scott, Murphy & Presser, P.C.

(57) ABSTRACT

Combined preparations, and pharmaceutical compositions, comprising: (a) LAG-3 protein, or a derivative thereof that is able to bind to MHC class II molecules; and (b) a programmed cell death protein-1 (PD-1) pathway inhibitor, are described. The PD-1 pathway inhibitor, such as an anti-PD-1 antibody or an anti-PD-L1 antibody, and a soluble derivative of LAG-3, acting as an APC activator, together synergistically activate T cells (in particular, $CD8^+$ T cells). Use of the combined preparations and compositions as medicaments, in particular for the treatment of cancer or infection, and to methods for the treatment of cancer or infection, is described.

15 Claims, 25 Drawing Sheets

Specification includes a Sequence Listing.

(56) References Cited

U.S. PATENT DOCUMENTS

| | | | |
|---|---|---|---|
| 6,040,183 | A | 3/2000 | Ferrari et al. |
| 6,093,570 | A | 7/2000 | Ferrari et al. |
| 6,114,516 | A | 9/2000 | Hercend et al. |
| 6,143,273 | A | 11/2000 | Faure et al. |
| 6,277,368 | B1 | 8/2001 | Hiserodt et al. |
| 6,350,445 | B1 | 2/2002 | Jaffee et al. |
| 6,410,509 | B1 | 6/2002 | Triebel et al. |
| 6,428,953 | B1 | 8/2002 | Naldini et al. |
| 6,464,973 | B1 | 10/2002 | Levitsky et al. |
| 6,482,925 | B1 | 11/2002 | El Tayar et al. |
| 6,506,604 | B2 | 1/2003 | Finer et al. |
| 6,596,536 | B1 | 7/2003 | Hercend et al. |
| RE38,313 | E | 11/2003 | Faure et al. |
| 6,855,802 | B1 | 2/2005 | Triebel et al. |
| 6,875,844 | B1 | 4/2005 | Ronsin et al. |
| 7,109,026 | B2 | 9/2006 | Triebel et al. |
| 7,294,712 | B2 | 11/2007 | Hercend et al. |
| 8,425,897 | B2 | 4/2013 | Jooss et al. |
| 9,220,776 | B2 | 12/2015 | Sharma et al. |
| 9,579,382 | B2 | 2/2017 | Triebel |
| 10,232,038 | B2 | 3/2019 | Triebel |
| 10,736,940 | B2 | 8/2020 | Triebel |
| 10,874,713 | B2 | 12/2020 | Triebel et al. |
| 10,940,181 | B2 | 3/2021 | Triebel et al. |
| 11,583,582 | B2 | 2/2023 | Triebel |
| 11,684,654 | B2 | 6/2023 | Triebel et al. |
| 12,214,012 | B2 | 2/2025 | Triebel |
| 2002/0192195 | A1 | 12/2002 | Triebel et al. |
| 2003/0087319 | A1 | 5/2003 | Gomes et al. |
| 2004/0081686 | A1 | 4/2004 | Kravtzoff et al. |
| 2004/0171551 | A1 | 9/2004 | Triebel et al. |
| 2004/0197312 | A1 | 10/2004 | Moskalenko et al. |
| 2006/0110755 | A1 | 5/2006 | Duke et al. |
| 2006/0127482 | A1 | 6/2006 | Fewell et al. |
| 2007/0231298 | A1 | 10/2007 | Li et al. |
| 2008/0003235 | A1 | 1/2008 | Triebel |
| 2008/0069770 | A1 | 3/2008 | Hercend et al. |
| 2009/0130054 | A1 | 5/2009 | Jooss et al. |
| 2011/0008331 | A1 | 1/2011 | Triebel |
| 2011/0150892 | A1 | 6/2011 | Thudium et al. |
| 2011/0318373 | A1 | 12/2011 | Sasikumar et al. |
| 2013/0109843 | A1 | 5/2013 | Carven et al. |
| 2013/0309250 | A1 | 11/2013 | Cogswell et al. |
| 2014/0341920 | A1 | 11/2014 | Noelle |
| 2016/0310570 | A1 | 10/2016 | Triebel |
| 2017/0119876 | A1 | 5/2017 | Triebel |
| 2018/0271940 | A1 | 9/2018 | Triebel et al. |
| 2020/0323957 | A1 | 10/2020 | Triebel |
| 2021/0177937 | A1 | 6/2021 | Triebel et al. |

FOREIGN PATENT DOCUMENTS

| | | | |
|---|---|---|---|
| CN | 104185681 | A | 12/2014 |
| EA | 003740 | B1 | 8/2003 |
| EP | 0 252 741 | A2 | 1/1988 |
| EP | 1 537 878 | A1 | 6/2005 |
| EP | 2 044 949 | A1 | 4/2009 |
| EP | 2 087 891 | A2 | 8/2009 |
| EP | 3 089 749 | B1 | 5/2019 |
| JP | H05009131 | A | 1/1993 |
| JP | 2006-124383 | A | 5/2006 |
| JP | 2006-141346 | A | 6/2006 |
| JP | 2010-540616 | A | 12/2010 |
| JP | 2012-500006 | A | 1/2012 |
| JP | 2013-126999 | A | 6/2013 |
| JP | 2014-510016 | A | 4/2014 |
| JP | 2017-503014 | A | 1/2017 |
| JP | 2022-97184 | A | 6/2022 |
| KR | 10-2011-0050507 | | 5/2011 |
| WO | 92/05262 | A1 | 4/1992 |
| WO | 96/40210 | A1 | 12/1996 |
| WO | 98/23741 | A1 | 6/1998 |
| WO | 98/23748 | A1 | 6/1998 |
| WO | 98/46728 | A1 | 10/1998 |
| WO | 99/38954 | A1 | 8/1999 |
| WO | 00/72686 | A1 | 12/2000 |
| WO | 01/35989 | A2 | 5/2001 |
| WO | 2005/035779 | A2 | 4/2005 |
| WO | 2005/103079 | A1 | 11/2005 |
| WO | 2007/126805 | A2 | 11/2007 |
| WO | 2007/150077 | A2 | 12/2007 |
| WO | 2008/156712 | A1 | 12/2008 |
| WO | 2009/032256 | A2 | 3/2009 |
| WO | 2009/044273 | A2 | 4/2009 |
| WO | 2010/019570 | A2 | 2/2010 |
| WO | 2011/082400 | A2 | 7/2011 |
| WO | 2012075679 | A1 | 6/2012 |
| WO | 2013/173223 | A1 | 11/2013 |
| WO | 2014/151634 | A1 | 9/2014 |
| WO | 2014/194293 | A1 | 12/2014 |
| WO | 2015/042246 | A1 | 3/2015 |
| WO | 2015/112900 | A1 | 7/2015 |
| WO | 2015/131176 | A1 | 9/2015 |
| WO | 2015/200119 | A1 | 12/2015 |

OTHER PUBLICATIONS

Havell, E.A. et al., "The Antitumor Function of Tumor Necrosis Factor (TNF)", J. Exp. Med. 167:1067-1085 (Mar. 1988).

He, J. et al.., "Circulating Precursor CCR7 10PD-1 hi CXCR5+ CD4+ T Cells Indicate Tfh Cell Activity and Promote Antibody Responses Upon Antigen Reexposure", Immunity 39:770-781 (Oct. 17, 2013).

Hock, H. et al., "Interleukin 7 Induces CD4+ T Cell-Dependent Tumor Rejection", J. Exp. Med. 174:1291-1298 (Dec. 1991).

Hofmeyer, K.A. et al., "The PD-1/PD-LI (B7-H1) Pathway in Chronic Infection-induced Cytotoxic T Lymphocyte Exhaustion", Journal of Biomedicine and Biotechnology vol. 2011, Article ID 451694 (2011).

Holguin, A. et al., "Comparison of Three Different Commercial Methods for Measuring Plasma Viraernia in Patients Infected with Non-B HIV-1 Subtypes", Eur. J Clin Microbial Infect Dis 18:256-259 (1999).

Honeyborne, I. et al., "The Molecular Bacterial Load Assay Replaces Solid Culture for Measuring Early Bactericidal Response to Anti-tuberculosis Treatment", Journal of Clinical Microbiology 52(8):3064-3067 (Aug. 2014).

Honeyborne, L. et al., "Molecular Bacterial Load Assay, a Culture-Free Biomarker for Rapid and Accurate Quantification of Sputum *Mycobacterium tuberculosis* Bacillary Load During Treatment", Journal of Clinical Microbiology 49(11):3905-3911 (Nov. 2011).

Hom, S.S. et al., "Common Expression of Melanoma Tumor-Associated Antigens Recognized by Human Tumor Infiltrating Lymphocytes: Analysis by Human Lymphocyte Antigen Restriction", Journal of Immunotherapy 10:153-164 (1991).

Hu, H-M et al., "Development of Antitumor Immune Responses in Reconstituted Lymphopenic Hosts", Advances in Brief 62:3914-3919 (Jul. 15, 2002).

Huard, B. et al., "Characterization of the Major Histocompatibility Complex Class II Binding Site on LAG-3 Protein", Proc. Natl. Acad. Sci. USA 94:5744-5749 (May 1997).

Huang, A.Y.C. et al., "Role of Bone Marrow-Derived Cells in Presenting MHC Class I-Restricted Tumor Antigens", Science 264:961-965 (1994).

Huebner, K. et al., "The Human Gene Encoding GM-CSF is at 5q21-q32, the Chromosome Region Deleted in the 5q-Anomaly", Science 230(4731):1282-•1285 (1985).

Ill, C.R. et al., "Optimization of the Human Factor VIII Complementary DNA Expression Plasmid for Gene Therapy of Hemophilia A", Blood Coagul Fibrinolysis 8 Suppl. 2:S23-S30 (1997), Abstract.

Ishida, Y et al., "Induced Expression of PD-1, a Novel Member of the Immunoglobulin Gene Superfamily, Upon Programmed Cell Death", The EMBO Journal 11 (11):3887-3895 (1992).

Jaffee, E.M. et al., "Gene Therapy: Its Potential Application in the Treatment of Renal-Cell Carcinoma", Seminars in Oncology 22:81-91 (1995).

Jaffee, E.M. et al., "Novel Allogeneic Granulocyte-Macrophage Colony-Stimulating Factor-Secreting Tumor Vaccine for Pancreatic

(56) References Cited

OTHER PUBLICATIONS

Cancer: A Phase I Trial of Safety and Immune Activation", Journal of Clinical Oncology 19(1):145-156 (2001), Abstract.
Karim, R. et al., "Tumor-Expressed B7-H1 and B7-DC in Relation to PD-1+ T-Cell Infiltration and Survival of Patients With Cervical Carcinoma", Clin Cancer Res 15(20):6341-6347 (Oct. 15, 2009).
Kawakami, Y. et al., "Shared Human Melanoma Antigens, Recognition by Tumor-Infiltrating Lymphocytes in HLA-A2. 1-Transfected Melanomas", J. Immunol. 148:638-643 (1992) (Abstract).
Kelly, K. et al., "Avelumab (MSB0010718C), an Anti-PD-LI Antibody, in Patients With Metastatic or Locally Advanced Solid Tumors: Assessment of Safety and Tolerability in a Phase I, Open-Label Expansion Study", J Clin Oncol vol. 33 ASC University (4 pages) (2015).
K!rkin AF. et al., "Melanoma-Associated Antigens Recognized by Cytotoxic T Lymphocytes", APMIS 106:665-679 (1998).
Kim, D.W. et al., "Use of Human Elongation Factor 1a Promoter as a Versatile and Efficient Expression System", Gene 91(2):217-223 (1990).
Klein, E. et al., "Properties of the K562 Cell Line, Derived from a Patient with Chronic Myeloid Leukemia", Int. J. Cancer 18:421-431 (1976).
Kruskal, J.B., "An Overview of Sequence Comparison", Chapter 1, pp. 1-44 (1983).
Larkin, M.A. et al., "Clustal Wand Clustal X Version 2.0", Bioinformatics 23 (21):2947-2948 (2007).
Latchman, Y. et al., "PD-L2 is a Second Ligand for PD-1 and Inhibits T Cell Activation", Nature Immunology 2(3):261-268 (Mar. 2001).
Lee, C-T et al., "Genetic Immunotherapy of Established Tumors with Adenovirus-Murine Granulocyte-Macrophage Colony-Stimulating Factor", Human Gene Therapy 8:187-193 (1997).
Lee, K-H et al., "Increased Vaccine-Specific T Cell Frequency After Peptide-Based Vaccination Correlates With Increased Susceptibility to In Vitro Stimulation But Does Not Lead to Tumor Regression", The Journal of Immunology 163:6292-6300 (1999).
Li, B. et al., "Lymphocyte Activation Gene-3 Fusion Protein Increases the Potency of a Granulocyte Macrophage Colony-Stimulating Factor-Secreting Tumor Cell Immunotherapy", Clinical Cancer Research 14(11):3545-3554 (Jun. 1, 2008).
Li, B. et al., "Established B16 Tumors are Rejected Following Treatment with GM-CSF-Secreting Tumor Cell Immunotherapy in Combination With Anti-4 1BB mAB", Clinical Immunology Academic Press, U.S. 125:76-87 (2007).
Li, B. et al., "Recombinant IL-7 Enhances U1e Potency of GM-CSF-Screening Tumor Cell Immunotherapy", Clinical Immunology Academic Press, US 123:155-165 (2007).
Matsuzaki, J. et al., "Tumor-Infiltrating NY-ES0-1-Specific CD8+ T Cells are Negatively Regulated by LAG-3 and PD-1 in Human Ovarian Cancer", PNAS 107{17):7875-7880 (Apr. 27, 2010).
Menzies, AM. et al., "New Combinations and Immunotherapies for Melanoma", Ther Adv Med Oncol. 5(5):278-285 (2013).
Miller, M.D. K.M. et al., "Paclitaxel Plus Bevacizumab Versus Paclitaxel Alone for Metastatic Breast Cancer", The New England Journal of Medicine 357:2666-2676 (Dec. 27, 2007).
Moser, K.L. et al., "Genome Scan of Human Systemic Lupus Erythematosus: Evidence for Linkage on Chromosome 1q in African-American Pedigrees", Proc. Natl. Acad. Sci. USA 95:14869-14874 (Dec. 1998).
Nadkarni, M.A. et al., "Determination of Bacterial Load by Real-Time PCR Using a Broad-Range (Universal) Probe and Primers Set", Microbiology 148:257-266 (2002).
Nagai, E. et al., "Irradiated Tumor Cells Adenovirally Engineered to Secrete Granulocyte/Macrophage-Colony-Stimulating Factor Established Antitumor Immunity and Eliminate Pre-Existing Tumors in Syngeneic Mice", Cancer Immunol Immunother 47:72-80 (1998).
Naidoo, J. et al., "Immune Modulation for Cancer Therapy", British Journal of Cancer 111:2214-2219 (2014).
Needleman, S.B. et al., "A General Method Applicable to the Search for Similarities in the Amino Acid Sequence of Two Proteins", J. Mol. Biol. 48:443-453 (1970).
Nirschl C.J. et al., "Molecular Pathways: Coexpression of Immune Checkpoint Molecules: Signaling Pathways and Implications for Cancer Immunotherapy", Clinical Cancer Research 19(18):4917-4924 (Sep. 15, 2013).
Nguyen, L.T. et al., "Clinical Blockade of PD1 and LAG3-Potential Mechanisms of Action", Nature Reviews: Immunology 15:45-56 (Jan. 2015).
Nowak, A.K. et al., "Synergy Between Chemotherapy and Immunotherapy in the Treatment of Established Murine Solid Tumors", Cancer Research 63:4490-4496 (Aug. i, 2003).
Okazaki, T. et al., "A Rheostat for Immune Responses: The Unique Properties of PD-1 and Their Advantages for Clinical Application", Nature Immunology 14(12):1212-1218 (Dec. 2013).
Pardoll, D.M., "The Blockage of Immune Checkpoints in Cancer Immunotherapy", Nature Reviews Cancer 12:252-264 (Apr. 2012).
Philips, G.K. et al., "Therapeutic Uses of Anti-PD-1 and Anti-PD-L1 Antibodies", International Immunology 27(1 ):39-46 (2014).
Pittet, C.L. et al., "Human Brain Endothelial Cells Endeavor to Immunoregulate CD8 T Cells via PD-1 Ligand Expression in Multiple Sclerosis", Journal of Neuroinflammation 8:155 (2011).
Porgador, A. et al., "Immunotherapy of Tumor Metastasis via Gene Therapy", Nat. Immun. 13:113-130 (1994), Abstract.
Postow, M.A. et al., "Immune Checkpoint Blockade in Cancer Therapy", Journal of Clinical Oncology 33:1-9 (2015).
Albert, R. K. et al., "The Merck Manual of Diagnosis and Therapy 18th Edition", Merck Research Labratories, pp. 1161-1167 (2006).
Andreae S. et al., "MHC class II signal transduction in human dendritic cells induced by a natural ligant, the LAG-3 protein (CD223)", Blood 102(6):2130-2137 (2003).
Blackburn, S. D. et al., "Coregulation of CD8+ T cell exhaustion by multiple inhibitory receptors during chronic viral infection", Nature Immunology 10(1):29-37 (Nov. 30, 2008).
Brendel, E. et al., "Pharmacokinetic results of a phase I trial of sorafenib in combination with dacarbazine in patients, with advanced solid tumors", Cancer Chemother Pharmacol, 68:53-61 (2011).
Collins, J.L., et al. "The anticancer drug, cisplatin, increases the naturally occuring cell-mediated lysis of tumor cells", Cancer Immunology Immunotherapy, 29:17-22 (May 1989).
Collins, J.L., et al. "Humans express natural cytotoxic (NC) cell activity that is similar to murine NC cell activity", 138(12):4180-4184 (Jun. 15, 1987).
Commandone, A. et al., "High dose methotrexate in adult patients with osteosarcoma: Clinical and pharmacokinetic results", Acta Oncologica, 44:406-411 (2005).
Cukier-Meisner, E. "Walking the toll road", BioCentury, Product Development, (2014), p. 3 only.
Frank, H. et al., "The Determination of Plasma Volume in Man with Radioactive Chromic Chloride", The Biophysical Laboratory and the Department of Medicine, Harvard Medical School, and the Medical Clinic, Peter Bent Brigham Hospital, Boston, Mass., pp. 991-999 (1953).
Goldsmith, M.A. et al., "Quantitative Prediction of Drug Toxicity in Humans from Toxicology in Small and Large Animals", Cancer Research 35:1354-1364 (1975).
Hemon P. et al., "MHC Class II Engagement by its Ligand LAG-3 (CD223) Contributes to Melanoma Resistance to Apoptosis", The Journal of Immunology 186:5173-5183 (2011).
Kholodov L.E. et al., "Clinical Pharmacokinetics", M.: Medicine., pp. 83-98, 134-138, 160, 378-380 (1985) (cited and discussed in the Office Action (English translation provided) dated Dec. 27, 2021 issued in Russian Application No. 2017127000/04(046505)).
Koh, T.J. et al., "Inflammation and wound healing: The role of the macrophage", Expert Rev Mol Med, (2013), 13, e23,14 pages.
Legat, A., et al., "Vaccination with LAG-3Ig (IMP321) and Peptides Induces Specific CD4 and CD8 T-Cell Responses in Metastatic Melanoma Patients Report of a Phase I/IIa Clinical Trial", Clin Cancer Res, 22(6):1330-1340 (Mar. 15, 2016).
Leveque, D. et al., "Pharmacokinetics of Therapeutic Monoclonal Antibodies Used in Oncology", Anticancer Research, 25:2327-2344 (2005).

(56) References Cited

OTHER PUBLICATIONS

Lozzio, C.B. et al., "Human Chronic Myelogenous Leukemia Cell-Line with Positive Philadelphia Chromosome", Blood, 45(3):321-334 (1975).
Maxwell, M.B. et al., "Chemotherapy-Induced Myelosuppression", Seminars in Oncology Nursing, 8(2):113-123 (1992).
Okazaki, T. et al., "PD-1 and LAG-3 Inhibitory Co-Receptors Act Synergistically to Prevent Autoimmunity in Mice", JEM, 208:395-407 (Year: 2011).
Parchment, R.E., "Bone Marrow as a Critical Normal Tissue that Limits Drug Dose/Exposure in Preclinical Models and the Clinic", Tumor Models in Cancer Research, 2nd Edition, (2011 ), Cancer Drug Discovery and Development, Teicher, Ed., pp. 521-552.
Powell, C.B. et al., "Reduced Natural Cytotoxic Cell Activity in Patients Receiving Cisplatin-Based Chemotherapy and in Mice Treated with Cisplatin", Clinical Experiments in Immunology, 79:424-429 (1990).
Robert, C. et al., "Anti-Programmed-Death-Receptor-1 Treatment with Pembrolizumab in Ipilimumab-Refractory Advanced Melanoma: a Randomised Dose-Comparison Cohort of a Phase 1 Trial", The Lancet 384:1109-17 (Year: 2014).
Rowinsky E.K. et al., "Phase I and Pharmacological Study of Topotecan: A Novel Topoisomerase I Inhibitor", Journal of Clinical Oncology, 10:647-656 (1992).
Sergeev M. et al., "A short Course in Molecular Pharmacology", M.: Moscow Medical Institute named after N.I. Pirogov, p. 10 (1975) (cited and discussed in the Office Action (English translation provided) dated Dec. 27, 2021 issued in Russian Application No. 2017127000/04(046505)).
Shapiro M. et al., "Lymphocyte Activation Gene 3: A Novel Therapeutic Target in Chronic Lymphocytic Leukemia", Haematologica 102(5):874-882 (2017).
Tafuto S. et al., "A Comparison of Two GM-CSF Schedules to Counteract the Granulo-monocytopenia of Carboplatin-Eloposide Chemotherapy", European Journal of Cancer, 31A(1):46-49 (1995).
Teng M.N. et al., "Long-term inhibition of tumor growth by tumor necrosis factor in the absence of cachexia or T-cell Immunity", PNAS, 88:3535-3539 (1991).
Wang Y. et al., "Evaluation on the Antitumor Activity of Topotecan on Fresh Human Breast Cancer Cell", Cancer Research and Clinic, 14(4):225-226 (2002), with English language abstract.
Wang-Gillam A. et al., "A Phase I Study of IMP321 and Gemcitabine as the Front-line Therapy in Patients with Advanced Pancreatic Adenocarcinoma", Invest New Drugs, 31(3):707-713 (2013).
Woo, Seng-Ryong et al., "Immune inhibitory molecules LAG-3 and PD-1 synergistically regulate T cell function to promote tumoral immune escape", Cancer Research, 72(4):917-927 (Dec. 20, 2011).
Clinical Trial Study NCT00351949 (version 2) (2006).
Environmental Protection Agency, Federal Register, (1992), vol. 57, No. 109, pp. 24152-24173.
FDA news release, (2014), FDA approves Keytruda for advanced melanoma, 2 pages.
FDA news release, (2014), FDA approves Opdivo for advanced melanoma, 2 pages.
Highlights of Prescribing Information, Keytruda, Merck & Co., Inc., 12 pages.
Highlights of Prescribing Information, Opdivo, 8 pages.
Clinical Trail Study NCT00349934 (version 1), IMP321 Phase 1 Breast Carcinoma, first posted on Jul. 10, 2006.
English translation of Chinese Office Action dated Apr. 28, 2018 issued in CN 20140073584.3.
International Search Report dated May 6, 2016 issued in PCT/EP2016/050321.
Extended European Search Report dated Nov. 13, 2019 issued in European Patent Application No. 19189911.1.
Japanese Office Action dated Nov. 5, 2019 issued in Japanese Patent Application No. 2017-536009, together with English language translation.
Russian Office Action dated Jul. 30, 2019 issued in Russian Patent Application No. 2017127000.
Russian Search Report dated Jul. 29, 2019 issued in Russian Patent Application No. 2017127000.
Russian Office Action dated Feb. 5, 2020 received in Russian Application No. 2017127000, together with an English-language translation.
Russian Office Action dated Dec. 27, 2021 received in Russian Application No. 2017127000/04(046505), together with an English-language translation.
Office Action dated Aug. 5, 2019 received in U.S. Appl. No. 15/542,466.
Office Action dated Feb. 14, 2019 received in U.S. Appl. No. 15/542,466.
U.S. Final Office Action dated Aug. 3, 2021 received in U.S. Appl. No. 16/274,466.
U.S. non-Final Office Action dated Apr. 20, 2022 received in related U.S. Appl. No. 16/274,466.
U.S. non-Final Office Action dated Feb. 19, 2021 received in U.S. Appl. No. 16/274,466.
Loken M.R. et al., "Establishing Optimal Lymphocyte Gates for Immunophenotyping by Flow Cytometry", Cytometry 11(4):453-469 (1990) (cited in CN OA dated Apr. 28, 2023).
Nicholson J.K.A. et al., "Use of CD45 Fluorescence and Side-Scatter Characteristics for Gating Lymphocytes When Using the Whole Blood Lysis Procedure and Flow Cytometry", Cytometry (Communications in Clinical Cytometry) 26:16-21 (1996) (cited in CN OA dated Apr. 28, 2023).
Chinese Office Action dated Apr. 28, 2023 received in Chinese Application No. 202111358413.3, together with an English-language translation.
Chinese Office Action dated Aug. 31, 2023 received in Chinese Application No. 202111344452.8, together with an English-language translation.
Desoize B. et al., "Particular Aspects of Platinum Compounds Used at Present in Cancer Treatment", Critical Reviews in Oncology/Hematology 42:317-325 (Dec. 31, 2002).
Hao Y., "Study on the Regular, Long-Circulating and Temperature-Sensitive Liposomes of Topotecan Hydrochloride", Chinese Doctoral Dissertations Full-text Database, Medicine and Health Sciences, No. 3 (Mar. 15, 2011), cited in Chinese Office Action dated Jul. 30, 2024 received in Chinese Application No. 202110293412.9.
Chinese Office Action & Search Report dated Jul. 30, 2024 received in Chinese Application No. 202110293412.9, together with an English-language translation.
Plaksin, D. et al., "Effective Anti-Metastatic Melanoma Vaccination With Tumor Cells Transfected With Mice Genes and/or Infected With Newcastle Disease Virus (NDV)", Int. J. Cancer 59:796-801 (1994).
Prigent, P. et al., "Lymphocyte Activation Gene-3 Induces Tumor Regression and Antitumor Immune Responses", Eur. J. Immunol. 29:3867-3876 (1999).
Rabe, H. et al., "*Staphylococcus aureus* Convert Neonatal Conventional CD4+ T Cells into FOXP3+ CD25+ CD127low T Cells via the PD-1/PD-L1 Axis", Immunology 141:467-481 (2013).
Riott, et al., "Antigens are Partially Degraded into Peptides Before Binding to MHC Molecules", Immunology, 4th Edition, pp. 7.9-7.11 (1996).
Rivera, V.M. et al., "A Humanized System for Pharmacologic Control of Gene Expression", Nature Med 2(9):1028-1032 (1996).
Rozali, E.N. et al., "Programmed Death Ligand 2 in Cancer-Induced Immune Suppression", Clinical and Development Immunology 2012:656340 (8 pages) (2012).
Salgia, R. et al., "Vaccination With Irradiated Autologous Tumor Cells Engineered to Secrete Granulocyte-Macrophage Colony-Stimulating Factor Augments Antitumor Immunity in Some Patients With Metastatic Non-Small Cell Lung Carcinoma", J. Clinical Oncol. pp. 624-630 (2003).
Samulski, R. J. et al., "Helper-Free Stocks of Recombinant Adena-Associated Viruses: Normal Integration Does Not Require Viral Gene Expression", Journal of Virology 63(9):3822-3828 (Sep. 1989).

(56) References Cited

OTHER PUBLICATIONS

Salvadori, S. et al., "B7-1 Amplifies the Response to Interleukin-2-Secreting Tumor Vaccines In Vivo, But Fails to Induce a Response by Naive Cells In Vivo", Human Gene Therapy 6:1299-1306 (1995).
Sawyter, T.K. et al., "Src Homology-2 Inhibitors: Peptidomimetic and Nonpeptides", Mini. Rev. in Med. Chem. 2(5):475-488 (2002).
Seung, E. et al., "PD-1 Blockade in Chronically HIV-1-Infected Humanized Mice Suppresses Viral Loads", PLOS One8(10):e77780 (Oct. 2013).
Shinohara, T. et al., "Structure and Chromosomal Localization of the Human PD-1 Gene (PDCD1)", Genomics 23:704-706 (1994).
Shih, K. et al., "Clinical Impact of Checkpoint Inhibitors as Novel Cancer Therapies", Drugs 74:1993-2013,(21 pages) (Oct. 25, 2014).
Simons, J.W. et al., "Induction of Immunity to Prostate Cancer Antigens: Results of a Clinical Trial of Vaccination with Irradiated Autologous Prostate Tumor Cells Engineered to Secrete Granulocyte-Macrophage Colony-Stimulating Factor Using Ex Vivo Gene Transfer", Cancer Research 59:5160-5168 (Oct. 15, 1999).
Simons, J.W. et al., "Bioactivity of Autologous Irradiated Renal Cell Carcinoma Vaccines Generated by Ex Vivo Granulocyte-Macrophage Colony-Stimulating Factor Gene Transfer", Cancer Research 57:1537-1546 (Apr. 15, 1997).
Simmons, A.D. et al., "GM-CSF-Secreting Cancer Immunotherapies: Preclinical Analysis of the Mechanism of Action", Cancer Immunology, Immunotherapy, Springer, Berlin DE 56:1653-1665 (2007).
Soiffer, R. et al., "Vaccination with Irradiated Autologous Melanoma Cells Engineered to Secrete Human Granulocyte-Macrophage Colony-Stimulating Factor Generates Potent Antitumor Immunity in Patients With Metastatic Melanoma", Proc. Natl. Acad. Sci. USA 95:13141-13146 (Oct. 1998).
Suntharalingam, G. et al., "Cytokine Storm in a Phase 1 Trial of the Anti-CD28 Monoclonal Antibody TGN1412", The New England Journal of Medicine 355(10):1018-1028 (Sep. 7, 2006).
Swenson, L.C. et al., "Comparative Performances of HIV-1 RNA Load Assays at Low Viral Load Levels: Results of an International Collaboration", Journal of Clinical Microbiology 52(2):517-523 (Feb. 2014).
Tang, C-H et al., "The CCL5/CCR5 Axis Promotes Interleukin-6 Production in Human Synovial Fibroblasts", Arthritis & Rheumatism 62(12):3615-3624 (Dec. 2010).
Taylor, P.C. et al., "Anti-TNF Biologic Agents: Still the Therapy of Choice for Rheumatoid Arthritis", Nature Reviews Rheumatology 5:578-582 (Oct. 2009).
Togno-Peirce, C. et al., "Sex-Associated Expression of Co-Stimulatory Molecules CD80, CD86, and Accessory Molecules, PDL-1, PDL-2 and MHC-11, in F480+ Macrophages During Murine Cysticercosis", BioMed Research International 2013:570158 (9 pages) (2013).
Triebel, F., "LAG-3: A Regulator of T-Cell and DC Responses and its Use in Therapeutic Vaccination", Trends in Immunology 24(12):619-622 (Dec. 2003).
Triebel, F. et al., "LAG-3, A Novel Lymphocyte Activation Gene Closely Related to CD4", J. Exp. Med. 171:1393-1405 (May 1990).
Tseng, S-Y et al., "B7-DC, a New Dendritic Cell Molecule With Potent Costimulatory Properties for T Cells", J. Exp. Med. 193(7):839-845 (Apr. 2, 2001).
Tsushima, F. et al., "Preferential Contribution of B7-HI to Programmed Death-1-Medated Regulation of Hapten-Specific Allergic Inflammatory Responses", Eur. J. Immunol. 33:2773-2782 (2003).
Velu, V. et al., "Role of PD-1 Co-inhibitory Pathway in HIV Infection and Potential Therapeutic Options", Retrovirology vol. 12:14 (17 pages) (2015).
Vibhaker, R. et al., "Activation-Induced Expression of Human Programmed Death-1 Gene in T-Lymphocytes", Experimental Cell Research 232:25-28 (1997).
Walczak, J.R. et al., "Pharmacological Treatments for Prostate Cancer" Expert Opin. Investig. Drugs. 11:1737-1748 (2002), Abstract.
Wang, W. et al., "PD1 Blockade Reverses the Suppression of Melanoma Antigen-Specific CTL by CD4+CD25HI Regulatory T Cells", International Immunology 21(9):1065-1077 (2009).
Wherry, E.J. et al., "Molecular Signature of CD8+ T Cell Exhaustion During Chronic Viral Infection", Immunity 27:670-684 (Oct. 2007).
Ye, X. et al., "Regulated Delivery of Therapeutic Proteins After In Vivo Somatic Cell Gene Transfer", Science 283:88-91 (1999).
Ye, B. et al., "T-Cell Exhaustion in Chronic Hepatitis B Infection: Current Knowledge and Clinical Significance", Cell Death and Disease 6:e1694 (2015).
Youngnak, P. et al., "Differential Binding Properties of B7-H4 and B7-DC to Programmed Death-1", Biocl1ernical and Biophysical Research Communications 307:672-677 (2003).
Zaidi, M.R. et al., "The Two Faces of Interferon-y in Cancer", Clin Cancer Res. 17(19):6118-6124 (Oct. i, 201 i).
Zajac, A.J. et al., "Viral Immune Evasion Due to Persistence of Activated T Cells Without Effector Function", J. Exp. Med. 188(12):2205-2213 (Dec. 21, 1998).
Zhang, V. et al., "Programmed Death-1 Upregulation is Correlated With Dysfunction of Tumor-Infiltrating CD8+ T Lymphocytes in Human Non-Small Cell Lung Cancer", Cellular & Molecular Immunoloav 7:389-395 (2010).
Zou, W. et al., "Inhibitory B7-Family Molecules in the Tumour Microenvironment", Nature Reviews—Immunology 8:467-477 (Jun. 2008).
FDA-Guidance for Industry-Estimating the Maximum Safe Starting Dose in Initial Clinical Trials for Therapeutics in Adult Healthy Volunteers, Pharmacology and Toxicology (30 pages) (Jul. 2005).
Principles of Cancer Therapy: The Merck Manual of Diagnosis and Therapy, 18th Edition, p. 1164, table 149-2 (2006).
NCBI Reference Sequence: NM_005018.2, Gibson A. et al., "*Homo sapiens* Programmed Cell Death 1 (PDCD1), mRNA", J. Immunol. 192(6):2611-2621 (2014).
NCBI Reference Sequence: NM_025239.3, Wang G. et al., "*Homo sapiens* Programmed Cell Death 1 Ligand 2 (PCDD1LG2), mRNA", Xi Bao Yu Fen Zi Mian Yi Zue Za Zhi 29(2):132-136 (2013).
NCBI Reference Sequence: AF233516.1, Freeman G.J. et al., "*Homo sapiens* PD-1 Ligand Precursor, mRNA, Complete CDS", J. Exp. Med. 192(7):1027-1034 (2000).
Safety Study of Anit-LAG-3 With and Without Anti-PD-1 in the Treatment of Solid Tumors, ClinicalTrials.gov, Clinical Trial No. NCT01968109 (4 pages) (2013).
International Search Report and Written Opinion dated Mar. 26, 2015 received in International Application No. PCT/EP2014/078779.
Great Britain Search Report dated Oct. 22, 2015 received in British Application No. 1500374.2.
English Translation of the Notification of the First Office Action dated Apr. 28, 2018 issued in Chinese Patent Application No. 201480073584.3.
English Translation of the Notice of Reasons for Rejection dated Aug. 30, 2018 issued in Japanese Patent Application No. 2016-559686.
Extended European Search Report dated Mar. 27, 2019 issued in European Patent Application No. 18208378.2.
Intemational Search Report dated Mar. 27, 2009 issued in PCT/US2008/010335.
Altschul, S.F. et al., "Basic Local Alignment Search Tool", J. Mol. Biol. 215:403-410 (1990).
Altschul, S.F. et al., "Gapped BLAST and PSI-BLAST: A New Generation of Protein Database Search Programs", Nucleic Acids Research 25(17):3389-3402 (1997).
Aoki, T. et al., "Expression of Murine Interleukin 7 in a Murine Glioma Cell Line Results in Reduced Tumorigenicity In Vivo", Proc. Natl. Acad. Sci. USA 89:3850-3854 (May 1992).
Armand P. et al., "Disabling Immune Tolerance by Programmed Death-1 Blockade With Pidilizumab After Autologous Hematopoietic Stem-Cell Transplantation for Diffuse Large B-Cell Lymphoma: Results of an International Phase II Trial", Journal of Clinical Oncology 31(33):4199-4206 (Nov. 20, 2013).
Armstrong, T.D. et al., "Cytokine Modified Tumor Vaccines", Surg. Oncology Clin. N. Am. 11:681-696 (2002).

(56) References Cited

OTHER PUBLICATIONS

Asher, A.L. et al., "Murine Tumor Cells Transduced With the Gene for Tumor Necrosis Factor-α", J. Immunol. 146:3227-3234 (1991).
Barber, D.L. et al., "Restoring Function in Exhausted CD8 T Cells During Chronic Viral Infection", Nature 439:682-687 (Feb. 2006).
Benson, Jr. D.M. et al., "The PD-1/PD-L1 Axis Modulates the Natural Killer Cell Versus Multiple Myeloma Effect: A Therapeutic Target for CT-011, a Novel Monoclonal Anti-PD-1 Antibody", Blood 116(13):2286-2294 (Sep. 30, 2010).
Berkelhammer, J. et al., "Development of a New Melanoma Model in C57BL/6 Mice", Cancer Research 42:3157-3163 (Aug. 1982).
Blackburn, S.D. et al., "Selective Expansion of a Subset of Exhausted CD8 T Cells by aPD-L1 Blockade", PNAS 105(39):15016-15021 (Sep. 30, 2008).
Blank, C. et al., "Blockade of PD-L1 (B7-H1) Augments Human Tumor-Specific T Cell Responses In Vitro", Int. J. Cancer 119:317-327 (2006).
Blattman, J.N. et al., "Impact of Epitope Escape on PD-1 Expression and CD8 T-Cell Exhaustion During Chronic Infection", Journal of Virology 83(9):4386-4394 (May 2009).
Bock, S.N. et al., "Biological and Antitumor Effects of Recombinant Human Macrophage Colony-Stimulating Factor in Mice", Cancer Research 51:2649-2654 (May 15, 1991).
Bodey, B. et al., "Failure of Cancer Vaccines: The Significant Limitations of this Approach to Immunotherapy", Anticancer Research 20:2665-2676 (2000), Abstract.
Boon, T., "Toward a Genetic Analysis of Tumor Rejection Antigens", Advances in Cancer Research 58:177-210 (1992).
Brignone, C. et al., "First-Line Chemoimmunotherapy in Metastatic Breast Carcinoma: Combination of Paclitaxel and IMP321 (LAG-3Ig) Enhances Immune Responses and Antitumor Activity", Journal of Translational Medicine 8:71 (2010).
Brignone, C. et al., "A Phase I Pharmacokinetic and Biological Correlative Study of IMP321, a Novel MHC Class II Agonist, in Patients With Advanced Renal Cell Carcinoma", Cancer Therapy: Clinical 15(19):6225-6231 (Oct. 1, 2009).
Brignone, C. et al., "A Soluble Form of Lymphocyte Activation Gene-3 (IMP321) Induces Activation of a Large Range of Human Effector Cytotoxic Cells", The Journal of Immunology 179:4202-4211 (2007).
Brignone, C. et al., "IMP321 (sLAG-3) Safety and T Cell Response Potentiation Using an Influenza Vaccine as a Model Antigen: A Single-Blind Phase I Study", Vaccine 25:4641-4650 (2007).
Brignone, C. et al., "IMP321 (sLAG-3), an Immunopotentiator for T Cell Responses Against a HBsAg Antigen in Healthy Adults: A Single Blind Randomised Controlled Phase I Study", Journal of Immune Based Therapies and Vaccines 5(5):1-15 (2007).
Brown, J.A. et al., "Blockade of Programmed Death-1 Ligands on Dendritic Cells Enhances T Cell Activation and Cytokine Production", The Journal of Immunology 170:1257-1266 (2003).
Buisson, S. et al., "LAG-3 (CD223) Reduces Macrophage and Dendritic Cell Differentiation from Monocyte Precursors", Immunology 114:369-374 (2005).
Bukowski, R.M. et al., "Phase I Trial of Subcutaneous Recombinant Macrophage Colony-Stimulating Factor: Clinical and Immunomodulatory Effects", Journal of Clinical Oncology 12(1):97-106 (1994).
Campanella, J.J. et al., "MatGAT: An Application that Generates Similarity/Identity Matrices Using Protein or DNA Sequences", BMC Bioinformatics 4:29 (2003).
Cantrell, M.A. et al., "Cloning, Sequence, and Expression of a Human Granulocyte/Macrophage Colony-Stimulating Factor", Proc. Natl. Acad. Sci. USA 82:6250-6254 (Sep. 1985).
Cao, D. et al., "Intrahepatic Expression of Programmed Death-1 and its Ligands in Patients with HBV-Related Acute-on-Chronic Liver Failure", Inflammation 36(1):110-120 (Feb. 2013).
Casati, C. et al., "Soluble Human LAG-3 Molecule Amplifies the In Vitro Generation of Type 1 Tumor-Specific Immunity", Cancer Research 66(8):4450-4460 (Apr. 15, 2006).
Castellino, F. et al., "Chemokines Enhance Immunity by Guiding Naïve CD8+ T Cells to Sites of CD4+ T Cell-Dendritic Cell Interaction", Nature 440:890-895 (Apr. 13, 2006).
Chang, A.E. et al., "Immunogenetic Therapy of Human Melanoma Utilizing Autologous Tumor Cells Transduced to Secrete Granulocyte-Macrophage Colony-Stimulating Factor", Human Gene Therapy 11:839-850 (Apr. 10, 2000).
Chaux, P. et al., "Estimation of the Frequences of Anti-Mage-3 Cytolytic T-Lymphocyte Precursors in Blood from Individuals Without Cancer", Int. J. Cancer 77:538-542 (1998).
Curiel, T.J. et al., "Blockade of B7-H1 Improves Myeloid Dendritic Cell-Mediated Antitumor Immunity", Nature Medicine 9(5):562-567 (May 2003).
Darrow, T.L. et al., "The Role of HLA Class I Antigens in Recognition of Melanoma Cells by Tumor-Specific Cytotoxic T Lymphocytes", 142:3329-3335 (1989).
Dicarlo, E. et al., "Immunological Mechanisms Elicited at the Tumour Site by Lymphocyte Activation Gene-3 (LAG-3) Versus IL-12; Sharing a Common Th1 Anti-Tumour Immune Pathway", Journal of Pathology GB 205:82-91 (2005).
Dienz, O. et al., "The Effects of IL-6 on CD4 T Cell Responses", Clin Immunol. 130(1):27-33 (Jan. 2009).
Dong, H. et al., "Tumor-Associated B7-H1 Promotes T-Cell Apoptosis: A Potential Mechanism of Immune Evasion", Nature Medicine 8(8):793-800 (Aug. 2002).
Dorner, B.G. et al., "MIP-1α, MIP-1β, Rantes, and ATAC/Lymphotactin Function Together with IFN-γ as Type 1 Cytokines", PNAS 99(9):6181-6186 (Apr. 30, 2002).
Dranoff, G. et al., "Vaccination with Irradiated Tumor Cells Engineered to Secrete Murine Granulocyte-Macrophage Colony-Stimulating Factor Stimulates Potent, Specific, and Long-Lasting Anti-Tumor Immunity", Proc. Natl. Acad. Sci. USA 90:3539-3543 (Apr. 1993).
Dummer, R. et al., "GVAX Cell Genesys", Current Opinion in Investigational Drugs 2(6):844-848 (2001), Abstract.
El Mir, S. et al., "A Soluble Lymphocyte Activation Gene-3 Molecule Used as a Vaccine Adjuvant Elicits Greater Humoral and Cellular Immune Responses to Both Particulate and Soluble Antigens", The Journal of Immunology 164:5583-5589 (2000).
Fearson, E.R. et al., "Interleukin-2 Production by Tumor Cells Bypasses T Helper Function in the Generation of an Antitumor Response", Cell 60:397-403 (1990).
Finger, R.L. et al., "The Human PD-1 Gene: Complete cDNA, Genomic Organization, and Developmentally Regulated Expression in B Cell Progenitors", Gene 197:177-187 (1997).
Fougeray, S. et al., "A Soluble LAG-3 Protein as an Immunopotentiator for Therapeutic Vaccines: Preclinical Evaluation of IMP321", Vaccine 24:5426-5433 (2006).
Gallimore, A. et al., "Induction and Exhaustion of Lymphocytic Choriomeningitis Virus-Specific Cytotoxic T Lymphocytes Visualized Using Soluble Tetrameric Major Histocompatibility Complex Class I-Peptide Complexes", J. Exp. Med. 187(9):1383-1393 (May 4, 1998).
Gansbacher, B. et al., "Retroviral Vector-Mediated ??—Interferon Gene Transfer into Tumor Cells Generates Potent and Long Lasting Antitumor Immunity", Cancer Research 50:7820-7825 (Dec. 15, 1990).
Gansbacher, B. et al., "Interleukin 2 Gene Transfer into Tumor Cells Abrogates Tumorigenicity and Induces Protective Immunity", J. Exp. Med. 172:1217-1224 (Oct. 1990).
Ghiotto, M. et al., "PD-L1 and PD-L2 Differ in Their Molecular Mechanisms of Interaction With PD-1", Int Immunol 22(8):651-660 (Aug. 2010).
Goding, S.R. et al., "Restoring Immune Function of Tumor-Specific CD4+ T Cells During Recurrence of Melanoma", The Journal of Immunology 10:4899-4909 (2013).
Goldschmidt, P.L. et al., "Comparison of an Amplified Enzyme-Linked Immunosorbent Assay With Procedures Based on Molecular Biology for Assessing Human Immunodeficiency Virus Type 1 Viral Load", Clinical and Diagnostic Laboratory Immunology 5(4):513-518 (Jul. 1998).

(56) References Cited

OTHER PUBLICATIONS

Golumbeck, P.T. et al., "Treatment of Established Renal Cancer by Tumor Cells Engineered to Secrete Interleukin-4", Science 254:713-716 (1991).
Griswold, Jr. D.P., "Consideration of the Subcutaneously Implanted B16 Melanoma as a Screening Model for Potential Anticancer Agents", Cancer Chemotherapy Reports Part 2, 3(1):315-324 (Nov. 1972).
Aguilar L.K. et al., "Cytotoxic Immunotherapy Strategies for Cancer: Mechanisms and Clinical Development", Journal of Cellular Biochemistry 112:1969-1977 (2011).
Ruggiero A. et al., "Platinum Compounds in Children With Cancer: Toxicity and Clinical Management", Anticancer Drugs 24(10):1007-1019 (Nov. 2013), Abstract only.
Schlom J. et al., "Cancer Vaccines: Moving Beyond Current Paradigms", Clinical Cancer Research 13(13):3776-3782 (Jul. 1, 2007).
U.S. non-Final Office Action dated Jul. 14, 2023 received in U.S. Appl. No. 16/918,527.
Pinto A C et al., "Schedule Treatment Design and Quantitative In Vitro Evaluation of Chemotherapeutic Combinations for Metastatic Prostate Cancer Therapy", Cancer Chemother Pharmacol 67:275-284 (2011).
Pollaro L. et al., "Strategies to Prolong the Plasma Residence Time of Peptide Drugs", Med. Chem. Commun. 1:319-324 (2010).
U.S. non-Final Office Action dated Dec. 14, 2022 received in U.S. Appl. No. 16/918,527.
Andreae S. et al., "Maturation and Activation of Dendritic Cells Induced by Lymphocyte Activation Gene-3 (CD223)", The Journal of Immunology 168:3874-3880 (2002).
Kondo M. et al., "Early Monocytopenia After Chemotheray as a Risk Factor for Neutropenia", American Journal of Clinical Oncology 22(1):103-105 (Feb. 1999).
Bello C. et al., "Monoclonal Antibodies for B-Cell Lymphomas: Rituximab and Beyond", Hematology 233-242 (Jun. 2007) (cited in non-Final OA).
Hortobagyi G.N., "Overview of Treatment Results With Trastuzumab (Herceptin) in Metastatic Breast Cancer", Seminars in Oncology 28(6):43-47 (Dec. 2001) (cited in non-Final OA).
U.S. Non-Final Office Action dated Jun. 6, 2025 received in U.S. Appl. No. 18/098,199.
Dolan D.E. et al., "PD-1 Pathway Inhibitors: Changing the Landscape of Cancer Immunotherapy", Cancer Control 21(3):231-237 (Jul. 2014).
Guzik K. et al., "Development of the Inhibitors that Target the PD-1/PD-L1 Interaction—A Brief Look at Progress on Small Molecules, Peptides and Macrocycles", Molecules 24:2071 (2019).
Mamalis A. et al., "Targeting the PD-1 Pathway: A Promising Future for the Treatment of Melanoma", Arch Dermatol Res. 306(6):511-519 (Aug. 2014).
McDermott D.F. et al., "PD-1 as a Potential Target in Cancer Therapy", Cancer Medicine 2(5):662-673 (2013).
Sasikumar P.G. et al., "Abstract 2850: Demonstration of Anti-Tumor Efficacy in Multiple Preclinical Cancer Models Using a Novel Peptide Inhibitor (Aurigene-012) of the PD1 Signaling Pathway", Cancer Res. 72(8):2850 (Apr. 15, 2012), Abstract.
Yang M. et al., "Research Progress on Camptothecin and Derivatives Thereof", Journal of Modern Medicine & Health 8:977-978 (Dec. 2003), together with an English-language abstract (cited in CN OA).
Zhang J. et al., "Recent Progress in Research and Development of Antitumor Platinum Drugs and Their Situation on the Market", Shanghai Pharmaceuticals Holding Co., Ltd. 34(23):52-59 (Dec. 2013), together with an English-language abstract (cited in CN OA).
"PD-1 Inhibitor Approved for Melanoma", Cancer Discovery p. 1249 (Nov. 2014).
Japanese Notice of Reasons for Rejection dated May 14, 2025 received in Japanese Application No. 2023-206838, together with an English-language translation.
Chinese Office Action dated Jul. 30, 2025 received in Chinese Application No. 202110293412.9, together with an English-language translation.

A

B

C

D

E

F

G

H i) IMP321: LAG-3 D1D4-linker1-Ig ii) LAG-3 D1D4-linker2-Ig iii) LAG-3 D1D2-linker2-Ig iv) IMP321 R75A:
LAG-3 D1D4-linker1-Ig with point mutation at position R75

Average background (no LAG-3Ig-Alexa488): 405 ± 23;

Average no antibody: 1738 ± 164

Figure 15:
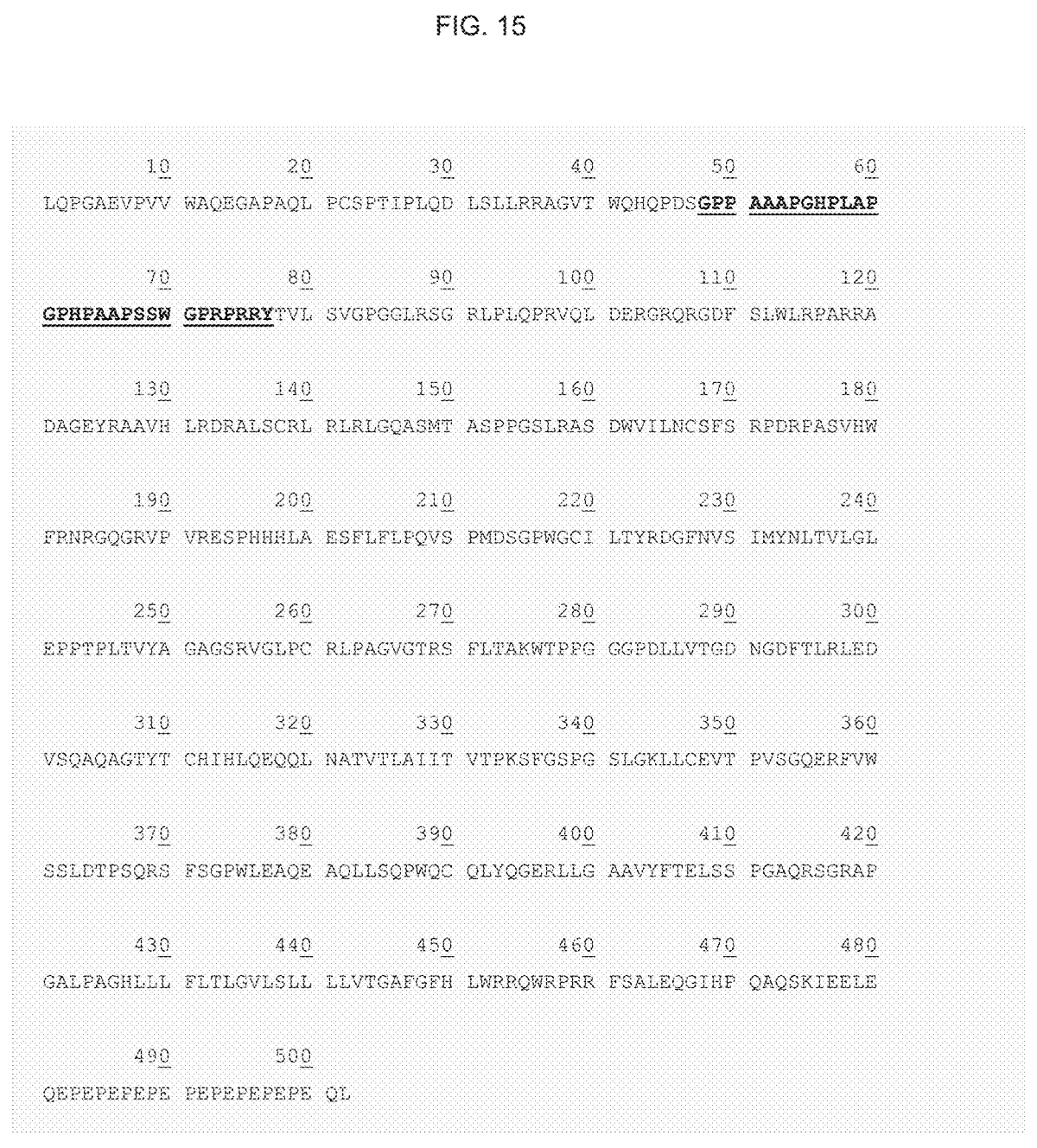

```
        10         20         30         40         50         60
LQPGAEVPVV WAQEGAPAQL PCSPTIPLQD LSLLRRAGVT WQHQPDSGPP AAAPGHPLAP

        70         80         90        100        110        120
GPHPAAPSSW GPRPRRYTVL SVGPGGLRSG RLPLQPRVQL DERGRQRGDF SLWLRPARRA

       130        140        150        160        170        180
DAGEYRAAVH LRDRALSCRL RLRLGQASMT ASPPGSLRAS DWVILNCSFS RPDRPASVHW

       190        200        210        220        230        240
FRNRGQGRVP VRESPHHHLA ESFLFLPQVS PMDSGPWGCI LTYRDGFNVS IMYNLTVLGL

       250        260        270        280        290        300
EPPTPLTVYA GAGSRVGLPC RLPAGVGTRS FLTAKWTPPG GGPDLLVTGD NGDFTLRLED

       310        320        330        340        350        360
VSQAQAGTYT CHIHLQEQQL NATVTLAIIT VTPKSFGSPG SLGKLLCEVT PVSGQERFVW

       370        380        390        400        410        420
SSLDTPSQRS FSGPWLEAQE AQLLSQPWQC QLYQGERLLG AAVYFTELSS PGAQRSGRAP

       430        440        450        460        470        480
GALPAGHLLL FLTLGVLSLL LLVTGAFGFH LWRRQWRPRR FSALEQGIHP QAQSKIEELE

       490        500
QEPEPEPEPE PEPEPEPEPE QL
```

anti-PD1 antibodies anti-PDL1 antibodies

COMBINED PREPARATIONS FOR THE TREATMENT OF CANCER OR INFECTION

CROSS REFERENCE TO RELATED APPLICATIONS

This application is a continuation of U.S. patent application Ser. No. 17/072,612 filed Oct. 16, 2020, which is a divisional of U.S. patent application Ser. No. 15/542,466 filed Jul. 10, 2017, now U.S. Pat. No. 10,874,713, which is a National Stage Entry of International Application No. PCT/EP2016/050321 filed Jan. 8, 2016, the entire contents of which are incorporated herein by reference herein.

FIELD OF THE DISCLOSURE

This disclosure relates to combined preparations and to pharmaceutical compositions, and their use as medicaments, in particular for the treatment of cancer or infection, and to methods for the treatment of cancer or infection.

INCORPORATION BY REFERENCE OF SEQUENCE LISTING

The Sequence Listing in a XML file, named as 35156BZ_SequenceListing.txt of 4 KB, created on Sep. 2, 2022, and submitted to the United States Patent and Trademark Office via Patent Center, is incorporated herein by reference.

BACKGROUND

Upon emerging from the thymus, naive T cells circulate in blood through lymph nodes and seek foreign ("nonself") antigens presented by specific antigen-presenting cells (APCs), typically dendritic cells. T cells can recognize not only pathogen-associated antigens but also abnormally expressed self-proteins—indicating mutated or transformed tumorigenic cells—as "nonself." If T cells encounter their specific antigen in the context of appropriate costimulatory molecules, the cells become activated and upregulate activation and homing molecules. These T cells, termed effector T cells, are able to enter inflamed tissues in search of infected or cancerous cells. Among other functions, effector T cells can produce inflammatory cytokines and/or cytolytic granules, leading to apoptosis or necrosis of infected or tumor cells.

Throughout the duration of an immune response, local and systemic down-regulatory forces minimize damage to healthy cells and tissues. These can involve immunosuppressive cytokines, regulatory T cells (Tregs), and negative signaling from other cells. Tumor antigen-specific T cells display impaired effector function and an exhausted phenotype characterized by decreased production of pro-inflammatory cytokines and hypo-responsiveness to antigenic restimulation. This is mediated by cell-extrinsic mechanisms, such as regulatory T cells (Treg), and cell-intrinsic mechanisms, such as inhibitory molecules that are up-regulated on exhausted, tumor infiltrating lymphocytes (TILs).

Immune checkpoint pathways strongly downregulate T-cell activation with the intent of keeping nascent T-cell responses in check and reducing the likelihood of an immune attack against normal tissues. During tumorigenesis, however, cancer cells may exploit these co-inhibitory pathways to resist detection or avoid elimination by the adaptive immune system. The programmed cell death protein-1 (PD-1) is a critical checkpoint molecule that is expressed by T cells upon activation. The PD-1 checkpoint pathway is thought to act primarily in peripheral tissues to dampen ongoing immune responses and/or to prevent damage to self-tissues. PD-1 is expressed by B cells, natural killer (NK) cells, dendritic cells, and activated monocytes, in addition to T cells. PD-1 ligands—which include PD-L1 and PD-L2, among others—are expressed by macrophages and monocytes, and these can be induced in numerous cell types in an inflammatory environment.

The ability of nonimmune cells to express ligands for PD-1, primarily PD-L1, is exploited by tumors as one way to avoid immune attack. Tumor cells can also down-regulate antigen expression to avoid detection. In addition, production of immunosuppressive mediators and retention of Tregs and immune suppressor cells within the tumor microenvironment can dampen antitumor immune responses.

FIG. 1 (taken from Harvey, Clinical Pharmacology & Therapeutics, 2014, Vol. 96(2), pages 214-223) depicts the role of the PD-1 pathway in tumor immune evasion and the mechanism of action of PD-1 pathway blockade: (a) PD-1 in T-cell activation. T cells are activated via (i) binding of MHC plus peptide on an APC to the TCR and then (ii) binding of APC CD80/86 to T-cell CD28. In patients with cancer, tumor cells can also serve as APCs. Upon T-cell activation, PD-1 expression is induced; (b) PD-1 in T cell exhaustion. In situations of chronic infection or persistent stimulation, PD-L1 signals through T-cell PD-1 to "turn off" T cells in order to minimize damage to healthy tissue (activation signaling is blocked). Tumor cells can upregulate PD-L1 in order to "turn off" T cells that might destroy them. (c) Blocking the PD-1/PD-L1 signaling pathway allows T cells to maintain their effector functions. In patients with cancer, activated tumor-specific T cells can kill tumor cells and secrete cytokines that activate/recruit other immune cells to participate in the antitumor response.

Cloning of PD-1 is described by Ishida, et al. (The EMBO Journal (1992), vol. 11(11), p. 3887-3895). The sequence of human PD-1 cDNA is recorded under GenBank Accession No. NM_005018. The sequence of human PD-L1 cDNA is given at GenBank Accession No. AF233516, and the sequence of human PD-L2 cDNA is given at GenBank Accession No. NM_025239.

In September 2014, the US Food and Drug Administration (FDA) granted accelerated approval to Keytruda (pembrolizumab) for treatment of patients with advanced or unresectable melanoma who are no longer responding to other drugs. Keytruda (Merck & Co.) is a humanized monoclonal IgG4 antibody against PD-1. It comprises variable region sequences of a very-high-affinity mouse antihuman PD-1 antibody grafted into a human IgG4 immunoglobulin, with an alteration to increase stability. Keytruda blocks binding of PD-1 to PD-L1 and PD-L2.

In December 2014, the US FDA also granted accelerated approval to Opdivo (nivolumab), a new treatment for patients with unresectable or metastatic melanoma who no longer respond to other drugs. Opdivo (Bristol-Myers Squibb) is a fully human monoclonal IgG4 antibody against PD-1 that blocks binding of PD-1 to PD-L1 and PD-L2.

Nivolumab has undergone the most extensive clinical evaluation in lung cancer among the PD-1 pathway inhibitors. Evidence of activity both as a monotherapy in squamous and nonsquamous non-small-cell lung carcinoma (NSCLC) and in combination with conventional chemotherapy has been demonstrated in patients with NSCLC. Pembrolizumab is being evaluated in an ongoing clinical trial in patients with NSCLC (NCT01295827).

A number of other promising agents targeting the PD-1 pathway (PD-1 pathway inhibitors) are in clinical development (see Table 1.1 below):

TABLE 1.1

PD-1 pathway inhibitors in clinical development, besides pembrolizumab and nivolumab (taken from Table 1 of Harvey, Clinical Pharmacology & Therapeutics, 2014, Vol. 96(2), pages 214-223)

| Compound name | Description of molecule | Mechanism of action | Company |
|---|---|---|---|
| AMP-224 | Recombinant fusion protein: extracellular domain of PD-L2 and the Fc region of human IgG | Binds to PD-1; depletion of PD-1 high- expressing T cells (exhausted effector cells) | Amplimmune/ GlaxoSmithKline |
| BMS-936559 | High-affinity, fully human, PD-L1-specific, IgG4 monoclonal antibody | Blocks binding of PD-L1 to PD-1 and CD80 | Bristol-Myers Squibb |
| MEDI4736 | Fully human, high-affinity monoclonal anti-PD-L1 antibody | Blocks binding of PD-L1 to PD-1 and CD80 | MedImmune |
| MPDL3280A | Human anti-PD-L1 monoclonal antibody containing an engineered IgG Fc domain to prevent ADCC | Blocks binding of PD-L1 to PD-1 and CD80 | Roche/Genentech |
| Pidilizumab | Humanized anti-PD-1 IgG1 monoclonal antibody | Blocks binding of PD-1 to PD-L1 and PD-L2 | CureTech/Teva |

ADCC, antibody-dependent cell-mediated cytotoxicity; IgG, immunoglobulin G; PD-1, programmed death-1; PD-L1, PD ligand 1.

A further PD-1 pathway inhibitor in clinical development is Avelumab (also known as MSB0010718C), a fully human anti-PD-L1 IgG1 monoclonal antibody, under co-development by Merck KGaA and Pfizer.

Despite the recent FDA approval of Keytruda and Opdivo for the treatment of advanced melanoma, and promising results against NSCLC in clinical trials from agents targeting the PD-1 pathway, there remains a need to provide more effective cancer treatments, to provide treatments that are effective for a wider number of cancer patients, to provide effective treatments for other cancers, and to provide effective cancer treatments with reduced side effects.

The lymphocyte activation gene 3 (LAG-3) is a CD4 homolog type I membrane protein with four extracellular immunoglobulin superfamily domains. Similar to CD4, LAG-3 oligomerizes at the surfaces of T cells and binds to MHC class II molecules on antigen-presenting cells (APCs) but with significantly higher affinity than CD4. LAG-3 is expressed on activated $CD4^+$ and $CD8^+$ T lymphocytes where it associates with the CD3/T cell receptor complex at the cell surface and negatively regulates signal transduction. As a consequence, it negatively regulates T cell proliferation, function, and homeostasis. LAG-3 is upregulated on exhausted T cells compared with effector or memory T cells. LAG-3 is also upregulated on tumor infiltrating lymphocytes (TILs), and blockade of LAG-3 using anti-LAG-3 antibody can enhance anti-tumour T cell responses.

Blackburn et al (Nat Immunol. 2009; 10(1): 29-37) describe coregulation of $CD8^+$ T cell exhaustion during chronic viral infection by multiple inhibitory receptors. Using a mouse model of chronic lymphocytic choriomeningitis virus (LCMV), the authors demonstrate that exhausted antigen-specific $CD8^+$ T cells had increased expression of up to seven inhibitory receptors (PD-1, LAG3, 2B4, CD160, CTLA-4, PIR-B and GP49) compared to memory or naive $CD8^+$ T cells. Co-expression of multiple distinct inhibitory receptors was associated with greater T cell exhaustion and more severe infection. Blockade of the T cell inhibitory receptors PD-1 and LAG-3 (using anti-PD-L1 and anti-LAG-3 antibodies) improved T cell responses and diminished viral load in vivo.

Woo et al (Cancer Research 2011; 72(4): 917-927) describe co-expression of PD-1 and LAG-3 on tumor-infiltrating $CD4^+$ and $CD8^+$ T cells in transplantable tumors. Dual anti-LAG-3/anti-PD-1 antibody treatment cured most mice of established tumors that were largely resistant to single antibody treatment.

On the basis of the immunomodulatory role of LAG-3 on T cell function in chronic infection and cancer, the predicted mechanism of action for LAG-3-specific monoclonal antibodies is to inhibit the negative regulation of tumour-specific effector T cells.

LAG-3 also encodes an alternative splice variant that is translated to a soluble form of LAG-3 (sLAG-3). As a soluble molecule, LAG-3 activates antigen-presenting cells (APCs) through MHC class II signalling, leading to increased antigen-specific T-cell responses in vivo (Triebel, Trends Immunol., 2003, 24: 619-622).

The principal antitumor immune response is mediated through the activation of type 1 cytotoxic (Tc1) CD8 T cells, NK cells, and monocytes/macrophages. In short-term ex vivo assays, a soluble form of LAG-3 protein (IMP321) induces an appropriate cytotoxic-type response in peripheral blood mononuclear cells (PBMCs) (Brignone et al, Journal of Immunology, 2007, 179: 4202-4211). IMP321 binds to a minority of MHC class $II^+$ cells in PBMCs, including all myeloid dendritic cells, and a small fraction of monocytes. Four hours after addition of IMP321 to PBMCs, these myeloid cells produce TNF-$\alpha$ and CCL4. At 18 hours, 1% of $CD8^+$ T cells and 3.7% NK cells produce Tc1 cytokines such as IFN-$\alpha$ and/or TNF-$\alpha$. Early APC activation by IMP321 is needed for this Tc1-type activation because pure sorted $CD8^+$ T cells could not be activated by IMP321. Only antigen-experienced, fully differentiated granzyme+CD8 T cells (effector and effector memory but not naive or central memory T cells) are induced by IMP321 to full Tc1 activation.

It has now been found that a PD-1 pathway inhibitor (an anti-PD-1 antibody, or an anti-PD-L1 antibody) and a soluble derivative of LAG-3 (IMP321), acting as an APC activator, together synergistically activate T cells (in particular, $CD8^+$ T cells) in vitro.

This synergistic activation of T cells is surprising. In the dual anti-LAG-3/anti-PD-1 antibody treatment described by Woo et al (supra), the anti-LAG-3 antibody is believed to be inhibiting the negative regulation of tumour-specific effector T cells by LAG-3, whereas the soluble derivative of LAG-3 (IMP321) is believed to be acting through a different mechanism, as an APC activator.

BRIEF DESCRIPTION OF THE DRAWINGS

FIG. 15. Shows the amino acid sequence of mature human LAG-3 protein (SEQ ID NO.: 1). The four extracellular Ig superfamily domains are at amino acid residues: 1-149 (D1); 150-239 (D2); 240-330 (D3); and 331-412 (D4). The amino acid sequence of the extra-loop structure of the D1 domain of human LAG-3 protein is shown underlined in bold.

DETAILED DESCRIPTION

Figures 1A, 1B, 1C:
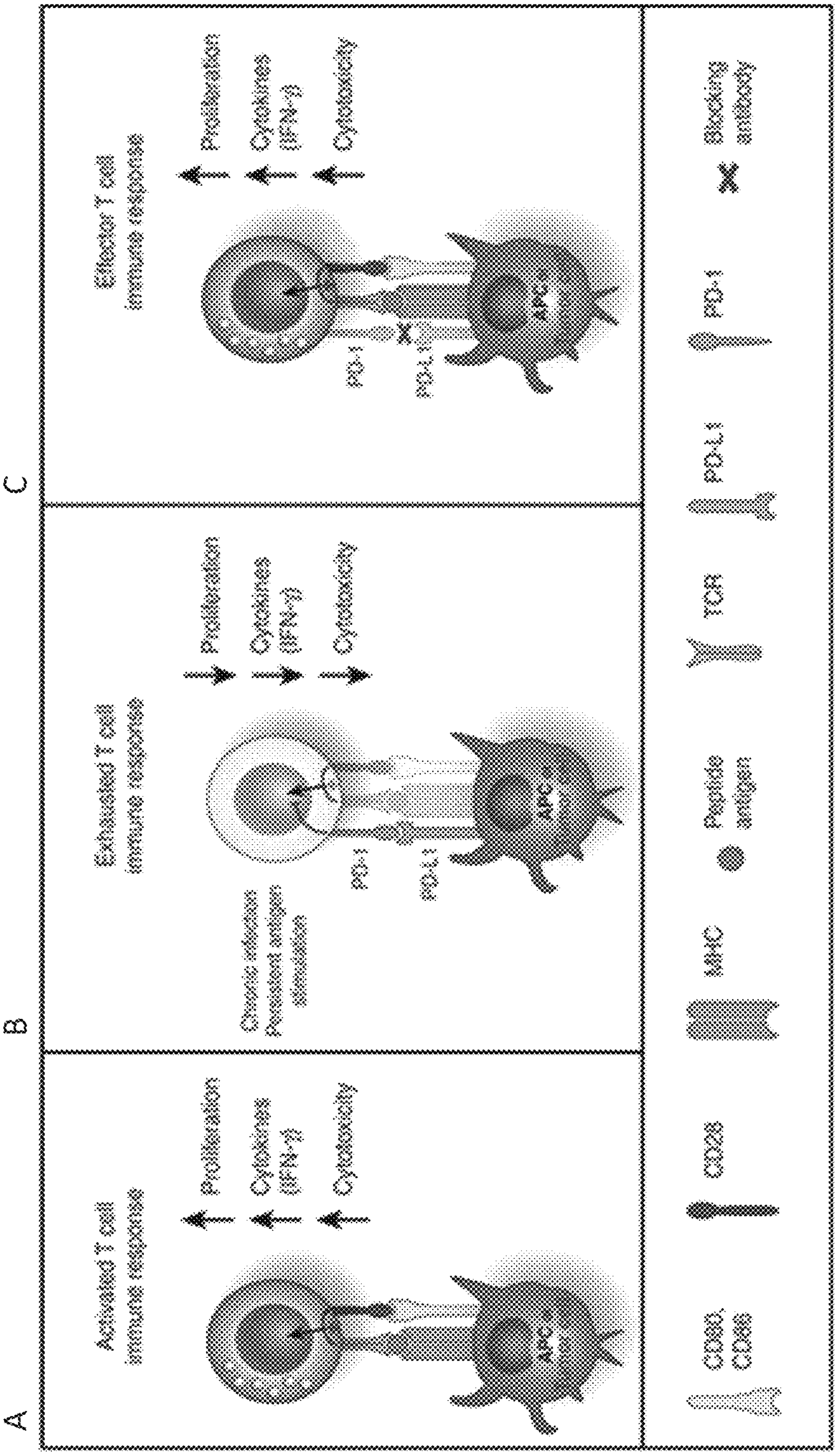
FIGS. 1A-1C. Depict the role of the PD-1 pathway in tumor immune evasion and the mechanism of action of PD-1 pathway blockade (APC, antigen-presenting cell; IFN-γ, interferon-γ; MHC, major histocompatibility complex; PD-1, programmed death-1; PD-L1, PD ligand 1; TCR, T-cell receptor). (A) Active T cell immune response, (B) Exhausted T cell immune response, (C) Effector T cell immune response.

According to the instant disclosure, there is provided a combined preparation, which comprises: (a) LAG-3 protein, or a derivative thereof that is able to bind to MHC class II molecules; and (b) a PD-1 pathway inhibitor.

The term "combined preparation" as used herein refers to a "kit of parts" in the sense that the combination components (a) and (b) as defined above can be dosed independently or by use of different fixed combinations with distinguished amounts of the combination components (a) and (b). The components can be administered simultaneously or one after the other. If the components are administered one after the other, preferably the time interval between administration is chosen such that the therapeutic effect of the combined use of the components is greater than the effect which would be obtained by use of only any one of the combination components (a) and (b).

The components of the combined preparation may be present in one combined unit dosage form, or as a first unit dosage form of component (a) and a separate, second unit dosage form of component (b). The ratio of the total amounts of the combination component (a) to the combination component (b) to be administered in the combined preparation can be varied, for example in order to cope with the needs of a patient sub-population to be treated, or the needs of the single patient, which can be due, for example, to the particular disease, age, sex, or body weight of the patient.

Preferably, there is at least one beneficial effect, for example an enhancing of the effect of the PD-1 pathway inhibitor, or an enhancing of the effect of the LAG-3 protein, or derivative thereof, or a mutual enhancing of the effect of the combination components (a) and (b), for example a more than additive effect, additional advantageous effects, fewer side effects, less toxicity, or a combined therapeutic effect compared with an effective dosage of one or both of the combination components (a) and (b), and very preferably a synergism of the combination components (a) and (b).

A combined preparation of the invention may be provided as a pharmaceutical combined preparation for administration to a mammal, preferably a human. The LAG-3 protein, or derivative thereof, may optionally be provided together with a pharmaceutically acceptable carrier, excipient, or diluent, and/or the PD-1 pathway inhibitor may optionally be provided together with a pharmaceutically acceptable carrier, excipient, or diluent.

The LAG-3, or derivative thereof, may be present at a dose which is a molar equivalent of 0.25-30 mg, 1-30 mg, or 6-30 mg of the LAG-3 derivative LAG-3Ig fusion protein IMP321. Doses of 6-30 mg per subcutaneous (s.c.) injection of IMP321 have been shown to be safe and provide an acceptable systemic exposure based on the results of pharmacokinetics data obtained in metastatic renal cell cancer patients. A blood concentration of IMP321 superior to 1 ng/ml for at least 24 hours after s.c. injection is obtained in patients injected with IMP321 doses of more than 6 mg.

A combined preparation of the invention may comprise a plurality of doses of the LAG-3 protein, or derivative thereof.

The PD-1 pathway inhibitor may be an agent that inhibits binding of PD-1 to PD-L1 and/or PD-L2. In particular, the agent may inhibit binding of human PD-1 to human PD-L1 and/or human PD-L2. The agent may inhibit binding of PD-1 to PD-L1 and/or PD-L2 by at least 50%, 60%, 70%, 80%, or 90%. Suitable assays for determining binding of PD-1 to PD-L1 or PD-L2, by Surface Plasmon Resonance (SPR) analysis, or flow cytometry analysis, are described in Ghiotto et al (Int. Immunol. August 2010; 22(8): 651-660). The agent may inhibit binding of PD-1 to PD-L1 and/or PD-L2, for example, by binding to PD-1, to PD-L1, or to PD-L2. The agent may be an antibody, suitably a monoclonal antibody, such as a human or humanized monoclonal antibody. The agent may be a fragment or derivative of an antibody that retains ability to inhibit binding of PD-1 to PD-L1 and/or PD-L2.

Examples of anti-PD-1 antibodies suitable for use according to the invention include: Pembrolizumab (MK-3475), a humanized monoclonal IgG4 antibody; Nivolumab, a fully human monoclonal IgG4 antibody; Pidilizumab (CT-011), a humanized IgG1 monoclonal antibody. An example of a PD-1 pathway inhibitor that binds to PD-1, but is not an antibody, is AMP-224. AMP-224 is a recombinant fusion protein of the extracellular domain of PD-L2 and the Fc region of human IgG. AMP-224 causes depletion of PD-1 high-expressing T cells. Examples of anti-PD-L1 antibodies suitable for use according to the invention include: BMS-936559, a fully human IgG4 monoclonal antibody; MEDI4736 (Durvalumab), a fully human, monoclonal antibody; MPDL3280A, a human monoclonal antibody containing an engineered IgG Fc domain to prevent ADCC; Avelumab (also known as MSB0010718C), a fully human anti-PD-L1 IgG1 monoclonal antibody.

The dose of the PD-1 pathway inhibitor will depend on the particular PD-1 pathway inhibitor being used. In general, a typically prescribed dose of a PD-1 pathway inhibitor for a human subject may be 0.1 to 10 mg/kg, for example 0.1 to 1 mg/kg, or 1 to 10 mg/kg. The term "typically prescribed dose" is used herein to include a dose which is the same as the dose, or within the dosage range, that is safe and therapeutically effective for administration to a subject (suitably a human subject) as a monotherapy, or that is approved by the appropriate regulatory authority for administration to a subject (suitably a human subject) as a monotherapy. Examples of typically prescribed human doses of known PD-1 pathway inhibitors when used as a monotherapy include:

Pembrolizumab (MK-3475): 2-10 mg/kg every two or three weeks. For example, the US FDA has approved administration of 2 mg/kg Keytruda (pembrolizumab) as an intravenous infusion over 30 minutes every 3 weeks;

Nivolumab: 0.1-10 mg/kg every two weeks. For example, the US FDA has approved administration of 3 mg/kg Opdivo (nivolumab) as an intravenous infusion over 60 minutes every 2 weeks;

BMS-936559: 0.3-10 mg/kg every two weeks.

The PD-1 pathway inhibitor may be administered by any suitable route, for example parenterally (including by subcutaneous, intravenous, or intramuscular injection). Currently approved or in-development PD-1 pathway inhibitors are administered as an intravenous infusion.

A combined preparation of the invention may comprise a plurality of doses of the PD-1 pathway inhibitor.

The LAG-3 protein may be an isolated natural or recombinant LAG-3 protein. The LAG-3 protein may comprise an amino sequence of LAG-3 protein from any suitable species, such as a primate or murine LAG-3 protein, but preferably a human LAG-3 protein. The amino acid sequence of human and murine LAG-3 protein is provided in FIG. 1 of Huard et al (*Proc. Natl. Acad. Sci. USA,* 11: 5744-5749, 1997). The sequence of human LAG-3 protein is repeated in FIG. 15 below (SEQ ID NO: 1). The amino acid sequences of the four extracellular Ig superfamily domains (D1, D2, D3, and D4) of human LAG-3 are also identified in FIG. 1 of Huard et al., at amino acid residues: 1-149 (D1); 150-239 (D2); 240-330 (D3); and 331-412 (D4).

Derivatives of LAG-3 protein include soluble fragments, variants, or mutants of LAG-3 protein that are able to bind MHC class II molecules. Several derivatives of LAG-3 protein are known that are able to bind to MHC class II molecules. Many examples of such derivatives are described in Huard et al (*Proc. Natl. Acad. Sci. USA,* 11: 5744-5749, 1997). This document describes characterization of the MHC class II binding site on LAG-3 protein. Methods for making mutants of LAG-3 are described, as well as a quantitative cellular adhesion assay for determining the ability of LAG-3 mutants to bind class II-positive Daudi cells. Binding of several different mutants of LAG-3 to MHC class II molecules was determined. Some mutations were able to reduce class II binding, while other mutations increased the affinity of LAG-3 for class II molecules. Many of the residues essential for binding MHC class II proteins are clustered at the base of a large 30 amino acid extra-loop structure in the LAG-3 D1 domain. The amino acid sequence of the extra-loop structure of the D1 domain of human LAG-3 protein is GPPAAAPGHPLAPGPHPAAPSSWGPRPRRY (SEQ ID NO: 2), the underlined sequence in FIG. 15.

The LAG-3 protein derivative may comprise the 30 amino acid extra-loop sequence of the human LAG-3 D1 domain, or a variant of such sequence with one or more conservative amino acid substitutions. The variant may comprise amino acid sequence that has at least 70%, 80%, 90%, or 95% amino acid identity with the 30 amino acid extra-loop sequence of the human LAG-3 D1 domain.

The derivative of LAG-3 protein may comprise an amino acid sequence of domain D1, and optionally domain D2, of LAG-3 protein, preferably human LAG-3 protein.

The derivative of LAG-3 protein may comprise an amino acid sequence that has at least 70%, 80%, 90%, or 95% amino acid identity with domain D1, or with domain D1 and D2, of LAG-3 protein, preferably human LAG-3 protein.

The derivative of LAG-3 protein may comprise an amino acid sequence of domains D1, D2, D3, and optionally D4, of LAG-3 protein, preferably human LAG-3 protein.

The derivative of LAG-3 protein may comprise an amino acid sequence that has at least 70%, 80%, 90%, or 95% amino acid identity with domain D1, D2, and D3, or with domain D1, D2, D3, and D4, of LAG-3 protein, preferably human LAG-3.

Sequence identity between amino acid sequences can be determined by comparing an alignment of the sequences. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

Suitable computer programs for carrying out sequence comparisons are widely available in the commercial and public sector. Examples include MatGat (Campanella et al., 2003, BMC Bioinformatics 4: 29; program available from matgat the bitincka website), Gap (Needleman & Wunsch, 1970, J. Mol. Biol. 48: 443-453), FASTA (Altschul et al., 1990, J. Mol. Biol. 215: 403-410; program available from the EBI FASTA website), Clustal W 2.0 and X 2.0 (Larkin et al., 2007, Bioinformatics 23: 2947-2948; program available from the EBI ClustalW2 website) and EMBOSS Pairwise Alignment Algorithms (Needleman & Wunsch, 1970, supra; Kruskal, 1983, In: Time warps, string edits and macromolecules: the theory and practice of sequence comparison, Sankoff & Kruskal (eds), pp 1-44, Addison Wesley; programs available from the EBI ALIGN website). All programs may be run using default parameters.

For example, sequence comparisons may be undertaken using the "needle" method of the EMBOSS Pairwise Alignment Algorithms, which determines an optimum alignment (including gaps) of two sequences when considered over their entire length and provides a percentage identity score. Default parameters for amino acid sequence comparisons ("Protein Molecule" option) may be Gap Extend penalty: 0.5, Gap Open penalty: 10.0, Matrix: Blosum 62.

The sequence comparison may be performed over the full length of the reference sequence.

The LAG-3 protein derivative may be fused to Immunoglobulin Fc amino acid sequence, preferably human IgG1 Fc amino acid sequence, optionally by a linker amino acid sequence.

The ability of a derivative of LAG-3 protein to bind to MHC class II molecules may be determined using a quantitative cellular adhesion assay as described in Huard et al (supra). The affinity of a derivative of LAG-3 protein for MHC class II molecules may be at least 20%, 30%, 40%, 50%, 60%, 70%, 80%, 90%, or 100% of the affinity of human LAG-3 protein for class II molecules. Preferably the affinity of a derivative of LAG-3 protein for MHC class II molecules is at least 50% of the affinity of human LAG-3 protein for class II molecules.

Examples of suitable derivatives of LAG-3 protein that are able to bind MHC class II molecules include derivatives comprising:

amino acid residues 23 to 448 of the human LAG-3 sequence;

amino acid sequence of domains D1 and D2 of LAG-3;

amino acid sequence of domains D1 and D2 of LAG-3 with an amino acid substitution at one or more of the following positions: position 73 where ARG is substituted with GLU; position 75 where ARG is substituted with ALA or GLU; position 76 where ARG is substituted with GLU; position 30 where ASP is substituted with ALA; position 56 where HIS is substituted with ALA; position 77 where TYR is substituted with PHE; position 88 where ARG is substituted with ALA; position 103 where ARG is substituted with ALA; position 109 where ASP is substituted with GLU; position 115 where ARG is substituted with ALA;

amino acid sequence of domain D1 of LAG-3 with a deletion of amino acid residues 54 to 66;

a recombinant soluble human LAG-3Ig fusion protein (IMP321)—a 200-kDa dimer produced in Chinese hamster ovary cells transfected with a plasmid encoding for the extracellular domain of hLAG-3 fused to the human IgG1 Fc. The sequence of IMP321 is given in SEQ ID NO: 17 of US 2011/0008331.

According to the invention there is also provided a pharmaceutical composition, which comprises (a) LAG-3 protein, or a derivative thereof that is able to bind to MHC class II molecules; (b) a PD-1 pathway inhibitor; and (c) a pharmaceutically acceptable carrier, excipient, or diluent.

According to the invention there is further provided a combined preparation, or pharmaceutical composition, of the invention for use as a medicament.

The invention also provides a combined preparation, or pharmaceutical composition, of the invention for preventing, treating, or ameliorating cancer.

There is further provided according to the invention use of a combined preparation, or pharmaceutical composition, of the invention in the manufacture of a medicament for preventing, treating, or ameliorating cancer.

There is also provided according to the invention a method of preventing, treating, or ameliorating cancer, which comprises administering LAG-3 protein, or a derivative thereof that is able to bind to MHC class II molecules, and a PD-1 pathway inhibitor, to a subject in need of such prevention, treatment, or amelioration.

We have appreciated that combined preparations and compositions of the invention may also be used for the prevention, treatment, or amelioration of infection, in particular chronic or persistent infection.

During acute infection, activated pathogen-specific cytotoxic CD8 T lymphocytes (CTLs) proliferate and acquire effector functions, such as cytokine production and cytotoxic capability, which enable them to effectively clear infection. Following clearance, a small pool of pathogen-specific memory T cells remain that have the ability to very rapidly reactivate and acquire their killing functions following re-exposure to the same pathogen. However, during chronic infection this does not occur, as pathogen-specific CTLs are found to be functionally deficient and unable to eliminate infection. These exhausted CTLs are defined by their impaired proliferative capacity, cytokine production and loss of cytotoxic capabilities (see FIG. 1(*b*), and review of Hofmeyer et al., Journal of Biomedicine and Biotechnology, Volume 2011, Article ID 451694).

This phenomenon was originally defined using a well-established mouse model of chronic viral infection in mice, lymphocytic choriomeningitis virus (LCMV) (Zajac, et al., The Journal of Experimental Medicine, vol. 188, no. 12, pp.

2205-2213, 1998; Gallimore, et al., The Journal of Experimental Medicine, vol. 187, no. 9, pp. 1383-1393, 1998.). The Armstrong strain of LCMV causes an acute infection that is cleared by the immune system, generating a robust CTL memory. On the other hand, the Clone 13 strain of LCMV establishes a chronic infection in mice that renders CTLs exhausted and unable to clear infection. Additionally, as compared to normal T cells, exhausted CTLs have metabolic deficiencies and altered expression of genes involved in chemotaxis, adhesion, and migration (Wherry, et al., Immunity, vol. 27, no. 4, pp. 670-684, 2007).

In a study conducted to reveal mechanisms that lead to exhaustion, the genetic profile of exhausted CTLs from a chronic LMCV infection was compared to that of functional CTLs responding to an acute LCMV infection (Barber, et al., Nature, vol. 439, no. 7077, pp. 682-687, 2006). Exhausted CTLs were found to have significant overexpression of PD-1, whereas the functional LCMV-specific CTLs had no appreciable expression of PD-1. Expression of PD-1 was found to correlate with the defined functional impairment seen in exhausted T cells and, in turn, higher viral loads. Blocking the PD-1/PD-L1 pathway, with an anti-PD-L1 antibody, in chronically infected mice resulted in enhanced CTL response that caused a decrease in viral loads. PD-1 expression by exhausted CTLs is dependent on persisting antigen-specific stimulation, as loss of presentation of specific epitope during chronic infection leads to functional restoration and decreased PD-1 expression on epitope-specific CTLs (Blattman, et al., Journal of Virology, vol. 83, no. 9, pp. 4386-4394, 2009). Persistent antigen stimulation during chronic viral infection has a progressive effect on loss of CTL function and correlated increase in PD-1 expression, meaning that more exhausted CTLs (PD-1h$^{hi}$) are less susceptible to functional rescue by PD-1 blocking than others (PD-1$^{int}$) (Blackburn, et al., Proceedings of the National Academy of Sciences of the United States of America, vol. 105, no. 39, pp. 15016-15021, 2008).

According to the invention, there is further provided a combined preparation, or pharmaceutical composition, of the invention for use in preventing, treating, or ameliorating an infection.

There is also provided according to the invention use of a combined preparation, or pharmaceutical composition, of the invention in the manufacture of a medicament for preventing, treating, or ameliorating an infection.

There is also provided according to the invention a method of preventing, treating, or ameliorating an infection, which comprises administering LAG-3 protein, or a derivative thereof that is able to bind to MHC class II molecules, and a PD-1 pathway inhibitor, to a subject in need of such prevention, treatment, or amelioration.

In particular embodiments, the infection is a chronic or persistent infection. The term "chronic or persistent infection" is used herein to refer to an infection by a pathogen that has induced a classical CTL response in an infected subject, but the infection has not been cleared, resulting in the presence of exhausted PD-1-expressing, pathogen-specific CTLs with impaired proliferative capacity, cytokine production and loss of cytotoxic capabilities.

Examples of infections that may be treated according to the invention include viral, bacterial, fungal, or protozoan infections, especially chronic or persistent viral, bacterial, fungal, or protozoan infections.

The viral infection may be caused by, for example, an adenovirus, an adeno-associated virus, a B virus (macacine herpesvirus I), a BK virus, a bunyavirus, a chikungunya virus, a cocksackie virus, a coronavirus, a cytomegalovirus, an eastern equine encephalitis virus, an ebola virus, an enterovirus, an Epstein-Barr virus, a hantavirus, a hepatitis A virus, a hepatitis B virus, a hepatitis C virus, a hepatitis D virus, a hepatitis E virus, a herpes virus, a herpes simplex virus 1, a herpes simplex virus 2, a human foamy virus, a human herpes virus 3, a human herpes virus 5, a human herpes virus 6, a human herpes virus 7, a human immunodeficiency virus, a human papillomavirus, a human β-lymphotropic virus, a human T-cell leukemia virus I, a human T-cell leukemia virus II, an influenza virus, a JC virus, a JEV, a Kaposi's sarcoma-associated herpesvirus, a Lassa virus, a lymphocytic choriomeningitis virus, a Marburg virus, a measles virus, a mumps virus, a Nipah virus, a norovirus, a Norwalk virus, an orthoreovirus, a parainfluenza virus, a parvovirus, a poliovirus, a rabies virus, a reovirus, a respiratory syncytial virus, rhinovirus, a Rift Valley fever virus, a rotavirus, rubella virus, a smallpox virus, a St Louis encephalitis virus, a variola major virus, a variola minor virus, a vericella-zoster virus, a West Nile virus, a western equine encephalitis virus, or a yellow fever virus).

In particular embodiments, the viral infection is caused by a hepatitis virus (for example, a hepatitis B virus, a hepatitis C virus), a lentivirus (for example, a human immunodeficiency virus), or a herpes virus (for example, a herpes simplex virus 1, a herpes simplex virus 2).

The bacterial infection may be caused by, for example, *Escherichia coli, Clostridium difficile, Salmonella thyphimurium, Pseudomonas aeruginosa, Vibrio cholerae, Neisseria gonorrhoeae, Helicobacter pylori, Hemophilus influenzae, Shigella dysenteriae, Staphylococcus aureus, Mycobacterium tuberculosis, Streptococcus pneumonia*, or *Chlamydia trachomatis*.

The fungal infection may be caused by, for example, *Candida, Aspergillus, Cryptococcus, Coccidioides, Histoplasma, Pneumocystis*, or Stachybotrys.

The protozoan infection may be caused by, for example, *Amoebozoa, Excavata, Chromalveolata, Entamoeba, Plasmodium, Giardia, Trypanosoma, Coccidia, Besnoitia, Dicrocoelium*, or *Leishmania*.

There is further provided according to the invention a combined preparation, or pharmaceutical composition, of the invention for use in preventing, treating, or ameliorating a disease, disorder, or condition that can be prevented, treated, or ameliorated by activation of T cells, in particular by activation of CD8-positive T cells.

There is also provided according to the invention use of a combined preparation, or pharmaceutical composition, of the invention in the manufacture of a medicament for preventing, treating, or ameliorating a disease, disorder, or condition that can be prevented, treated, or ameliorated by activation of T cells, in particular by activation of CD8-positive T cells.

There is also provided according to the invention a method of preventing, treating, or ameliorating a disease, disorder, or condition that can be prevented, treated, or ameliorated by activation of T cells, in particular by activation of CD8-positive T cells, which comprises administering LAG-3 protein, or a derivative thereof that is able to bind to MHC class II molecules, and a PD-1 pathway inhibitor, to a subject in need of such prevention, treatment, or amelioration.

In some embodiments, the disease, disorder, or condition that can be prevented, treated, or ameliorated by activation of T cells may exclude cancer.

There is also provided according to the invention a combined preparation, or pharmaceutical composition, of the invention for use in enhancing a T cell-mediated immune response, in particular a CD8-positive T cell-mediated immune response.

The invention also provides use of a combined preparation, or pharmaceutical composition, of the invention in the manufacture of a medicament for enhancing a T cell-mediated immune response, in particular a CD8-positive T cell-mediated immune response.

According to the invention there is further provided a method of enhancing a T cell-mediated immune response, in particular a CD8-positive T cell-mediated immune response, which comprises administering LAG-3 protein, or a derivative thereof that is able to bind to MHC class II molecules, and a PD-1 pathway inhibitor, to a subject in need of such enhanced T cell-mediated immune response.

In some embodiments, enhancement of the T cell-mediated immune response, or CD8-positive T cell-mediated immune response, may exclude the prevention, treatment, or amelioration of cancer.

The LAG-3 protein, or derivative thereof, and the PD-1 pathway inhibitor may be administered sequentially to the subject, i.e. the LAG-3 protein, or derivative thereof, may be administered before, with, or after the PD-1 pathway inhibitor.

The LAG-3 protein, or derivative thereof, and the PD-1 pathway inhibitor may be administered to the subject within 96 hours, 72 hours, 48 hours, 24 hours, or 12 hours, of each other.

Alternatively, the LAG-3 protein, or derivative thereof, and the PD-1 pathway inhibitor may be co-administered to the subject, for example as a composition comprising the LAG-3 protein, or derivative thereof, and the PD-1 pathway inhibitor, or by simultaneous administration of separate doses of the LAG-3 protein, or derivative thereof, and the PD-1 pathway inhibitor.

According to some embodiments, a plurality of doses of the LAG-3 protein, or derivative thereof, and/or a plurality of doses of the PD-1 pathway inhibitor, is administered to the subject.

According to some embodiments, a dose of the LAG-3 protein, or derivative thereof, is administered before, with, or after each administration of two or more doses of the PD-1 pathway inhibitor.

For example, a dose of the LAG-3 protein, or derivative thereof, may be administered within 96 hours, 72 hours, 48 hours, 24 hours, or 12 hours, of each administration of two or more doses of the PD-1 pathway inhibitor.

The choice of appropriate dosages of the components used in combination therapy according to the present invention can be determined and optimized by the skilled person, for example, by observation of the patient, including the patient's overall health, and the response to the combination therapy. Optimization, for example, may be necessary if it is determined that a patient is not exhibiting the desired therapeutic effect or conversely, if the patient is experiencing undesirable or adverse side effects that are too many in number or are of a troublesome severity.

The doses of the components used in combination therapy according to the invention should be chosen to provide a therapeutically effective amount of the components in combination.

An "effective amount" of the combination therapy may be an amount that results in a reduction of at least one pathological parameter associated with cancer. For example, in some embodiments, an effective amount of the combination therapy is an amount that is effective to achieve a reduction of at least about 10%, 20%, 30%, 40%, 50%, 60%, 70%, 80%, or 90%, in the pathological parameter, compared to the expected reduction in the parameter associated with the cancer without the combination therapy. For example, the pathological parameter may be tumor growth, or tumor growth rate.

Alternatively, an "effective amount" of the combination therapy may be an amount that results in an increase in a clinical benefit associated with cancer treatment. For example, in some embodiments, an "effective amount" of the combination therapy is an amount that is effective to achieve an increase of at least about 10%, 20%, 30%, 40%, 50%, 60%, 70%, 80%, or 90%, in the clinical benefit, compared to the expected clinical benefit without the combination therapy. For example, the clinical benefit may be tumor response rate, progression-free survival, overall survival, or increased sensitization to subsequent treatments.

Alternatively, an "effective amount" of the combination therapy may be an amount that results in a change of at least one beneficial parameter relating to cancer treatment. For example, in some embodiments, an "effective amount" of the combination therapy is an amount that is effective to achieve a change of at least about 10%, 20%, 30%, 40%, 50%, 60%, 70%, 80%, or 90%, in the parameter, compared to the expected change in the parameter relating to cancer treatment without the combination therapy. For example, the parameter may be an increase in the number of circulating tumor antigen-specific $CD8^+$ T cells, or a reduction in the number of tumor antigen-specific regulatory T cells, or an increase in the number of activated T cells, in particular activated $CD8^+$ T cells, a reduction in the number of exhausted antigen-specific $CD8^+$ T cells, or an increase in the number of circulating functional (i.e. non-exhausted) antigen-specific $CD8^+$ T cells.

In embodiments relating to treatment of infection, an "effective amount" of the combination therapy may be an amount that results in a reduction of at least one pathological parameter associated with infection. For example, in some embodiments, an effective amount of the combination therapy is an amount that is effective to achieve a reduction of at least about 10%, 20%, 30%, 40%, 50%, 60%, 70%, 80%, or 90%, in the pathological parameter, compared to the expected reduction in the parameter associated with the infection without the combination therapy. For example, the pathological parameter may be viral load (for example, the number of viral particles or amount of viral DNA per ml of blood), bacterial load (for example, the amount of bacterial DNA per ml of blood, or the number of bacterial colonies after a 1-21 day growth period on different agar plates).

Suitable methods of measuring viral and bacterial load are well-known to those of ordinary skill in the art. For example, methods of measuring viral load by ELISA are compared in Goldschmidt et al. (Clinical and Diagnostic Laboratory Immunology, July 1998, p. 513-518). Methods of measuring viral load using different commercial assays for detection of viral nucleic acid are compared in Holguin et al. (Eur J Clin Microbiol Infect Dis. 1999 April; 18(4):256-9) and Swenson et al. (J. Clin. Microbiol. 2014 February; 52(2): 517-523). An example of a paper describing measurement of bacterial load by real-time PCR is Nadkarni et al. (Microbiology (2002), 148, 257-266). This paper cites Bergey's Manual of Determinative Bacteriology, now superseded by Bergey's Manual of Systematic Bacteriology, $2^{nd}$ Edition. A molecular bacterial load assay is described by Honeyborne et al. (J. Clin. Microbiol. 2011 49:3905-3911, and J. Clin. Microbiol. 2014 August; 52(8):3064-7). A list of FDA-approved screening assays to measure viral and bacterial loads can be found on the FDA website.

Alternatively, an "effective amount" of the combination therapy may be an amount that results in an increase in a clinical benefit associated with treatment of infection. For example, in some embodiments, an "effective amount" of the combination therapy is an amount that is effective to achieve an increase of at least about 10%, 20%, 30%, 40%, 50%, 60%, 70%, 80%, or 90%, in the clinical benefit, compared to the expected clinical benefit without the combination therapy.

Alternatively, an "effective amount" of the combination therapy may be an amount that results in a change of at least one beneficial parameter relating to treatment of infection. For example, in some embodiments, an "effective amount" of the combination therapy is an amount that is effective to achieve a change of at least about 10%, 20%, 30%, 40%, 50%, 60%, 70%, 80%, or 90%, in the parameter, compared to the expected change in the parameter relating to treatment without the combination therapy. For example, the parameter may be an increase in the number of activated T cells, in particular activated $CD8^+$ T cells, an increase in the number of circulating functional (i.e. non-exhausted) antigen-specific $CD8^+$ T cells, or a reduction in the number of exhausted antigen-specific $CD8^+$ T cells, or a reduction in the number of antigen-specific regulatory T cells.

According to the invention, combination treatment may be employed to increase the therapeutic effect of the PD-1 pathway inhibitor, or LAG-3 protein, or derivative thereof, compared with the effect of the PD-1 pathway inhibitor, or LAG-3 protein, or derivative thereof, as a monotherapy, or to decrease the doses of the individual components in the resulting combinations while preventing or further reducing the risk of unwanted or harmful side effects of the individual components.

In one embodiment, the LAG-3 protein, or derivative thereof, and the PD-1 pathway inhibitor are each prescribed at a dose that is within a typically prescribed dose range for each compound as a monotherapy. The compounds may be prescribed as separate dosages or as a combination dosage. Such combinations provide increased efficacy compared with the effect of either compound as a monotherapy.

In another embodiment, the LAG-3 protein, or derivative thereof, and the PD-1 pathway inhibitor are each prescribed at a dose that is below a typically prescribed dose for each component as a monotherapy, but at doses that have therapeutic efficacy in combination. The components may be prescribed as separate dosages or as a combination dosage. The dosages of the components in combination may be selected to provide a similar level of therapeutic efficacy as the LAG-3 protein, or derivative thereof, or the PD-1 pathway inhibitor as a monotherapy, but with the advantage that the lower doses of the LAG-3 protein, or derivative thereof, and the PD-1 pathway inhibitor reduce the risk of adverse side effects compared to the prescribed dosages of each compound as a monotherapy.

In another embodiment, the prescribed dosage of the PD-1 pathway inhibitor is within a typically prescribed dose range for monotherapy, and the LAG-3 protein, or derivative thereof, is prescribed at a dosage that is below a typically prescribed dose for monotherapy.

In a further embodiment, the prescribed dosage of the PD-1 pathway inhibitor is below a typically prescribed dose for monotherapy, and the LAG-3 protein, or derivative thereof, is prescribed at a dosage that is within a typically prescribed dose range for monotherapy.

Preferred dosages below the typically prescribed dose for monotherapy are doses that are up to 50%, or up to 25%, of the typically prescribed dose. For example, dosages below the typically prescribed dose for monotherapy may be doses that are 1-50%, 1-25%, 1-10%, 2-50%, 2-25%, 2-10%, of the typically prescribed dose of the PD-1 pathway inhibitor and/or the LAG-3 protein, or derivative thereof.

A typically prescribed dose of a LAG-3 protein, or derivative thereof, for monotherapy in a human subject may be a dose that is molar equivalent of 0.25-30 mg, 1-30 mg, or 6-30 mg of the LAG-3 derivative LAG-3Ig fusion protein IMP321.

A typically prescribed dose of a PD-1 pathway inhibitor for monotherapy in a human subject may be 0.1 to 10 mg/kg, 0.1 to 1 mg/kg, or 1 to 10 mg/kg. For example, a typically prescribed dose of pembrolizumab for monotherapy in a human subject may be 2-10 mg/kg, for example 2 mg/kg, a typically prescribed dose of nivolumab for monotherapy in a human subject may be 0.1-10 mg/kg, for example 3 mg/kg, and a typically prescribed dose of BMS-936559 for monotherapy in a human subject may be 0.3-10 mg/kg.

In particular embodiments of combined preparations or compositions of the invention, the prescribed dosage of the PD-1 pathway inhibitor is below a typically prescribed dose for monotherapy, for example 1-50%, 1-25%, 1-20%, 1-10%, 2-50%, 2-25%, 2-20%, 2-10%, 0.1-50%, 0.1-25%, 0.1-20%, 0.1-10%, <20%, <10%, 0.1-<20%, 0.1-<10%, 0.01-<20%, or 0.01-<10% of the typically prescribed dose of the PD-1 pathway inhibitor.

Examples of suitable doses of the PD-1 pathway inhibitor and LAG-3 protein, or derivative thereof, according to the invention, are set out in Table 1.2 below:

TABLE 1.2

Examples of doses of the PD-1 pathway inhibitor and LAG-3 protein or derivative thereof, according to embodiments of combined preparations or compositions of the invention

| Type of PD-1 pathway inhibitor | Dose of PD-1 pathway inhibitor: mg/kg [mg dose for 70 kg human] | Human dose of LAG-3 protein or derivative thereof (given as a mg dose of IMP321, or a molar equivalent thereof) |
|---|---|---|
| Anti-PD-1 antibody or anti-PD-L1 antibody | 0.001-5 mg/kg [0.07-350 mg] | 0.25-30 mg |
| | 0.001-2.5 mg/kg [0.07-175 mg] | 0.25-30 mg |
| | 0.001-1 mg/kg [0.07-70 mg] | 0.25-30 mg |
| | 0.001-<1 mg/kg [0.07-<70 mg] | 0.25-30 mg |
| | 0.001-0.5 mg/kg [0.07-35 mg] | 0.25-30 mg |
| | 0.001-0.1 mg/kg [0.07-7 mg] | 0.25-30 mg |
| | 0.002-5 mg/kg [0.14-350 mg] | 0.25-30 mg |
| | 0.002-2.5 mg/kg [0.14-175 mg] | 0.25-30 mg |
| | 0.002-1 mg/kg [0.14-70 mg] | 0.25-30 mg |

TABLE 1.2-continued

Examples of doses of the PD-1 pathway inhibitor and LAG-3 protein or derivative thereof, according to embodiments of combined preparations or compositions of the invention

| Type of PD-1 pathway inhibitor | Dose of PD-1 pathway inhibitor: mg/kg [mg dose for 70 kg human] | Human dose of LAG-3 protein or derivative thereof (given as a mg dose of IMP321, or a molar equivalent thereof) |
|---|---|---|
| | 0.002-<1 mg/kg [0.14-<70 mg] | 0.25-30 mg |
| | 0.002-0.5 mg/kg [0.14-35 mg] | 0.25-30 mg |
| | 0.002-0.1 mg/kg [0.14-7 mg] | 0.25-30 mg |
| Anti-PD-1 antibody or anti-PD-L1 antibody | 0.001-5 mg/kg [0.07-350 mg] | 1-30 mg |
| | 0.001-2.5 mg/kg [0.07-175 mg] | 1-30 mg |
| | 0.001-1 mg/kg [0.07-70 mg] | 1-30 mg |
| | 0.001-<1 mg/kg [0.07-<70 mg] | 1-30 mg |
| | 0.001-0.5 mg/kg [0.07-35 mg] | 1-30 mg |
| | 0.001-0.1 mg/kg [0.07-7 mg] | 1-30 mg |
| | 0.002-5 mg/kg [0.14-350 mg] | 1-30 mg |
| | 0.002-2.5 mg/kg [0.14-175 mg] | 1-30 mg |
| | 0.002-1 mg/kg [0.14-70 mg] | 1-30 mg |
| | 0.002-<1 mg/kg [0.14-<70 mg] | 1-30 mg |
| | 0.002-0.5 mg/kg [0.14-35 mg] | 1-30 mg |
| | 0.002-0.1 mg/kg [0.14-7 mg] | 1-30 mg |
| Anti-PD-1 antibody or anti-PD-L1 antibody | 0.001-5 mg/kg [0.07-350 mg] | 6-30 mg |
| | 0.001-2.5 mg/kg [0.07-175 mg] | 6-30 mg |
| | 0.001-1 mg/kg [0.07-70 mg] | 6-30 mg |
| | 0.001-<1 mg/kg [0.07-<70 mg] | 6-30 mg |
| | 0.001-0.5 mg/kg [0.07-35 mg] | 6-30 mg |
| | 0.001-0.1 mg/kg [0.07-7 mg] | 6-30 mg |
| | 0.002-5 mg/kg [0.14-350 mg] | 6-30 mg |
| | 0.002-2.5 mg/kg [0.14-175 mg] | 6-30 mg |
| | 0.002-1 mg/kg [0.14-70 mg] | 6-30 mg |
| | 0.002-<1 mg/kg [0.14-<70 mg] | 6-30 mg |
| | 0.002-0.5 mg/kg [0.14-35 mg] | 6-30 mg |
| | 0.002-0.1 mg/kg [0.14-7 mg] | 6-30 mg |
| Pembrolizumab | 0.001-5 mg/kg [0.07-350 mg] | 0.25-30 mg |
| | 0.001-2.5 mg/kg [0.07-175 mg] | 0.25-30 mg |
| | 0.001-1 mg/kg [0.07-70 mg] | 0.25-30 mg |
| | 0.001-<1 mg/kg [0.07-<70 mg] | 0.25-30 mg |
| | 0.001-0.5 mg/kg [0.07-35 mg] | 0.25-30 mg |
| | 0.001-0.1 mg/kg [0.07-7 mg] | 0.25-30 mg |
| | 0.002-5 mg/kg [0.14-350 mg] | 0.25-30 mg |
| | 0.002-2.5 mg/kg [0.14-175 mg] | 0.25-30 mg |
| | 0.002-1 mg/kg [0.14-70 mg] | 0.25-30 mg |
| | 0.002-<1 mg/kg [0.14-<70 mg] | 0.25-30 mg |
| | 0.002-0.5 mg/kg [0.14-35 mg] | 0.25-30 mg |
| | 0.002-0.1 mg/kg [0.14-7 mg] | 0.25-30 mg |
| Pembrolizumab | 0.001-5 mg/kg [0.07-350 mg] | 1-30 mg |
| | 0.001-2.5 mg/kg [0.07-175 mg] | 1-30 mg |
| | 0.001-1 mg/kg [0.07-70 mg] | 1-30 mg |
| | 0.001-<1 mg/kg [0.07-<70 mg] | 1-30 mg |
| | 0.001-0.5 mg/kg [0.07-35 mg] | 1-30 mg |
| | 0.001-0.1 mg/kg [0.07-7 mg] | 1-30 mg |
| | 0.002-5 mg/kg [0.14-350 mg] | 1-30 mg |
| | 0.002-2.5 mg/kg [0.14-175 mg] | 1-30 mg |
| | 0.002-1 mg/kg [0.14-70 mg] | 1-30 mg |
| | 0.002-1 mg/kg [0.14-70 mg] | 1-30 mg |
| | 0.002-<1 mg/kg [0.14-<70 mg] | 1-30 mg |
| | 0.002-0.5 mg/kg [0.14-35 mg] | 1-30 mg |
| Pembrolizumab | 0.001-5 mg/kg [0.07-350 mg] | 6-30 mg |
| | 0.001-2.5 mg/kg [0.07-175 mg] | 6-30 mg |
| | 0.001-1 mg/kg [0.07-70 mg] | 6-30 mg |
| | 0.001-<1 mg/kg [0.07-<70 mg] | 6-30 mg |
| | 0.001-0.5 mg/kg [0.07-35 mg] | 6-30 mg |
| | 0.001-0.1 mg/kg [0.07-7 mg] | 6-30 mg |
| | 0.002-5 mg/kg [0.14-350 mg] | 6-30 mg |
| | 0.002-2.5 mg/kg [0.14-175 mg] | 6-30 mg |
| | 0.002-1 mg/kg [0.14-70 mg] | 6-30 mg |
| | 0.002-<1 mg/kg [0.14-<70 mg] | 6-30 mg |
| | 0.002-0.5 mg/kg [0.14-35 mg] | 6-30 mg |
| | 0.002-0.1 mg/kg [0.14-7 mg] | 6-30 mg |
| Nivolumab | 0.001-5 mg/kg [0.07-350 mg] | 0.25-30 mg |
| | 0.001-2.5 mg/kg [0.07-175 mg] | 0.25-30 mg |
| | 0.001-1 mg/kg [0.07-70 mg] | 0.25-30 mg |
| | 0.001-<1 mg/kg [0.07-<70 mg] | 0.25-30 mg |
| | 0.001-0.5 mg/kg [0.07-35 mg] | 0.25-30 mg |
| | 0.001-0.1 mg/kg [0.07-7 mg] | 0.25-30 mg |
| | 0.002-5 mg/kg [0.14-350 mg] | 0.25-30 mg |

TABLE 1.2-continued

Examples of doses of the PD-1 pathway inhibitor and LAG-3 protein or derivative thereof, according to embodiments of combined preparations or compositions of the invention

| Type of PD-1 pathway inhibitor | Dose of PD-1 pathway inhibitor: mg/kg [mg dose for 70 kg human] | Human dose of LAG-3 protein or derivative thereof (given as a mg dose of IMP321, or a molar equivalent thereof) |
|---|---|---|
| | 0.002-2.5 mg/kg [0.14-175 mg] | 0.25-30 mg |
| | 0.002-1 mg/kg [0.14-70 mg] | 0.25-30 mg |
| | 0.002-<1 mg/kg [0.14-<70 mg] | 0.25-30 mg |
| | 0.002-0.5 mg/kg [0.14-35 mg] | 0.25-30 mg |
| | 0.002-0.1 mg/kg [0.14-7 mg] | 0.25-30 mg |
| Nivolumab | 0.001-5 mg/kg [0.07-350 mg] | 1-30 mg |
| | 0.001-2.5 mg/kg [0.07-175 mg] | 1-30 mg |
| | 0.001-1 mg/kg [0.07-70 mg] | 1-30 mg |
| | 0.001-<1 mg/kg [0.07-<70 mg] | 1-30 mg |
| | 0.001-0.5 mg/kg [0.07-35 mg] | 1-30 mg |
| | 0.001-0.1 mg/kg [0.07-7 mg] | 1-30 mg |
| | 0.002-5 mg/kg [0.14-350 mg] | 1-30 mg |
| | 0.002-2.5 mg/kg [0.14-175 mg] | 1-30 mg |
| | 0.002-1 mg/kg [0.14-70 mg] | 1-30 mg |
| | 0.002-<1 mg/kg [0.14-<70 mg] | 1-30 mg |
| | 0.002-0.5 mg/kg [0.14-35 mg] | 1-30 mg |
| | 0.002-0.1 mg/kg [0.14-7 mg] | 1-30 mg |
| Nivolumab | 0.001-5 mg/kg [0.07-350 mg] | 6-30 mg |
| | 0.001-2.5 mg/kg [0.07-175 mg] | 6-30 mg |
| | 0.001-1 mg/kg [0.07-70 mg] | 6-30 mg |
| | 0.001-<1 mg/kg [0.07-<70 mg] | 6-30 mg |
| | 0.001-0.5 mg/kg [0.07-35 mg] | 6-30 mg |
| | 0.001-0.1 mg/kg [0.07-7 mg] | 6-30 mg |
| | 0.002-5 mg/kg [0.14-350 mg] | 6-30 mg |
| | 0.002-2.5 mg/kg [0.14-175 mg] | 6-30 mg |
| | 0.002-1 mg/kg [0.14-70 mg] | 6-30 mg |
| | 0.002-<1 mg/kg [0.14-<70 mg] | 6-30 mg |
| | 0.002-0.5 mg/kg [0.14-35 mg] | 6-30 mg |
| | 0.002-0.1 mg/kg [0.14-7 mg] | 6-30 mg |
| BMS-936559 | 0.001-5 mg/kg [0.07-350 mg] | 0.25-30 mg |
| | 0.001-2.5 mg/kg [0.07-175 mg] | 0.25-30 mg |
| | 0.001-1 mg/kg [0.07-70 mg] | 0.25-30 mg |
| | 0.001-<1 mg/kg [0.07-<70 mg] | 0.25-30 mg |
| | 0.001-0.5 mg/kg [0.07-35 mg] | 0.25-30 mg |
| | 0.001-0.1 mg/kg [0.07-7 mg] | 0.25-30 mg |
| | 0.002-5 mg/kg [0.14-350 mg] | 0.25-30 mg |
| | 0.002-2.5 mg/kg [0.14-175 mg] | 0.25-30 mg |
| | 0.002-1 mg/kg [0.14-70 mg] | 0.25-30 mg |
| | 0.002-<1 mg/kg [0.14-<70 mg] | 0.25-30 mg |
| | 0.002-0.5 mg/kg [0.14-35 mg] | 0.25-30 mg |
| | 0.002-0.1 mg/kg [0.14-7 mg] | 0.25-30 mg |
| BMS-936559 | 0.001-5 mg/kg [0.07-350 mg] | 1-30 mg |
| | 0.001-2.5 mg/kg [0.07-175 mg] | 1-30 mg |
| | 0.001-1 mg/kg [0.07-70 mg] | 1-30 mg |
| | 0.001-<1 mg/kg [0.07-<70 mg] | 1-30 mg |
| | 0.001-0.5 mg/kg [0.07-35 mg] | 1-30 mg |
| | 0.001-0.1 mg/kg [0.07-7 mg] | 1-30 mg |
| | 0.002-5 mg/kg [0.14-350 mg] | 1-30 mg |
| | 0.002-2.5 mg/kg [0.14-175 mg] | 1-30 mg |
| | 0.002-1 mg/kg [0.14-70 mg] | 1-30 mg |
| | 0.002-<1 mg/kg [0.14-<70 mg] | 1-30 mg |
| | 0.002-0.5 mg/kg [0.14-35 mg] | 1-30 mg |
| | 0.002-0.1 mg/kg [0.14-7 mg] | 1-30 mg |
| BMS-936559 | 0.001-5 mg/kg [0.07-350 mg] | 6-30 mg |
| | 0.001-2.5 mg/kg [0.07-175 mg] | 6-30 mg |
| | 0.001-1 mg/kg [0.07-70 mg] | 6-30 mg |
| | 0.001-<1 mg/kg [0.07-<70 mg] | 6-30 mg |
| | 0.001-0.5 mg/kg [0.07-35 mg] | 6-30 mg |
| | 0.001-0.1 mg/kg [0.07-7 mg] | 6-30 mg |
| | 0.002-5 mg/kg [0.14-350 mg] | 6-30 mg |
| | 0.002-2.5 mg/kg [0.14-175 mg] | 6-30 mg |
| | 0.002-1 mg/kg [0.14-70 mg] | 6-30 mg |
| | 0.002-<1 mg/kg [0.14-<70 mg] | 6-30 mg |
| | 0.002-0.5 mg/kg [0.14-35 mg] | 6-30 mg |
| | 0.002-0.1 mg/kg [0.14-7 mg] | 6-30 mg |
| MPDL3280A | 0.001-5 mg/kg [0.07-350 mg] | 0.25-30 mg |
| | 0.001-2.5 mg/kg [0.07-175 mg] | 0.25-30 mg |
| | 0.001-1 mg/kg [0.07-70 mg] | 0.25-30 mg |
| | 0.001-<1 mg/kg [0.07-<70 mg] | 0.25-30 mg |
| | 0.001-0.5 mg/kg [0.07-35 mg] | 0.25-30 mg |

TABLE 1.2-continued

Examples of doses of the PD-1 pathway inhibitor and LAG-3 protein or derivative thereof, according to embodiments of combined preparations or compositions of the invention

| Type of PD-1 pathway inhibitor | Dose of PD-1 pathway inhibitor: mg/kg [mg dose for 70 kg human] | Human dose of LAG-3 protein or derivative thereof (given as a mg dose of IMP321, or a molar equivalent thereof) |
|---|---|---|
| | 0.001-0.1 mg/kg [0.07-7 mg] | 0.25-30 mg |
| | 0.002-5 mg/kg [0.14-350 mg] | 0.25-30 mg |
| | 0.002-2.5 mg/kg [0.14-175 mg] | 0.25-30 mg |
| | 0.002-1 mg/kg [0.14-70 mg] | 0.25-30 mg |
| | 0.002-<1 mg/kg [0.14-<70 mg] | 0.25-30 mg |
| | 0.002-0.5 mg/kg [0.14-35 mg] | 0.25-30 mg |
| | 0.002-0.1 mg/kg [0.14-7 mg] | 0.25-30 mg |
| MPDL3280A | 0.001-5 mg/kg [0.07-350 mg] | 1-30 mg |
| | 0.001-2.5 mg/kg [0.07-175 mg] | 1-30 mg |
| | 0.001-1 mg/kg [0.07-70 mg] | 1-30 mg |
| | 0.001-<1 mg/kg [0.07-<70 mg] | 1-30 mg |
| | 0.001-0.5 mg/kg [0.07-35 mg] | 1-30 mg |
| | 0.001-0.1 mg/kg [0.07-7 mg] | 1-30 mg |
| | 0.002-5 mg/kg [0.14-350 mg] | 1-30 mg |
| | 0.002-2.5 mg/kg [0.14-175 mg] | 1-30 mg |
| | 0.002-1 mg/kg [0.14-70 mg] | 1-30 mg |
| | 0.002-<1 mg/kg [0.14-<70 mg] | 1-30 mg |
| | 0.002-0.5 mg/kg [0.14-35 mg] | 1-30 mg |
| | 0.002-0.1 mg/kg [0.14-7 mg] | 1-30 mg |
| MPDL3280A | 0.001-5 mg/kg [0.07-350 mg] | 6-30 mg |
| | 0.001-2.5 mg/kg [0.07-175 mg] | 6-30 mg |
| | 0.001-1 mg/kg [0.07-70 mg] | 6-30 mg |
| | 0.001-<1 mg/kg [0.07-<70 mg] | 6-30 mg |
| | 0.001-0.5 mg/kg [0.07-35 mg] | 6-30 mg |
| | 0.001-0.1 mg/kg [0.07-7 mg] | 6-30 mg |
| | 0.002-5 mg/kg [0.14-350 mg] | 6-30 mg |
| | 0.002-2.5 mg/kg [0.14-175 mg] | 6-30 mg |
| | 0.002-1 mg/kg [0.14-70 mg] | 6-30 mg |
| | 0.002-<1 mg/kg [0.14-<70 mg] | 6-30 mg |
| | 0.002-0.5 mg/kg [0.14-35 mg] | 6-30 mg |
| | 0.002-0.1 mg/kg [0.14-7 mg] | 6-30 mg |

The LAG-3 derivative may be any of the LAG-3 derivatives described above, or shown in FIG. 7. In particular embodiments, the LAG-3 derivative is IMP321.

When administered in separate dosages, the LAG-3 protein, or derivative thereof, and the PD-1 pathway inhibitor may be administered substantially simultaneously (for example, within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, about 72 hours, or about 96 hours, or more.

The skilled person will be able to determine, and optimise, a suitable time course for sequential administration, depending on the particular combination of the LAG-3 protein, or derivative thereof, and the PD-1 pathway inhibitor. The time course is preferably selected such that there is at least one beneficial effect, for example an enhancing of the effect of the LAG-3 protein, or derivative thereof, or the PD-1 pathway inhibitor, or a mutual enhancing of the effect of the combination components, for example a more than additive effect, additional advantageous effects, fewer side effects, less toxicity, or a combined therapeutic effect compared with a non-effective dosage of one or both of the combination components, and very preferably a synergism of the combination components.

It will be appreciated that the optimum time course will depend on factors such as the time taken for the peak plasma concentration of the compound to be reached after administration, and the elimination half-life of each compound. Preferably the time difference is less than the half-life of the first component to be administered.

The skilled person will also be able to determine appropriate timing for administration. In certain embodiments, the PD-1 pathway inhibitor may be administered in the morning, and the LAG-3 protein, or derivative thereof, administered at least once later in the day. In other embodiments, the PD-1 pathway inhibitor and LAG-3 protein, or derivative thereof, may be administered at substantially the same time.

In some embodiments, the PD-1 pathway inhibitor may be administered to the subject, for example, by a medical practitioner, and the subject may be provided with a dose of the LAG-3 protein, or derivative thereof, for example in a pre-filled syringe, to administer later (for example later the same day, or the next day).

The PD-1 pathway inhibitor and LAG-3 protein, or derivative thereof, may be administered daily, weekly, every two weeks, every three weeks, monthly, every 2 months, 3 months, 4 months, 5 months, 6 months, 7 months, 8 months, 9 months, 10 months, 11 months, 1 year, 2 years, 3 years, 4 years, 5 years, or more.

The subject may receive doses of the PD-1 pathway inhibitor and LAG-3 protein, or derivative thereof, over a period of weeks, months, or years. For example, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, or more.

The subject may be a mammalian subject, suitably a human subject.

Cancers that may be treated according to the invention include cancers in which tumor cells of the cancer express PD-L1 and/or PD-L2 (i.e. PD-L1- and/or PD-L2-positive cancers).

PD-L1 expression has been detected in lung, ovary, renal, and colon carcinomas and in malignant melanoma but not in normal tissues, including the lung, uterus, kidney, colon, or skin (Benson et al, Blood 116, 2286-2294 (2010); Blank et al, Int. J. Cancer 119, 317-327 (2006); Dong, et al, Nat. Med. 8, 793-800 (2002)). PD-L1 expression by tumor cells is associated with a worse prognosis in breast cancer, gastric cancer, esophageal cancer, hepatocellular carcinoma, malignant melanoma, ovarian cancer, pancreatic cancer, renal cell carcinoma, and urothelial cancer (Zou & Chen, Nat. Rev. Immunol. 8, 467-477 (2008)).

There is also evidence that human tumors can express PD-L2 (Rozali, et al, Clin. Dev. Immunol. 2012, 656340 (2012); Karim, et al, Clin. Cancer Res. 15, 6341-6347 (2009)). Non-small cell lung cancer- (NSCLC-) associated fibroblasts constitutively express both PD-L1 and PD-L2. Decreased survival in patients with PD-L2—positive (vs. PD-L2-negative), esophageal, ovarian, or hepatocellular cancer has also been described.

Cancers that may be treated according to the invention also include cancers in which tumor-infiltrating lymphocytes (TILs), especially $CD8^+$ TILs, express PD-1, or cancers in which TILs express higher levels of PD-1 than circulating lymphocytes.

In both NSCLC and melanoma patients, higher levels of PD-1 were observed on TILs than on circulating lymphocytes (Blank, et al, Int. J. Cancer 119, 317-327 (2006); Zhang et al, Cell. Mol. Immunol. 7, 389-395 (2010)). In the peripheral blood of vaccinated melanoma patients, both melanoma antigen-specific cytotoxic lymphocytes and Tregs expressed PD-1 (Wang, et al, Int. Immunol. 21, 1065-1077 (2009)). There was also a negative correlation between tumor PD-L2 expression and the presence of $CD8^+$ TILs in esophageal cancer (Rozali, et al, Clin. Dev. Immunol. 2012, 656340 (2012)).

$CD8^+$ TILs isolated from NSCLCs had increased expression of PD-1 and impaired functional responses (in vitro proliferation and inflammatory cytokine production) as compared with circulating $CD8^+$ T cells or $CD8^+$ T cells from healthy volunteers. Addition of anti-PD-L1 antibody significantly improved the ability of the $CD8^+$ TILs to proliferate and produce interferon-γ in vitro (Zhang, et al, Cell. Mol. Immunol. 7, 389-395 (2010)). In a similar study using cultures of tumor-derived dendritic cells and TILs from ovarian cancer patients, addition of anti-PD-L1 antibody significantly increased interferon-γ production by TI Ls in response to tumor antigens. When these TI Ls were transferred to immunodeficient mice bearing the ovarian tumors, reduced tumor growth was seen as compared with that of mice in control groups (Curiel, et al, Nat. Med. 9, 562-567 (2003)).

In particular, cancers that may be treated according to the invention include skin, lung (especially squamous or non-squamous NSCLC), ovarian, renal, colon, colorectal, breast, gastric, esophageal, pancreatic, bladder, urothelial, and liver cancer.

Other examples of cancers that may be treated according to the invention include a melanoma (for example, metastatic malignant melanoma), a prostate cancer (for example hormone refractory prostate adenocarcinoma), a head and neck cancer (for example, squamous cell carcinoma of the head and neck), a cervical cancer, a thyroid cancer, a glioblastoma, a glioma, leukemia, a lymphoma (for example, a B cell lymphoma), an adrenal gland cancer, an AIDS-associated cancer, an alveolar soft part sarcoma, an astrocytic tumor, bone cancer, a brain and spinal cord cancer, a metastatic brain tumor, a carotid body tumor, a chondrosarcoma, a chordoma, a chromophobe renal cell carcinoma, a clear cell carcinoma, cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gestational trophoblastic disease, a germ cell tumor, a haematological malignancy, hepatocellular carcinoma, an islet cell tumor, a Kaposi's sarcoma, a kidney cancer, a lipoma/benign lipomatous tumor, a liposarcoma/malignant lipomatous tumor, a medulloblastoma, a meningioma, a Merkel cell carcinoma, a multiple endocrine neoplasia, a multiple myeloma, a myelodysplasia syndrome, a neuroblastoma, a neuroendocrine tumor, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a soft-tissue sarcoma, a squamous cell cancer, a stomach cancer, a synovial sarcoma, a testicular cancer, a thymic carcinoma, a thymoma, a thyroid metastatic cancer, or a uterine cancer.

In general, the components of a combination of the invention, or a composition of the invention, may be administered by known means, in any suitable formulation, by any suitable route. In some embodiments, the LAG-3 protein, or derivative thereof, is administered parenterally (including by subcutaneous, intravenous, or intramuscular injection). In some embodiments, the PD-1 pathway inhibitor is administered intravenously. In particular embodiments, the LAG-3 protein, or derivative thereof, is administered subcutaneously, and the PD-1 pathway inhibitor is administered intravenously.

Suitable pharmaceutical compositions and dosage forms may be prepared using conventional methods known to those in the field of pharmaceutical formulation and described in the relevant texts and literature, for example, in Remington: The Science and Practice of Pharmacy (Easton, Pa.: Mack Publishing Co., 1995).

It is especially advantageous to formulate combinations or compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, for example, two tablets or capsules taken together may provide a therapeutically effective dosage, such that the unit dosage in each tablet or capsule is approximately 50% of the therapeutically effective amount.

Preparations according to the invention for parenteral administration include sterile aqueous and non-aqueous solutions, suspensions, and emulsions. Injectable aqueous solutions contain the active agent in water-soluble form. Examples of non-aqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations may be rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

In addition to the formulations described previously, the active agent may be formulated as a depot preparation for controlled release of the active agent, preferably sustained release over an extended time period. These sustained release dosage forms are generally administered by implantation (for example, subcutaneously or intramuscularly or by intramuscular injection).

Combined preparations of the invention may be packaged with instructions for administration of the components on the combination. The instructions may be recorded on a suitable recording medium or substrate. For example, the instructions may be printed on a substrate, such as paper or plastic. The instructions may be present as a package insert, in the labeling of the container or components thereof (i.e., associated with the packaging or sub-packaging). In other embodiments, the instructions are present as an electronic storage data file present on a suitable computer readable storage medium, for example, CD-ROM, diskette. Some or all components of the combined preparation may be packaged in suitable packaging to maintain sterility.

Embodiments of the invention are described below, by way of example only, with reference to the accompanying drawings.

In the Examples, Tables, and Figures below, the term "anti-PD1 antibody" is used synonymously with "anti-PD-1 antibody", and the term "anti-PDL1 antibody" is used synonymously with "anti-PD-L1 antibody".

EXAMPLES

Example 1

Effect of LAG-3Ig and Anti-PD1 Antibody on the Secretion of IFN-γ Induced by Antigenic Stimulation This example demonstrates the effect of a soluble derivative of LAG-3 (LAG-3Ig, also known as IMP321), and an anti-PD1 antibody, on T-cell activation in vitro using an IFN-γ secretion assay. Peripheral blood mononuclear cells (PBMCs) include lymphocytes (T cells, B cells, and NK cells), monocytes, and dendritic cells. IFN-γ is predominantly secreted by activated $CD4^+$ and $CD8^+$ memory and effector T cells and by NK cells upon activation. After re-stimulation with specific antigen in vitro, secretion of IFN-γ is induced.

PBMCs from three healthy donors ($0.2\times10^6$ cells/well, at $1\times10^6$M/ml in Complete Roswell Park Memorial Institute (RPMI)+10% Foetal Bovine Serum (FBS)) were incubated with a pool of peptides covering the sequence of human cytomegalovirus (CMV) pp65 in triplicate (PepTivator® CMV pp65 form Miltenyi Biotec, Cat. #130-093-435), in the presence or the absence of 30 ng/ml of LAG-3Ig and indicated concentrations of anti-PD1 mAb (clone EH12.1, BD biosciences, Cat. #562138). The pool of peptides consisted mainly of 15-mer sequences, with an 11 amino acid overlap, covering the complete sequence of the pp65 protein of human CMV strain AD169 (Swiss-Prot Acc. No. P06725).

The T cell response was evaluated by measuring the concentration of IFN-γ in cell supernatants two days post-stimulation using BD Cytometric Bead Array.

Figures 2A, 2B, 2C:
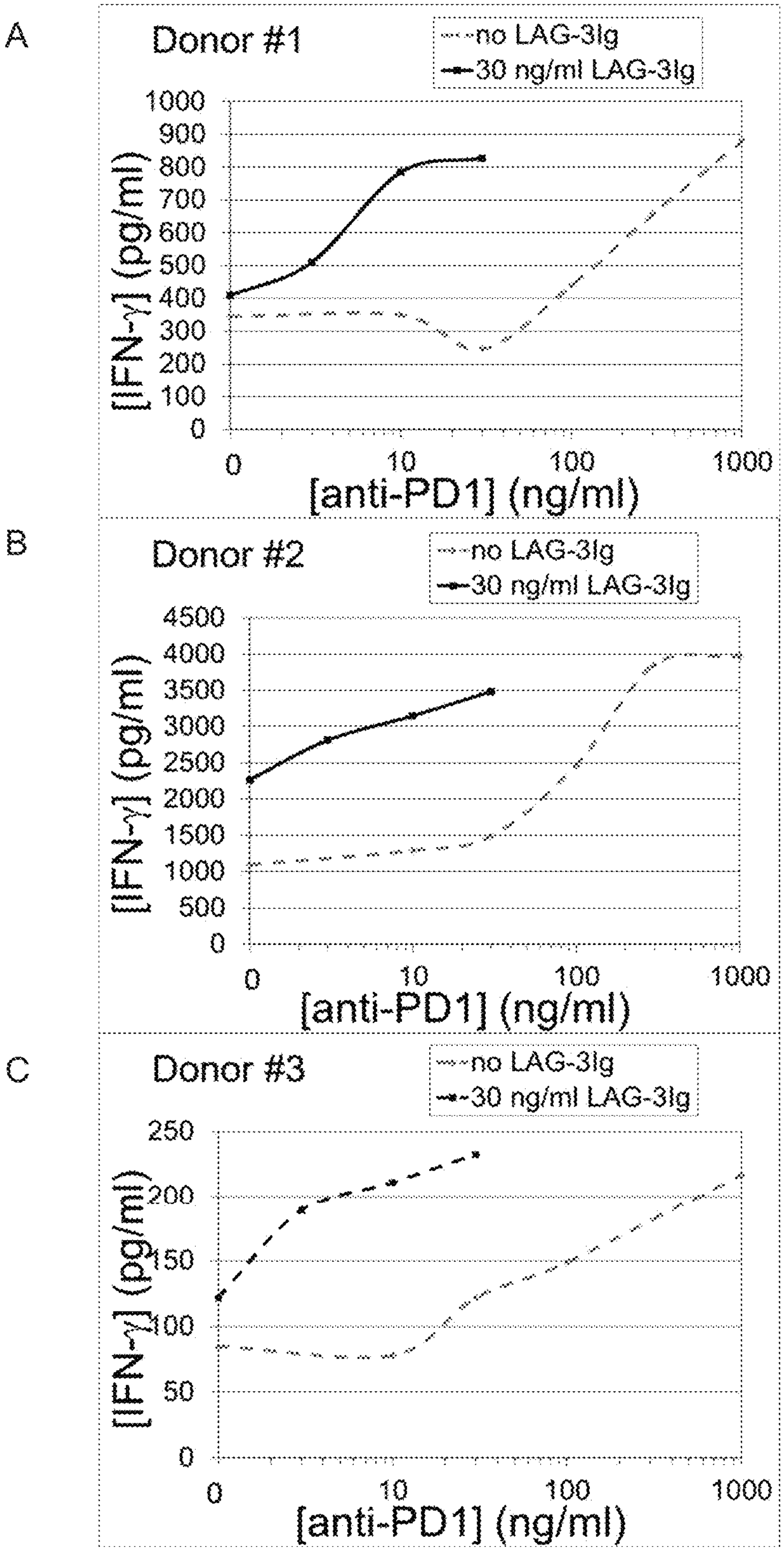
FIGS. 2A-2C. Show the effect of LAG-3Ig and anti-PD1 antibody on the secretion of IFN-γ induced by antigenic stimulation. (A) Donor 1, (B) Donor 2, (C) Donor 3.

The concentrations of IFN-γ present in the pooled triplicates for each donor are recorded in Table 2 below. FIG. 2 shows the concentrations of IFN-γ plotted against the concentration of anti-PD1 mAb for each donor.

TABLE 2

Secretion of IFN-γ induced by antigen in the presence of anti-PD1 antibody with and without LAG-3Ig

| | [IFN-γ] (pg/ml) | | | | | |
|---|---|---|---|---|---|---|
| Donor No: | 1 | | 2 | | 3 | |
| Anti-PD1 antibody (ng/ml) | No LAG-3Ig | 30 ng/ml LAG-3Ig | No LAG-3Ig | 30 ng/ml LAG-3Ig | No LAG-3Ig | 30 ng/ml LAG-3Ig |
| 0 | 345 | 409 | 1095 | 2269 | 85 | 122 |
| 3 | | 510 | | 2812 | | 188 |
| 10 | 350 | 785 | 1292 | 3151 | 78 | 211 |
| 30 | 246 | 828 | 1491 | 3484 | 122 | 232 |
| 100 | 439 | | 2467 | | 149 | |
| 300 | 657 | | 3856 | | | |
| 1000 | 881 | | 3970 | | 216 | |

The results show that secretion of IFN-γ was dramatically increased when the PBMCs were incubated in the presence of 30 ng/ml LAG-3Ig and lower concentrations of anti-PD1 antibody, compared with anti-PD1 antibody alone. For example, for each donor, the increase in concentration of IFN-γ above the background level (i.e. the concentration of IFN-γ in the absence of anti-PD1 and LAG-3Ig) in the presence of 30 ng/ml LAG-3Ig and 30 ng/ml anti-PD1 antibody was greater than the sum of the corresponding increase in the presence of 30 ng/ml LAG-3Ig alone and 30 ng/ml anti-PD1 antibody alone, as shown in Table 3 below. The effect of the combination of LAG-3Ig and anti-PD1 antibody for each donor was, therefore, synergistic.

TABLE 3

Increase in IFN-γ concentration above background induced by antigen in the presence of 30 ng/ml anti-PD1 antibody and/or 30 ng/ml LAG-3Ig

| | Donor No. | | |
|---|---|---|---|
| Stimulation condition | 1 | 2 | 3 |
| 30 ng/ml LAG-3Ig | 64 | 1174 | 37 |
| 30 ng/ml anti-PD-1 antibody | −99 | 396 | 37 |
| 30 ng/ml LAG-3Ig + 30 ng/ml anti-PD-1 antibody | 483 | 2389 | 147 |

The results also show that secretion of IFN-γ induced by a combination of LAG-3Ig and a relatively low concentration of anti-PD1 antibody (30 ng/ml) was equivalent to secretion of IFN-γ induced by a much higher concentration (300 ng/ml-1000 ng/ml, 10 to over 30 times higher) of anti-PD1 antibody alone. For Donor Nos. 1 and 3, similar concentrations of IFN-γ were secreted when PBMCs were incubated with 30 ng/ml anti-PD1 and 30 ng/ml LAG-3Ig compared with 1000 ng/ml anti-PD1 antibody alone. For Donor No. 2, similar concentrations of IFN-γ were secreted when PBMCs were incubated with 30 ng/ml anti-PD1 and 30 ng/ml LAG-3Ig compared with 300 ng/ml and 1000 ng/mlanti-PD1 antibody alone.

It was concluded from these results that in vitro T cell response (as measured by IFN-γ secretion) induced by relatively low doses of anti-PD1 antibody is synergistically increased (by approximately −7.5, 1.5, and 2 times for Donor Nos. 1, 2, and 3, respectively) by a soluble LAG-3 derivative. It was also concluded that an equivalent in vitro T cell response is obtained using approximately 10-30 times less anti-PD1 antibody if this is combined with a soluble LAG-3 derivative.

Example 2

Effect of LAG-3Ig and Anti-PD1 Antibody on the Secretion of IFN-γ Induced by Antigenic Stimulation This example demonstrates the effect of a soluble derivative of LAG-3 (LAG-3Ig), and an anti-PD1 antibody, on T-cell activation in vitro using an IFN-γ secretion assay.

PBMCs from 10 healthy donors ($0.2\times10^6$ cells/well, at $1\times10^6$M/ml in Complete RPMI+10% FBS) were incubated with a pool of peptides covering the sequence of CMV pp65 in triplicate (PepTivator® CMV pp65 form Miltenyi Biotec, Cat. #130-093-435), without any additive (Medium), with 30 ng/ml or 1000 ng/ml of anti-PD1 mAb (clone EH12.1, BD biosciences Cat. #562138), with 30 ng/ml of LAG-3Ig, or with 30 ng/ml of LAG-3Ig and 30 ng/ml of anti-PD1 mAb. The T cell response was evaluated by measuring the concentration of IFN-γ in cell supernatants two days post-stimulation using BD Cytometric Bead Array.

Figure 3:
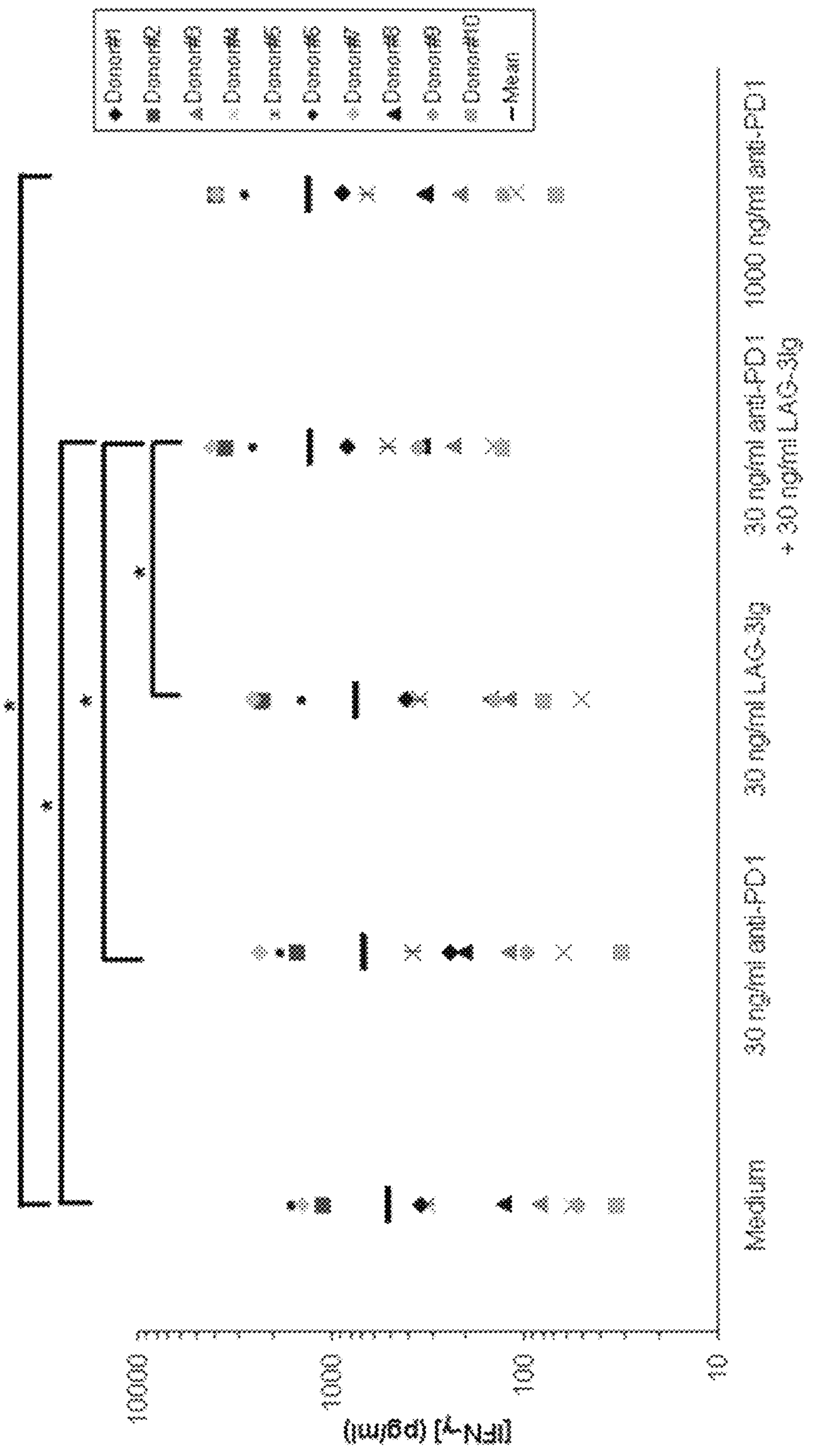
FIG. 3. Shows the effect of LAG-3Ig and anti-PD1 antibody on the secretion of IFN-γ induced by antigenic stimulation.
Figure 4A:
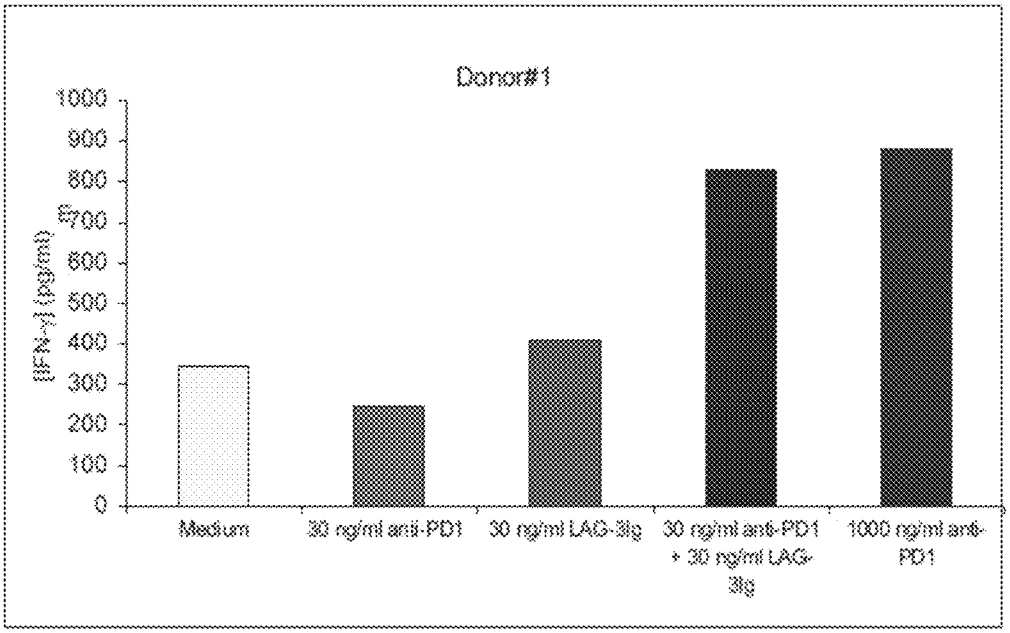
FIGS. 4A-4J. Show the effect of LAG-3Ig and anti-PD1 antibody on the secretion of IFN-γ induced by antigenic stimulation. (A) through (J) show data from Donor 1 through Donor 10.
Figure 4B:
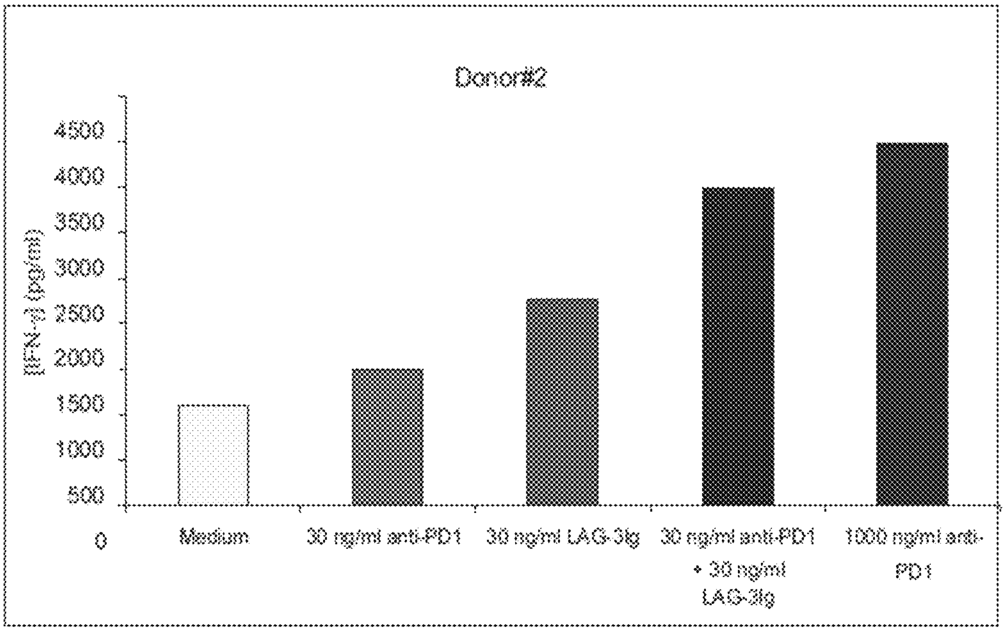
Figure 4C:
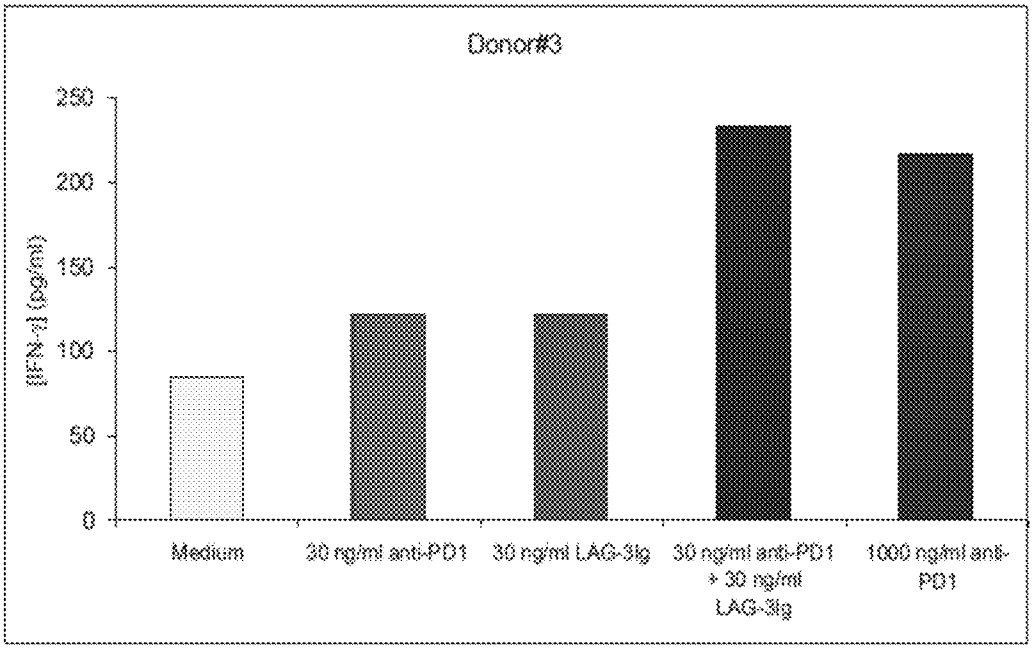
Figure 4D:
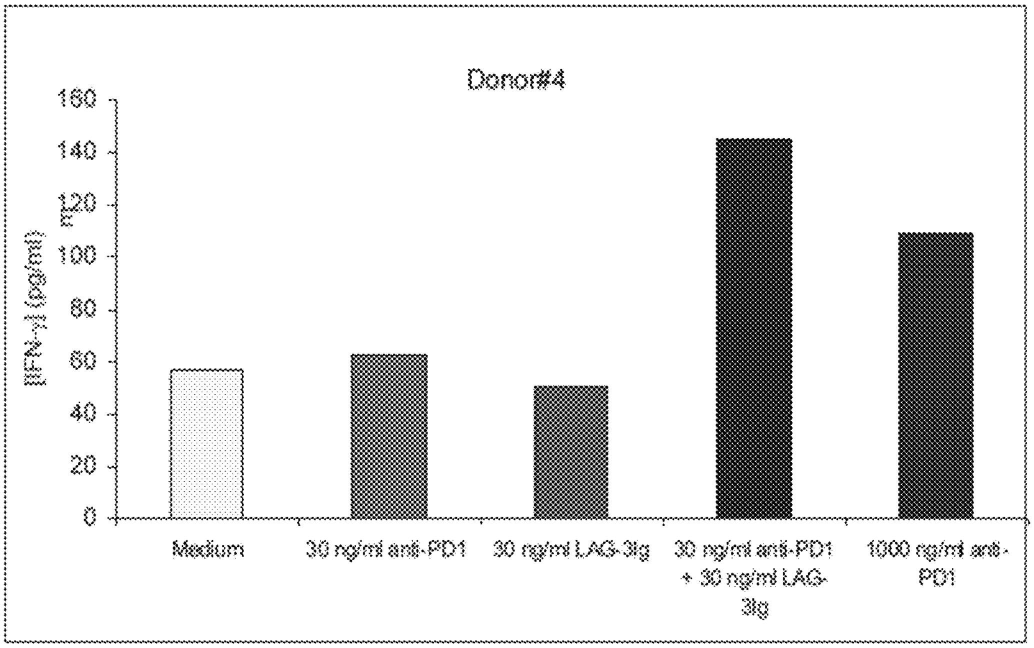
Figure 4E:
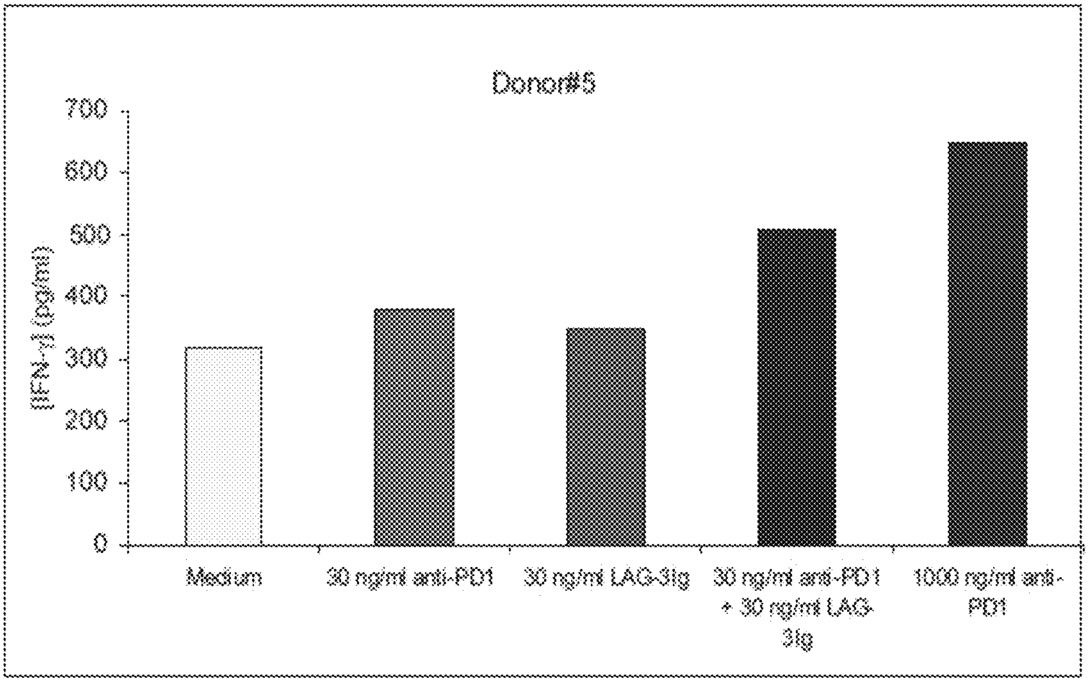
Figure 4F:
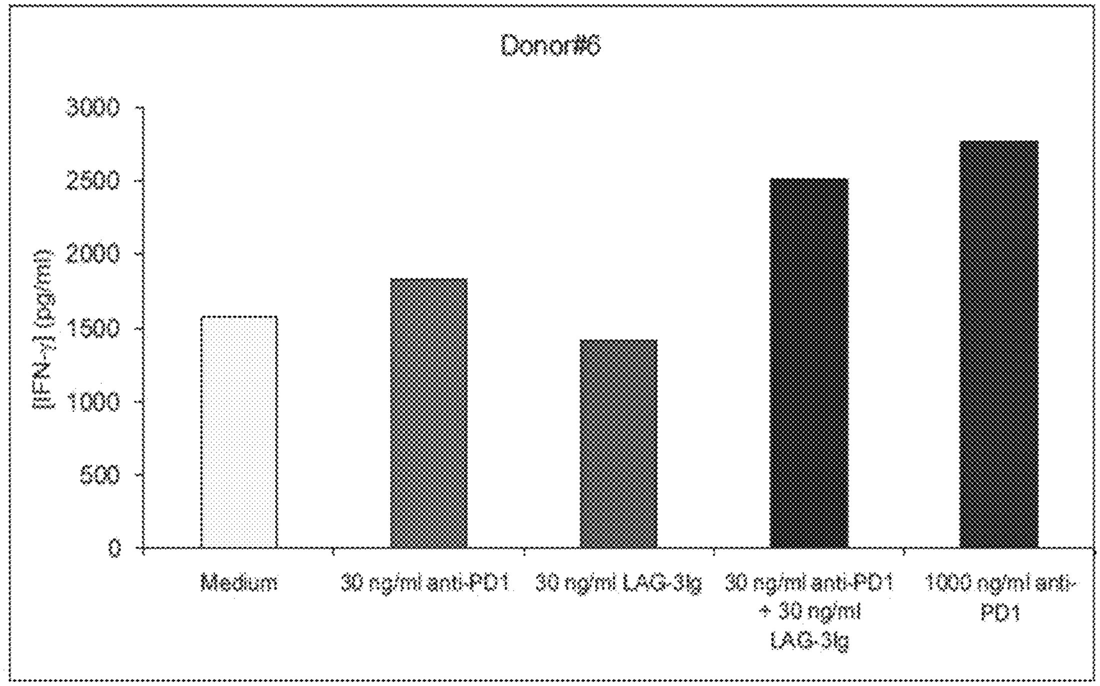
Figure 4G:
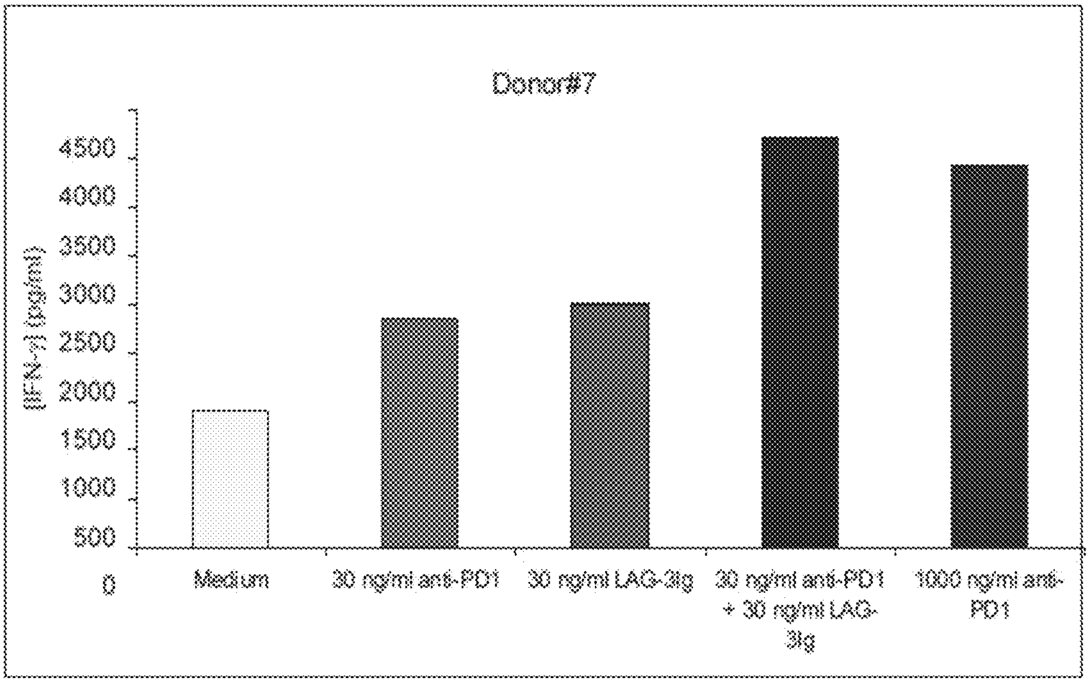
Figure 4H:
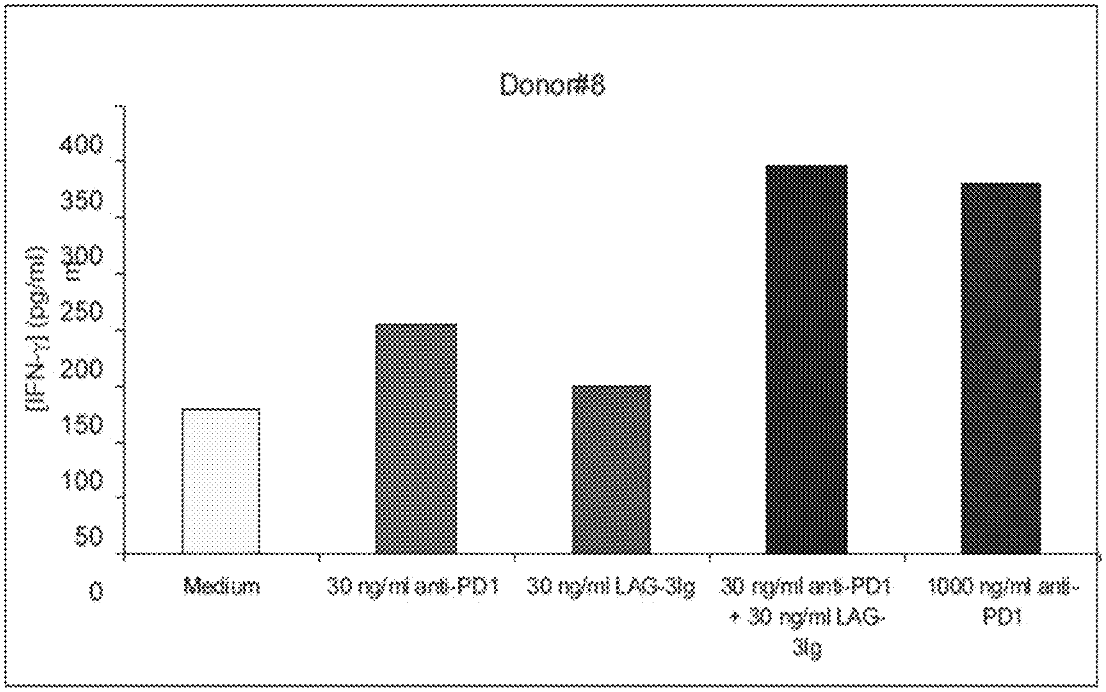
Figures 4I, 4J:
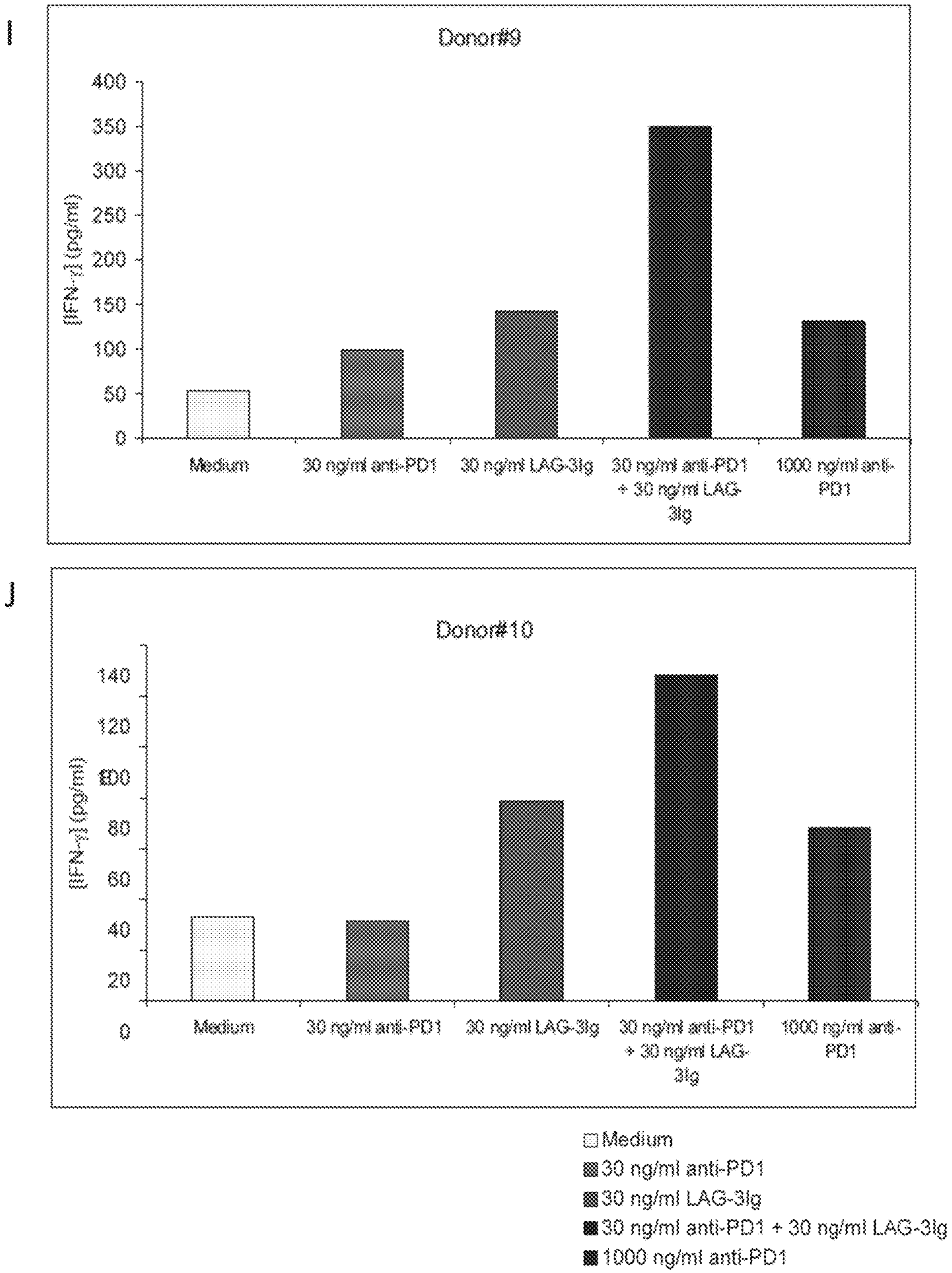

The concentrations of IFN-γ in the pooled triplicates for each condition of stimulation, for each donor, are recorded in Table 4 below. The mean of the results obtained for the 10 donors are shown in Table 5. The results for each donor are also plotted in FIGS. 3 and 4. The statistical differences (*$p<0.05$) are shown in black in FIG. 3.

TABLE 4

Secretion of IFN-γ induced by antigen in the presence of anti-PD1 antibody with and without LAG-3Ig

| Stimulation condition | | [IFN-γ] (pg/ml) | | | | | | | | | |
|---|---|---|---|---|---|---|---|---|---|---|---|
| [Anti-PD1] | [LAG-3Ig] | Donor | | | | | | | | | |
| (ng/ml) | (ng/ml) | 1 | 2 | 3 | 4 | 5 | 6 | 7 | 8 | 9 | 10 |
| — | — | 345 | 1095 | 85 | 57 | 319 | 1583 | 1405 | 130 | 53 | 33 |
| 30 | — | 246 | 1491 | 122 | 63 | 378 | 1836 | 2355 | 204 | 97 | 31 |
| — | 30 | 409 | 2269 | 122 | 51 | 350 | 1406 | 2511 | 150 | 142 | 79 |
| 30 | 30 | 828 | 3484 | 232 | 145 | 506 | 2510 | 4217 | 347 | 350 | 128 |
| 1000 | — | 881 | 3970 | 216 | 109 | 650 | 2765 | 3913 | 329 | 130 | 68 |

TABLE 5

Mean IFN-γ concentration for each different stimulation condition

| Stimulation condition | | | Increase in mean |
|---|---|---|---|
| [Anti-PD1] (ng/ml) | [LAG-3Ig] (ng/ml) | Mean [IFN-γ] (pg/ml) | [IFN-γ] (pg/ml) above mean background |
| — | — | 510 | — |
| 30 | — | 682 | 172 |
| — | 30 | 749 | 239 |
| 30 | 30 | 1275 | 765 |
| 1000 | — | 1303 | 793 |

The results show that secretion of IFN-γ was much higher for each donor when the PBMCs were incubated in the presence of 30 ng/ml LAG-3Ig and 30 ng/ml anti-PD1 antibody, compared with 30 ng/ml LAG-3Ig or 30 ng/ml anti-PD1 antibody alone. Table 5 shows that the increase in mean concentration of IFN-γ above the mean background level (i.e. the mean concentration of IFN-γ in the absence of anti-PD1 and LAG-3Ig) in the presence of 30 ng/ml LAG-3Ig and 30 ng/ml anti-PD1 antibody was greater than the sum of the corresponding increase in the presence of 30 ng/ml LAG-3Ig alone and 30 ng/ml anti-PD1 antibody alone (i.e. 765>239+172). The effect of the combination of LAG-3Ig and anti-PD1 antibody was, therefore, synergistic.

The results also show that secretion of IFN-γ induced by a combination of LAG-3Ig and a relatively low concentration of anti-PD1 antibody (30 ng/ml) was equivalent to secretion of IFN-γ induced by a much higher concentration (1000 ng/ml, over 30 times higher) of anti-PD1 antibody alone.

It was concluded from these results that in vitro T cell response (as measured by IFN-γ secretion) induced by relatively low doses of anti-PD1 antibody is synergistically increased (by approximately 2 times on average) by a soluble LAG-3 derivative. It was also concluded that an equivalent in vitro T cell response is obtained using over 30 times less anti-PD1 antibody if this is combined with a soluble LAG-3 derivative.

Example 3

Effect of LAG-3Ig and Anti-PD1 Antibody on the Secretion of TNF-α, IL-6, RANTES Induced by Antigenic Stimulation This example demonstrates the effect of a soluble derivative of LAG-3 (LAG-3Ig), and an anti-PD1 antibody, on T-cell activation in vitro by measuring secretion of TNF-α, IL-6 and RANTES (CCL5).

PBMCs from 10 healthy donors ($0.2\times10^6$ cells/well, at $1\times10^6$M/ml in Complete RPMI+10% FBS) were incubated with a pool of peptides covering the sequence of CMV pp65 in triplicate (PepTivator® CMV pp65 form Miltenyi Biotec, Cat. #130-093-435), without any additive (Medium), with 30 ng/ml or 1000 ng/ml of anti-PD1 mAb (clone EH12.1, BD biosciences Cat. #562138), with 30 ng/ml of LAG-3Ig, or with 30 ng/ml of LAG-3Ig and 30 ng/ml of anti-PD1 mAb.

The T cell response was evaluated by measuring the concentration of TNF-α, IL-6 and RANTES (CCL5) in cell supernatants 2 days post-stimulation using BD Cytometric Bead Array.

The concentration of cytokines/chemokines in the pooled triplicates for each condition of stimulation, for each donor, are recorded in Tables 6-8 below. The mean of the results obtained for the 10 donors are shown in Table 9, and the increase of the means above mean background is shown in Table 10. The results for each donor are also plotted in FIG. 5, and the statistical differences (*$p<0.05$) are shown in black.

TABLE 6

Secretion of TNF-α induced by antigen in the presence of anti-PD1 antibody with and without LAG-3Ig

| Stimulation condition | | [TNF-α] (pg/ml) | | | | | | | | | |
|---|---|---|---|---|---|---|---|---|---|---|---|
| [Anti-PD1] | [LAG-3Ig] | Donor | | | | | | | | | |
| (ng/ml) | (ng/ml) | 1 | 2 | 3 | 4 | 5 | 6 | 7 | 8 | 9 | 10 |
| — | — | 20 | 12 | | 16 | 20 | 85 | 1 | 10 | 4 | 5 |
| 30 | — | 31 | 15 | | 29 | 23 | 116 | 1 | 7 | 4 | 90 |
| — | 30 | 67 | 36 | | 97 | 100 | 645 | 15 | 123 | 34 | 72 |
| 30 | 30 | 78 | 44 | | 143 | 172 | 793 | 24 | 152 | 64 | 229 |
| 1000 | — | 30 | 15 | | 33 | 47 | 325 | 4 | 17 | 6 | 22 |

TABLE 7

Secretion of IL-6 induced by antigen in the presence of anti-PD1 antibody with and without LAG-3Ig

| Stimulation condition | | [IL-6] (pg/ml) | | | | | | | | | |
|---|---|---|---|---|---|---|---|---|---|---|---|
| [Anti-PD1] | [LAG-3Ig] | Donor | | | | | | | | | |
| (ng/ml) | (ng/ml) | 1 | 2 | 3 | 4 | 5 | 6 | 7 | 8 | 9 | 10 |
| — | — | 1000 | 401 | 71 | 255 | 150 | 1316 | 284 | 171 | 420 | 1661 |
| 30 | — | 1420 | 716 | 91 | 312 | 208 | 1523 | 303 | 168 | 278 | 8026 |
| — | 30 | 1073 | 563 | 245 | 668 | 326 | 19703 | 466 | 432 | 568 | 11324 |
| 30 | 30 | 1254 | 671 | 223 | 815 | 546 | 24102 | 560 | 471 | 833 | 62195 |
| 1000 | — | 1130 | 690 | 231 | 210 | 323 | 3411 | 576 | 276 | 426 | 4858 |

TABLE 8

Secretion of RANTES (CCL5) induced by antigen in the presence of anti-PD1 antibody with and without LAG-3Ig

| Stimulation condition | | [RANTES (CCL5)] (pg/ml) | | | | | | | | | |
|---|---|---|---|---|---|---|---|---|---|---|---|
| [Anti-PD1] | [LAG-3Ig] | Donor | | | | | | | | | |
| (ng/ml) | (ng/ml) | 1 | 2 | 3 | 4 | 5 | 6 | 7 | 8 | 9 | 10 |
| — | — | 62 | 18 | 6 | 52 | 249 | 174 | 302 | 393 | 135 | 182 |
| 30 | — | 54 | 22 | 11 | 51 | 253 | 210 | 296 | 435 | 142 | 217 |
| — | 30 | 93 | 46 | 14 | 142 | 392 | 689 | 341 | 785 | 146 | 385 |
| 30 | 30 | 100 | 61 | 13 | 148 | 497 | 785 | 319 | 712 | 180 | 430 |
| 1000 | — | 64 | 26 | 10 | 70 | 300 | 357 | 321 | 435 | 141 | 217 |

TABLE 9

Mean TNF-α, IL-6 and RANTES (CCL5) concentration for each different stimulation condition

| Stimulation condition | | | | |
|---|---|---|---|---|
| [Anti-PD1] (ng/ml) | [LAG-3Ig] (ng/ml) | Mean [TNF-α] (pg/ml) | Mean [IL-6] (pg/ml) | Mean [CCL5] (pg/ml) |
| — | — | 19 | 573 | 157 |
| 30 | — | 35 | 1305 | 169 |
| — | 30 | 132 | 3537 | 303 |
| 30 | 30 | 189 | 9167 | 324 |
| 1000 | — | 55 | 1213 | 194 |

TABLE 10

Increase in mean TNF-α, IL-6 and RANTES (CCL5) concentration above mean background for each different stimulation condition

| Stimulation condition | | Increase in mean [TNF-α] (pg/ml) | Increase in mean [IL-6] (pg/ml) | Increase in mean [CCL5] (pg/ml) |
|---|---|---|---|---|
| [Anti-PD1] (ng/ml) | [LAG-3Ig] (ng/ml) | above mean background | above mean background | above mean background |
| 30 | — | 16 | 732 | 12 |
| — | 30 | 113 | 2964 | 146 |
| 30 | 30 | 170 | 8594 | 167 |
| 1000 | — | 36 | 640 | 37 |

The results show that secretion of IL-6 was much higher for each donor when the PBMCs were incubated in the presence of 30 ng/ml LAG-3Ig and 30 ng/ml anti-PD1 antibody, compared with 30 ng/ml LAG-3Ig or 30 ng/ml anti-PD1 antibody alone. Table 10 shows that the increase in mean concentration of IL-6 above the mean background level (i.e. the mean concentration of IL-6 in the absence of anti-PD1 and LAG-3Ig) in the presence of 30 ng/ml LAG-3Ig and 30 ng/ml anti-PD1 antibody was greater than the sum of the corresponding increase in the presence of 30 ng/ml LAG-3Ig alone and 30 ng/ml anti-PD1 antibody alone (i.e. 8594>732+2964). The effect of the combination of LAG-3Ig and anti-PD1 antibody was, therefore, synergistic.

The results also show that secretion of IL-6 induced by a combination of LAG-3Ig and a relatively low concentration of anti-PD1 antibody (30 ng/ml) was equivalent to secretion of IL-6 induced by a much higher concentration (1000 ng/ml, over 30 times higher) of anti-PD1 antibody alone.

It was concluded from these results that in vitro T cell response (as measured by IL-6 secretion) induced by relatively low doses of anti-PD1 antibody is synergistically increased (by over 2.3 times on average) by a soluble LAG-3 derivative.

Example 4

Effect of LAG-3Ig and Anti-PD1 Antibody on the Expression of Activation Markers Induced by Antigenic Stimulation This example demonstrates the effect of a soluble derivative of LAG-3 (LAG-3Ig), and an anti-PD1 antibody, on the expression of T cell activation markers.

PBMCs from 7 healthy donors ($0.2\times10^6$ cells/well, at $1\times10^6$M/ml in Complete RPMI+10% FBS) were incubated with a pool of peptides covering the sequence of CMV pp65 in triplicate (PepTivator® CMV pp65 form Miltenyi Biotec, Cat. #130-093-435), without any additive (Medium), with 30 ng/ml or 1000 ng/ml of anti-PD1 mAb (clone EH12.1, BD biosciences Cat. #562138), with 30 ng/ml of LAG-3Ig, or with 30 ng/ml of LAG-3Ig and 30 or 1000 ng/ml of anti-PD1 mAb.

The T cell response was evaluated by phenotyping the cells for the expression of three activation markers (LAG-3, CD69 and CD25) two days post-stimulation by flow cytometry.

Figures 6A, 6B, 6C:
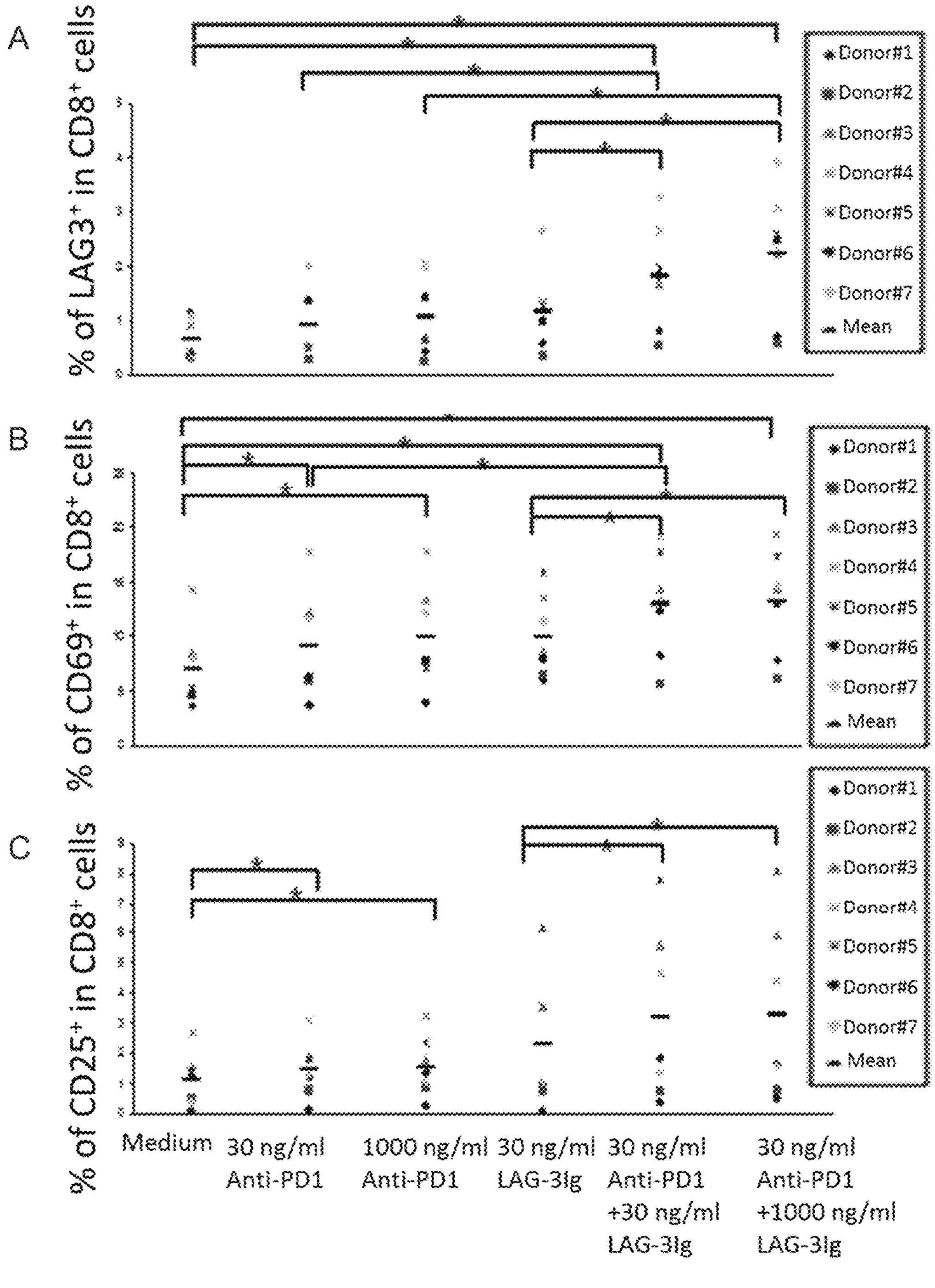
FIGS. 6A-6E. Show the effect of LAG-3Ig and anti-PD1 antibody on the expression of activation markers induced by antigenic stimulation. Note that the condition for the final column in each graph of FIG. 6 is "1000 ng/ml anti-PD1+30 ng/ml LAG-3Ig", rather than "30 ng/ml anti-PD1+1000 ng/ml LAG-3Ig" as indicated in the Figure. (A) Percent (%) of Lag3+ in CD8+ cells; (B) % of CD69+ in $CD8^+$ cells; (C) % of CD25 in $CD8^+$ cells; (D) % of activation markers in CD8+ cells; (E) % of Lag3+, CD69+, CD25+ in CD8+ cells.
Figures 6D, 6E:
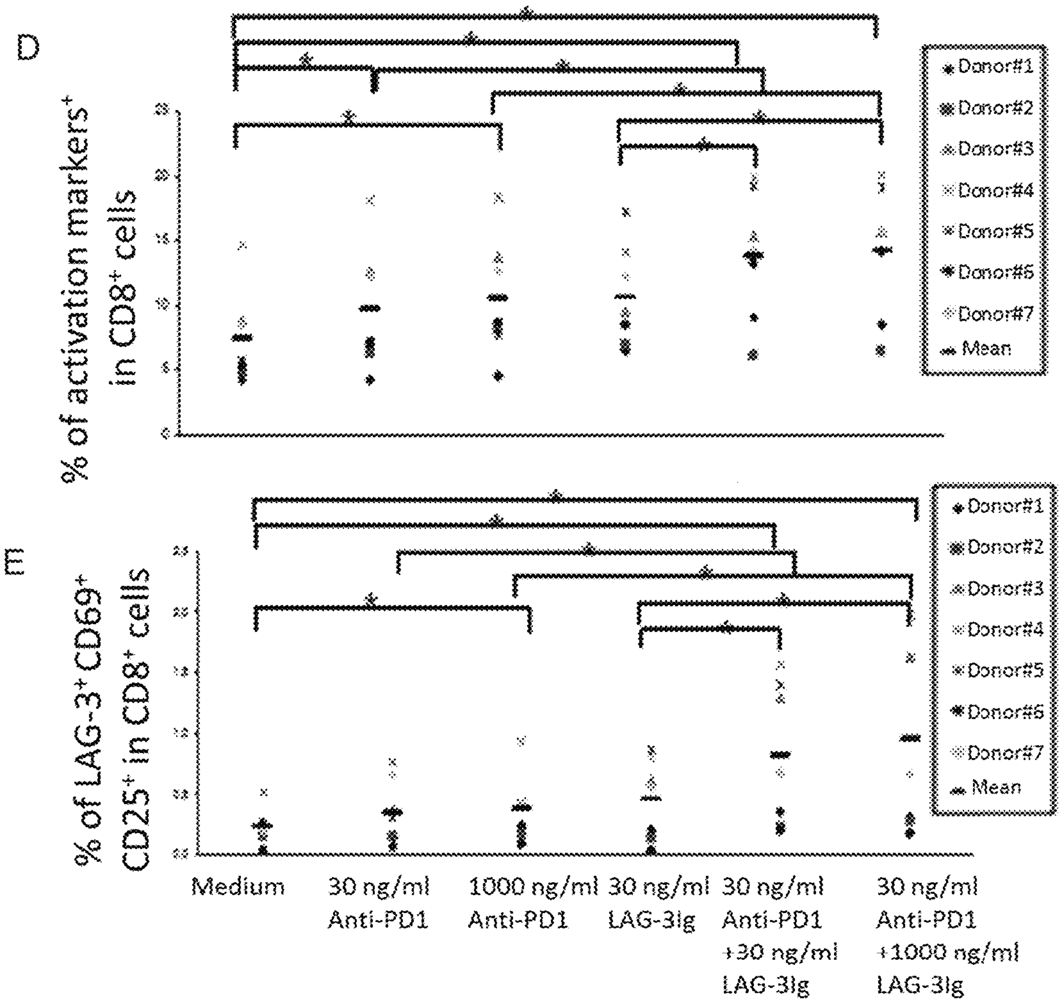

The percentage of CD8 cells expressing LAG-3, CD69, or CD25, at least one of the three activation markers (LAG-3, CD69, or CD25), or all three of the activation markers (LAG-3, CD69, and CD25), in the pooled triplicates, for each condition of stimulation, is recorded in Tables 11-15 below. The mean of the results obtained for the 7 donors are shown in Table 16, and the increase of the means above mean background is shown in Table 17. The results for each donor are also plotted in FIG. 6, and the statistical differences (*p<0.05) are shown in black.

TABLE 11

Percentage of CD8 cells expressing LAG-3 for each different stimulation condition

| Stimulation condition | | Percentage of CD8 cells expressing LAG-3 | | | | | | |
|---|---|---|---|---|---|---|---|---|
| [Anti-PD1] | [LAG-3Ig] | Donor | | | | | | |
| (ng/ml) | (ng/ml) | 1 | 2 | 3 | 4 | 5 | 6 | 7 |
| — | — | 0.39 | 0.33 | 0.36 | 0.89 | 0.45 | 1.13 | 1.09 |
| 30 | — | 0.29 | 0.28 | 0.56 | 1.40 | 0.49 | 1.38 | 2.03 |
| 1000 | — | 0.43 | 0.25 | 0.69 | 2.04 | 0.65 | 1.43 | 1.97 |
| — | 30 | 0.57 | 0.36 | 0.98 | 1.36 | 1.28 | 1.00 | 2.65 |
| 30 | 30 | 0.80 | 0.54 | 1.68 | 2.66 | 1.97 | 1.83 | 3.29 |
| 1000 | 30 | 0.72 | 0.57 | 2.25 | 3.08 | 2.59 | 2.47 | 3.91 |

TABLE 12

Percentage of CD8 cells expressing CD69 for each different stimulation condition

| Stimulation condition | | Percentage of CD8 cells expressing CD69 | | | | | | |
|---|---|---|---|---|---|---|---|---|
| [Anti-PD1] | [LAG-3Ig] | Donor | | | | | | |
| (ng/ml) | (ng/ml) | 1 | 2 | 3 | 4 | 5 | 6 | 7 |
| — | — | 3.67 | 4.57 | 8.44 | 14.28 | 5.29 | 4.59 | 7.93 |
| 30 | — | 3.73 | 6.03 | 12.26 | 17.65 | 6.44 | 6.23 | 11.62 |
| 1000 | — | 3.91 | 7.76 | 13.36 | 17.70 | 7.04 | 7.80 | 12.14 |
| — | 30 | 5.91 | 6.49 | 8.59 | 13.42 | 15.95 | 7.92 | 11.41 |
| 30 | 30 | 8.23 | 5.62 | 14.30 | 19.12 | 17.69 | 12.30 | 13.39 |
| 1000 | 30 | 7.82 | 6.09 | 14.47 | 19.37 | 17.33 | 12.97 | 14.67 |

TABLE 13

Percentage of CD8 cells expressing CD25 for each different stimulation condition

| Stimulation condition | | Percentage of CD8 cells expressing CD25 | | | | | | |
|---|---|---|---|---|---|---|---|---|
| [Anti-PD1] | [LAG-3Ig] | Donor | | | | | | |
| (ng/ml) | (ng/ml) | 1 | 2 | 3 | 4 | 5 | 6 | 7 |
| — | — | 1.27 | 0.51 | 1.53 | 2.67 | 1.41 | 0.07 | 0.41 |
| 30 | — | 1.21 | 0.78 | 1.87 | 3.13 | 1.79 | 0.14 | 1.32 |
| 1000 | — | 1.36 | 0.87 | 1.79 | 3.25 | 2.35 | 0.26 | 1.04 |
| — | 30 | 0.99 | 0.76 | 3.56 | 3.52 | 6.13 | 0.08 | 1.06 |

TABLE 13-continued

Percentage of CD8 cells expressing CD25 for each different stimulation condition

| Stimulation condition | | Percentage of CD8 cells expressing CD25 | | | | | | |
|---|---|---|---|---|---|---|---|---|
| [Anti-PD1] | [LAG-3Ig] | Donor | | | | | | |
| (ng/ml) | (ng/ml) | 1 | 2 | 3 | 4 | 5 | 6 | 7 |
| 30 | 30 | 1.84 | 0.73 | 5.59 | 4.67 | 7.80 | 0.39 | 1.36 |
| 1000 | 30 | 1.67 | 0.79 | 5.91 | 4.41 | 8.09 | 0.52 | 1.59 |

TABLE 14

Percentage of CD8 cells expressing any one of the three activation markers (LAG-3, CD69, or CD25) for each different stimulation condition

| Stimulation condition | | Percentage of CD8 cells expressing any one of the three activation markers (LAG-3, CD69, or CD25) | | | | | | |
|---|---|---|---|---|---|---|---|---|
| [Anti-PD1] | [LAG-3Ig] | Donor | | | | | | |
| (ng/ml) | (ng/ml) | 1 | 2 | 3 | 4 | 5 | 6 | 7 |
| — | — | 4.23 | 4.82 | 8.79 | 14.66 | 5.68 | 5.34 | 8.41 |
| 30 | — | 4.24 | 6.34 | 12.58 | 18.09 | 7.09 | 7.12 | 12.19 |
| 1000 | — | 4.51 | 8.07 | 13.77 | 18.25 | 7.76 | 8.65 | 12.68 |
| — | 30 | 6.43 | 6.97 | 9.52 | 14.02 | 17.17 | 8.44 | 12.11 |
| 30 | 30 | 9.04 | 6.09 | 15.39 | 19.75 | 19.13 | 13.14 | 14.11 |
| 1000 | 30 | 8.54 | 6.49 | 15.70 | 20.05 | 19.05 | 14.11 | 15.68 |

TABLE 15

Percentage of CD8 cells expressing all three activation markers (LAG-3, CD69, and CD25) for each different stimulation condition

| Stimulation condition | | Percentage of CD8 cells expressing all three activation markers (LAG-3, CD69, and CD25) | | | | | | |
|---|---|---|---|---|---|---|---|---|
| [Anti-PD1] | [LAG-3Ig] | Donor | | | | | | |
| (ng/ml) | (ng/ml) | 1 | 2 | 3 | 4 | 5 | 6 | 7 |
| — | — | 0.25 | 0.15 | 0.19 | 0.51 | 0.27 | 0.02 | 0.20 |
| 30 | — | 0.14 | 0.14 | 0.36 | 0.75 | 0.30 | 0.06 | 0.65 |
| 1000 | — | 0.23 | 0.16 | 0.39 | 0.93 | 0.42 | 0.08 | 0.41 |
| — | 30 | 0.20 | 0.13 | 0.61 | 0.80 | 0.87 | 0.02 | 0.54 |
| 30 | 30 | 0.35 | 0.22 | 1.29 | 1.56 | 1.40 | 0.19 | 0.66 |
| 1000 | 30 | 0.30 | 0.28 | 1.62 | 1.63 | 1.97 | 0.17 | 0.66 |

TABLE 16

Mean percentage of CD8 cells expressing LAG-3, CD69, CD25, any one of the three activation markers (LAG-3, CD69, or CD25), or all three of the activation markers (LAG-3, CD69, and CD25) for each different stimulation condition

| Stimulation condition | | Mean percentage of CD8 cells expressing activation marker(s) | | | | |
|---|---|---|---|---|---|---|
| [Anti-PD1] (ng/ml) | [LAG-3Ig] (ng/ml) | LAG-3 | CD69 | CD25 | Any one | All three |
| — | — | 0.66 | 6.97 | 1.12 | 7.42 | 0.23 |
| 30 | — | 0.92 | 9.14 | 1.46 | 9.66 | 0.34 |
| 1000 | — | 1.07 | 9.96 | 1.56 | 10.53 | 0.37 |
| — | 30 | 1.17 | 9.96 | 2.30 | 10.66 | 0.45 |
| 30 | 30 | 1.83 | 12.95 | 3.20 | 13.81 | 0.81 |
| 1000 | 30 | 2.23 | 13.25 | 3.28 | 14.23 | 0.95 |

TABLE 17

Increase in mean percentage of CD8 cells expressing LAG-3, CD69, CD25, any one of the three activation markers (LAG-3, CD69, or CD25), or all three of the activation markers (LAG-3, CD69, and CD25) above mean background for each different stimulation condition

| Stimulation condition | | Mean percentage of CD8 cells expressing activation marker(s) | | | | |
|---|---|---|---|---|---|---|
| [Anti-PD1] (ng/ml) | [LAG-3Ig] (ng/ml) | LAG-3 | CD69 | CD25 | Any one | All three |
| 30 | — | 0.26 | 2.17 | 0.34 | 2.24 | 0.11 |
| 1000 | — | 0.41 | 2.99 | 0.44 | 3.11 | 0.14 |
| — | 30 | 0.51 | 2.99 | 1.18 | 3.24 | 0.23 |
| 30 | 30 | 1.17 | 5.98 | 2.08 | 6.39 | 0.58 |
| 1000 | 30 | 1.57 | 6.28 | 2.16 | 6.81 | 0.72 |

The results show that stimulation with 30 ng/ml anti-PD-1 antibody and 30 ng/ml LAG-3Ig, or 1000 ng/ml anti-PD-1 antibody and 30 ng/ml LAG-3Ig, resulted in a synergistic increase in the mean percentage of CD8 cells expressing any, or all three of the activation markers.

The results also show that stimulation with 30 ng/ml anti-PD-1 antibody and 30 ng/ml LAG-3Ig resulted in significantly higher mean percentage of CD8 cells expressing any, or all three of the activation markers than stimulation with 1000 ng/ml anti-PD-1 antibody.

It was concluded from these results that in vitro $CD8^+$ T cell response (as measured by expression of T cell activation markers) induced by relatively low doses of anti-PD1 antibody is synergistically increased by a soluble LAG-3 derivative. It was also concluded that a dramatically improved in vitro $CD8^+$ T cell response is obtained using over 30 times less anti-PD1 antibody if this is combined with a soluble LAG-3 derivative.

Since PD-1 pathway inhibitors (such as Keytruda and Opdivo) are known to activate CD8+ T cells, and this activation is associated with anti-cancer effects, the results presented in the above examples provide evidence that improved anti-cancer effects may be obtained by co-administration of a PD-1 pathway inhibitor with a LAG-3 protein, or a derivative thereof that is able to bind to MHC class II molecules. Alternatively, similar anti-cancer effects may be achieved by co-administration of a PD-1 pathway inhibitor with a LAG-3 protein (or a derivative thereof that is able to bind to MHC class II molecules) at lower doses (for example, 10-30 times lower doses) of the PD-1 pathway inhibitor compared with administration of the PD-1 pathway inhibitor as a monotherapy. Such co-administration is expected to reduce the side effects caused by the PD-1 pathway inhibitor.

Similarly, since activation of $CD8^+$ T cells is also known to be effective against infection, including chronic or persistent infection, the results presented in the above examples also provide evidence that co-administration of a PD-1 pathway inhibitor with a LAG-3 protein, or a derivative thereof that is able to bind to MHC class II molecules, can be used to prevent, treat or ameliorate infection more effectively. Alternatively, similar effects against infection may be achieved by co-administration of a PD-1 pathway inhibitor with a LAG-3 protein (or a derivative thereof that is able to bind to MHC class II molecules) at lower doses (for example, 30 to 100 times lower doses) of the PD-1 pathway inhibitor compared with administration of the PD-1 pathway inhibitor as a monotherapy. Such co-administration is expected to reduce the side effects caused by the PD-1 pathway inhibitor.

Example 5

Binding of LAG-3 Derivatives to MHC Class II-Positive Cells

Several derivatives of LAG-3 were tested for their ability to bind to MHC class 11-positive cells:

i) domains D1-D4 of LAG-3 linked to immunoglobulin Fc (Ig Fc) sequence by a first linker (LAG-3 D1D4-linker1-Ig, sLAG-3 D1D4-Ig, LAG-3Ig, or IMP321);

ii) domains D1-D4 of LAG-3, linked to Ig Fc sequence by a second linker (LAG-3 D1D4-linker2-Ig, or sLAG-3 D1D4-linkerB-Ig);

iii) domains D1 and D2 of LAG-3, linked to Ig Fc sequence by the second linker (LAG-3 D1D2-linker2-Ig, or sLAG-3 D1D2-linkerB-Ig); and iv) domains D1-D4 of LAG-3 linked to Ig Fc sequence by the first linker, but with a mutation in the MHC class II binding site of the D1 domain of LAG-3, at position R75 (R75A), which enhances binding to MHC class II molecules by three-fold or more (Huard et al., Proc. Natl. Acad. Sci. USA, 1997, 94:5744) (IMP321 R75A).

Figure 7:
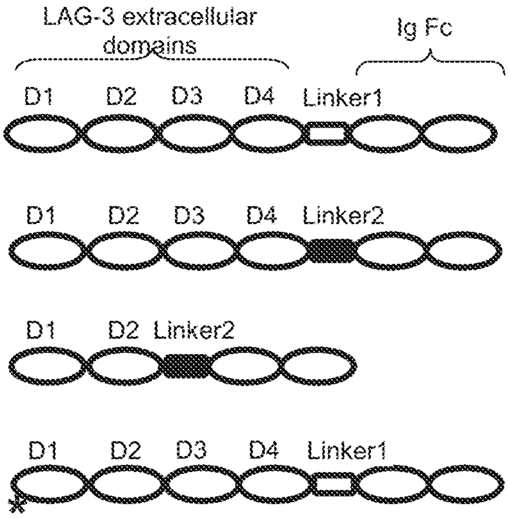
FIG. 7. Shows an illustration of derivatives of LAG-3 protein fused to Immunoglobulin Fc (IgFc) sequence.

The derivatives are illustrated in FIG. 7.

Figures 8A, 8B:
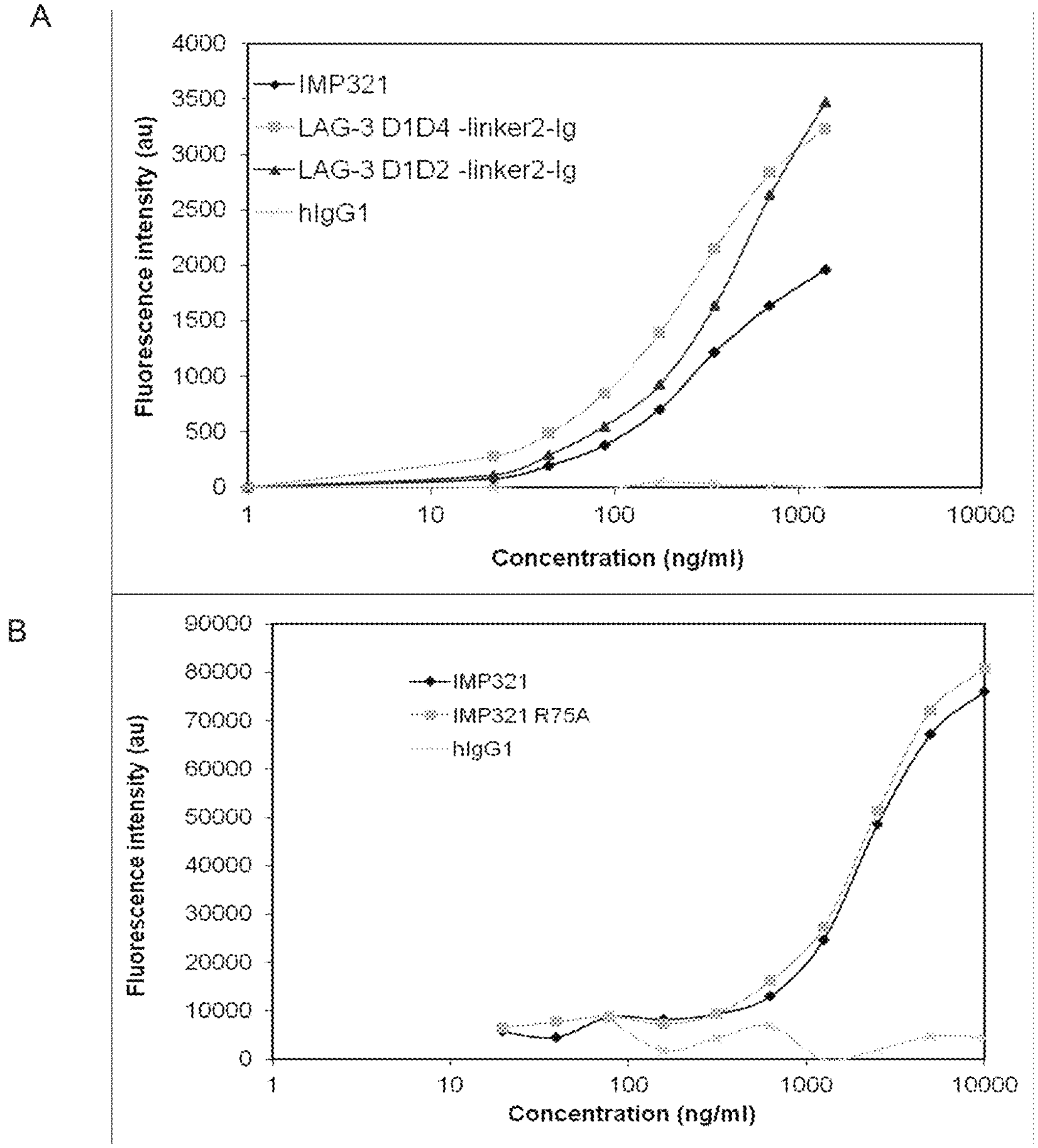
FIGS. 8A-8B. Show binding of LAG-3 derivatives to MHC class 11-positive cells. (A) Comparison of IMP321 with LAG-3 D1D4-linker2-IG, LAG-3 D1D2-linker2-Ig and hIG1. (B) Comparison of IMP321 with IMP321 R75A and hIG1.

MHC class II+ Raji cells were incubated for 45 minutes at 4° C. with various concentrations of the LAG-3 derivatives, or with a human IgG1 antibody (hIgG1) as a negative control. The LAG-3 molecules bound to the cell surface were revealed with a FITC-conjugated goat anti-mouse Ig (Coulter). The cells were analyzed by flow cytometry. The results, expressed as fluorescence intensity units, are shown in FIG. 8. The results show that all of the LAG-3 derivatives bound to MHC class II-positive cells.

Example 6

Figure 9:
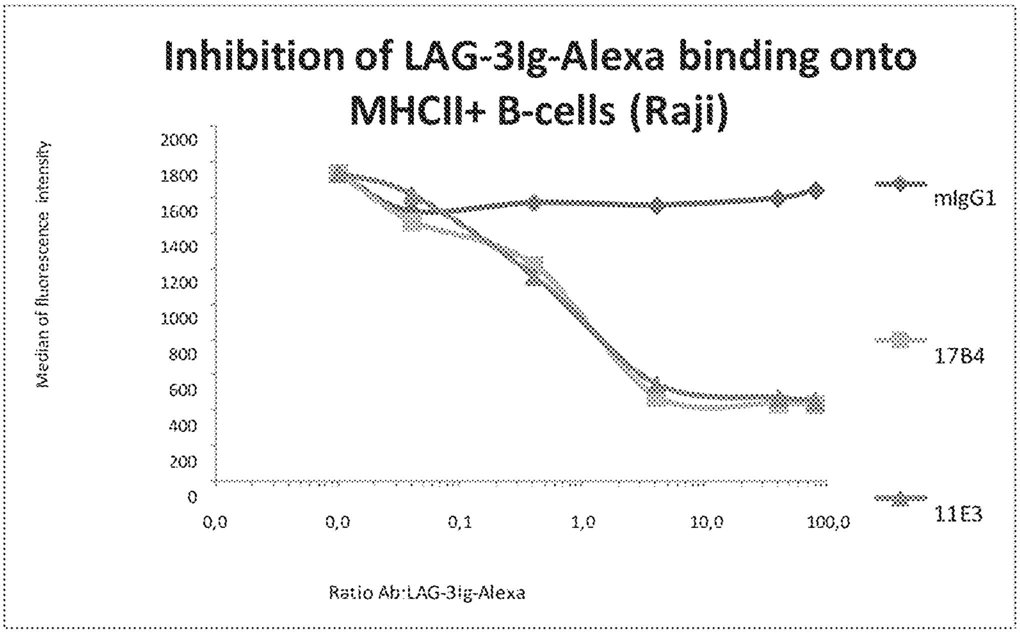
FIG. 9. Shows inhibition of binding of a LAG-3 derivative to MHC class 11-positive cells by antibodies that block binding of LAG-3 to MHC class II molecules.

Inhibition of Binding of the LAG-3 Derivative IMP321 to MHC Class II-Positive Cells by Antibodies that Block Binding of LAG-3 to MHC Class II Molecules 17B4 and 11E3 are anti-LAG-3 monoclonal antibodies that are known to block binding of LAG-3 to MHC class II molecules. Binding of an IMP321 conjugate (LAG-3Ig-Alexa 488) to MHC class II-positive B cells (Raji cells) was determined following pre-incubation of the conjugate (4 μg/ml at 4° C.) with 17B4 or 11E3 blocking antibody, or with an isotype-matched negative control monoclonal antibody (mIgG1). Analysis of cell-bound fluorescence was carried out using fluorescence-activated cell sorting (FACS). The results are shown in FIG. 9.

The results show that binding of IMP321 to Raji cells was inhibited by LAG-3-specific monoclonal antibody that blocks binding of LAG-3 to MHC class II molecules.

Example 7

Activation of Monocytes by LAG-3 Derivatives

Figures 5A, 5B, 5C:
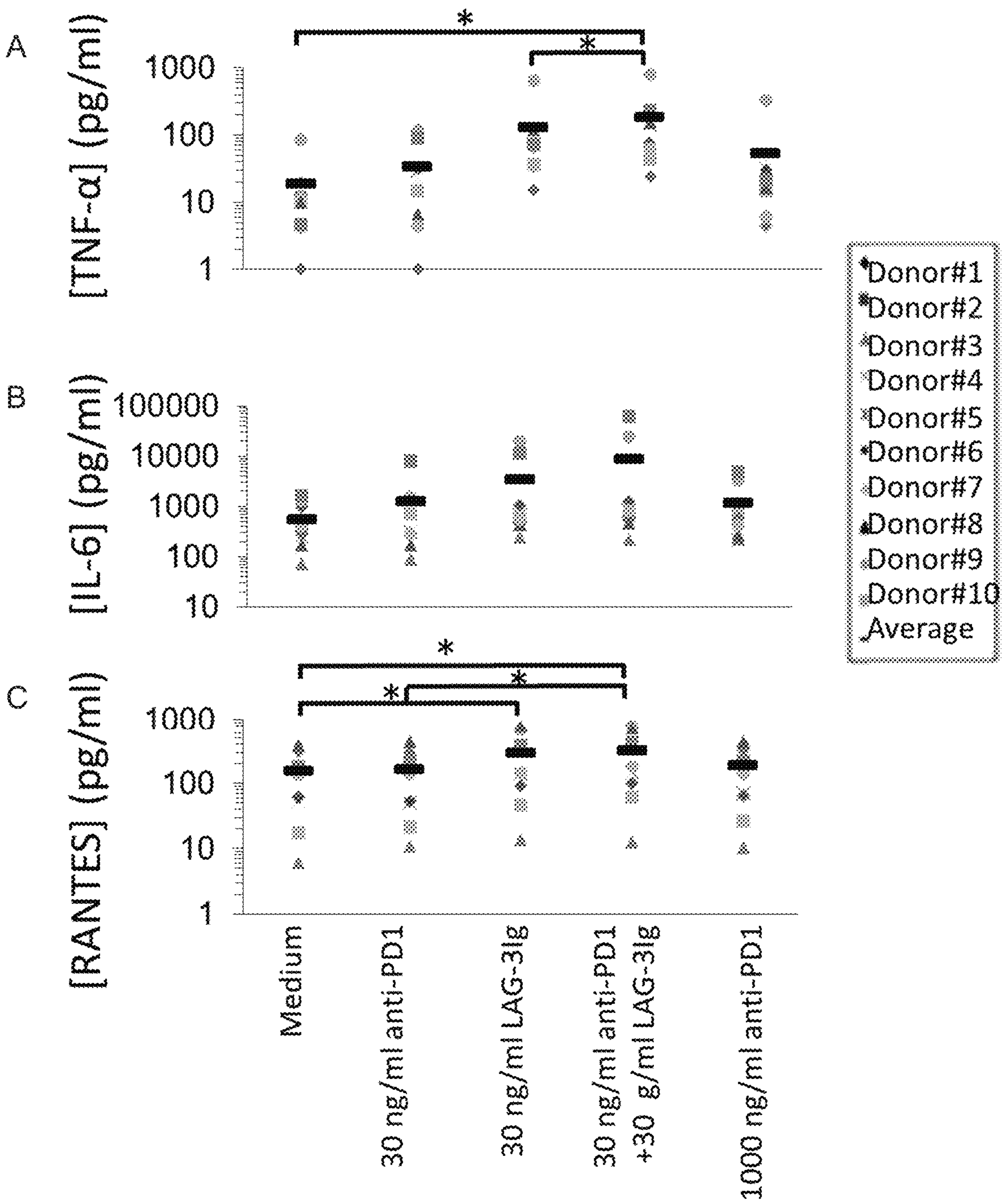
FIGS. 5A-5C. Show the effect of LAG-3Ig and anti-PD1 antibody on the secretion of (A) TNFα, (B) IL-6, and (C) RANTES induced by antigenic stimulation.
Figure 10A:
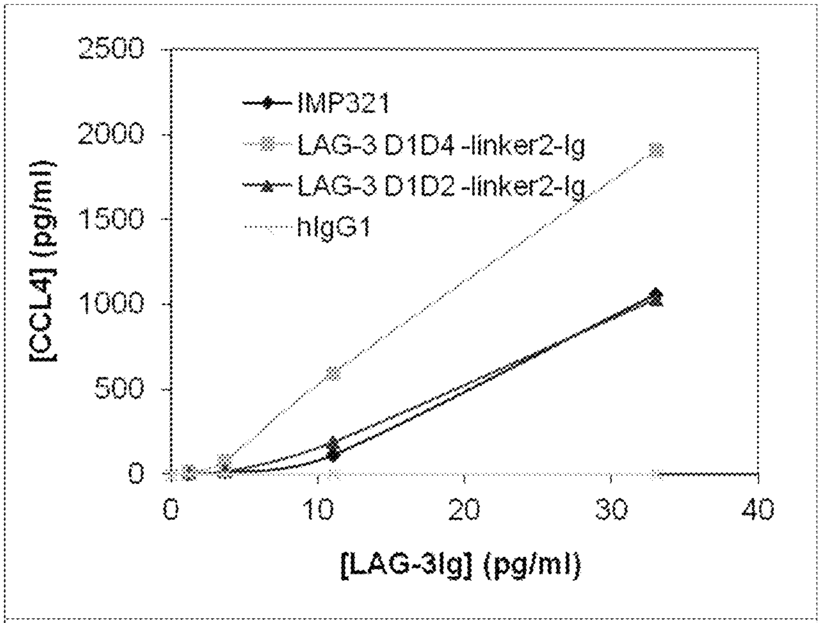
FIGS. 10A-10B. Show activation of THP-1 cells by LAG-3 derivatives, as determined by CCL4 secretion. (A) Comparison of IMP321 with LAG-3 D1D4-linker2-IG, LAG-3 D1D2-linker2-Ig and hIG1. (B) Comparison of IMP321 with IMP321 R75A and hIG1.
Figure 10B:
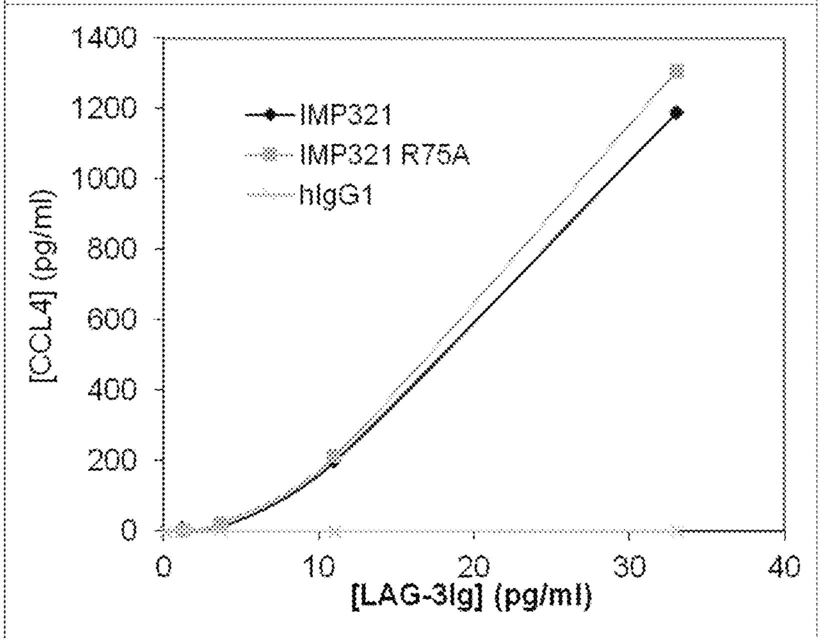
Figure 11A:
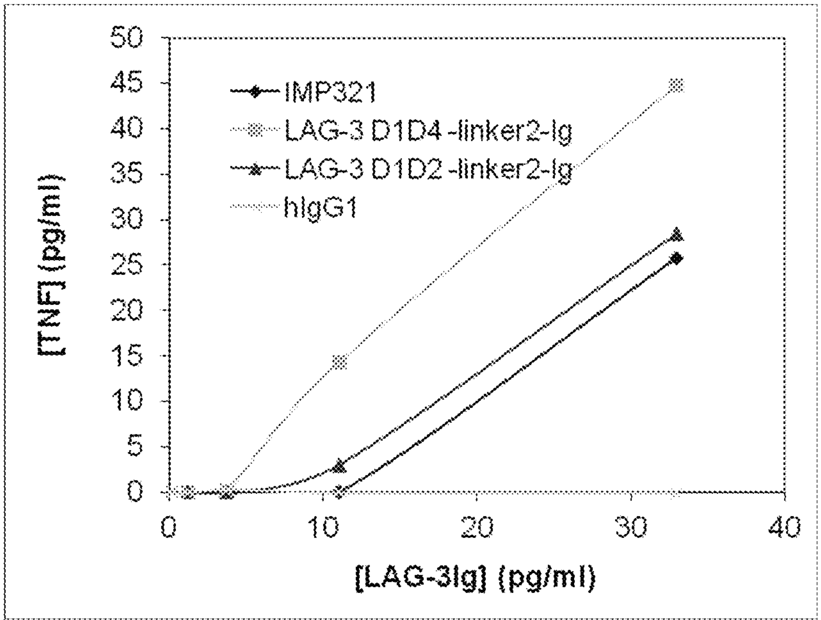
FIGS. 11A-11B. Show activation of THP-1 cells by LAG-3 derivatives, as determined by TNF-α secretion. (A) Comparison of IMP321 with LAG-3 D1D4-linker2-IG, LAG-3 D1D2-linker2-Ig and hIG1. (B) Comparison of IMP321 with IMP321 R75A and hIG1.
Figure 11B:
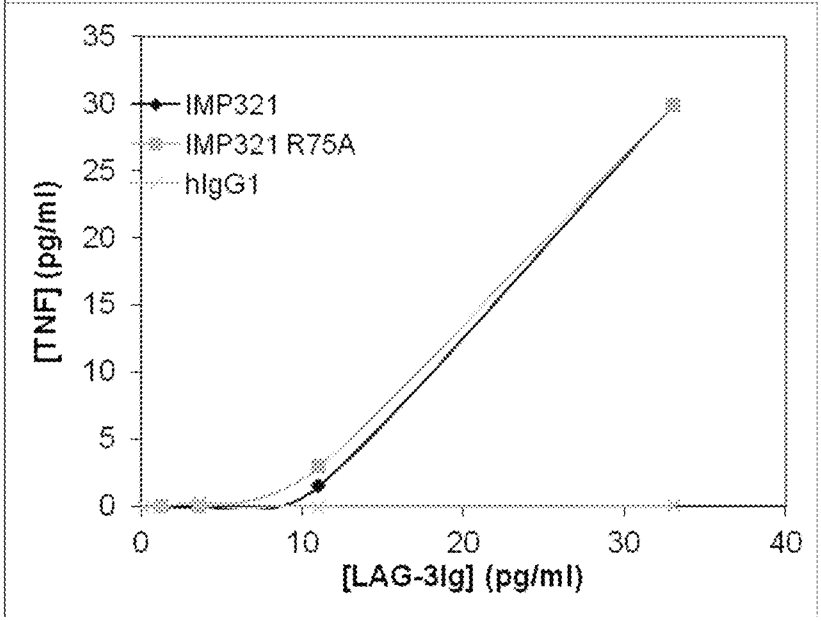

THP-1 cells were incubated for 4 hours at 4° C. with the LAG-3 derivatives illustrated in FIG. 5, or with human IgG1 as a negative control. The amount of secretion by the THP-1 cells of the chemokine CCL4, and the cytokine Tumor Necrosis Factor-α, TNF-α, was determined, and was used as a measure of monocyte activation. CCL4 and TNF-α secretion was quantified in the cell supernatants using a Cytometric Beads Array. The results of the CCL4 determinations are shown in FIG. 10, and the results of the TNF-α determinations are shown in FIG. 11.

The results show that the LAG-3 derivatives were all able to activate THP-1 monocytic cells.

Example 8

Figure 12A:
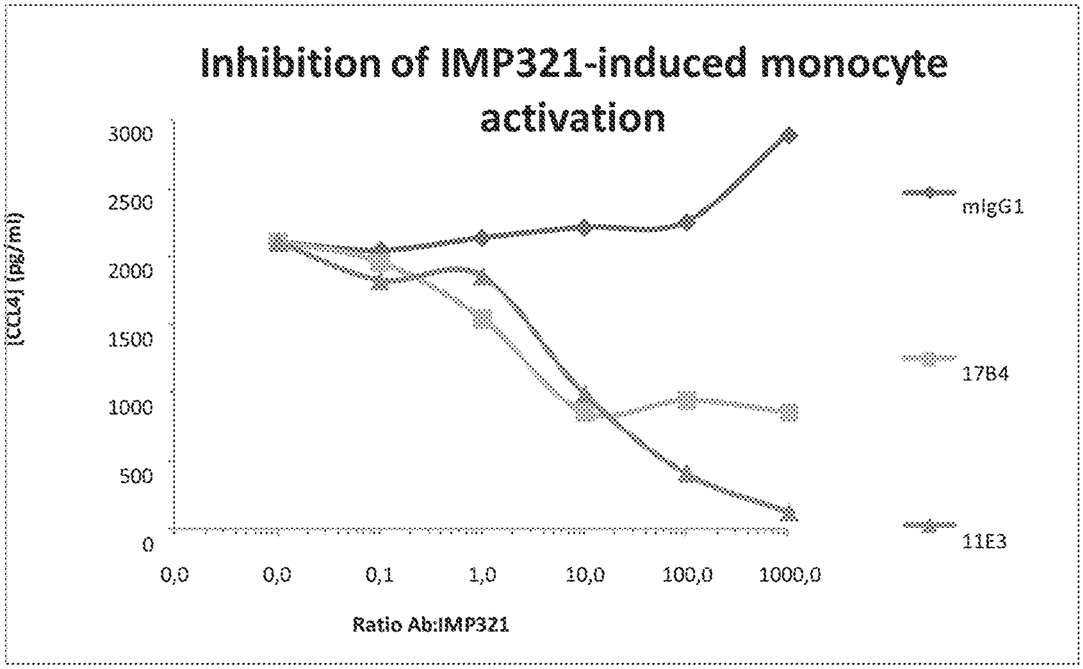
FIGS. 12A-12B. (A) & (B) Inhibition of LAG derivative-induced monocyte activation by antibodies that block binding of LAG-3 to MHC class II molecules (17B4 and 11E3).
Figure 12B:
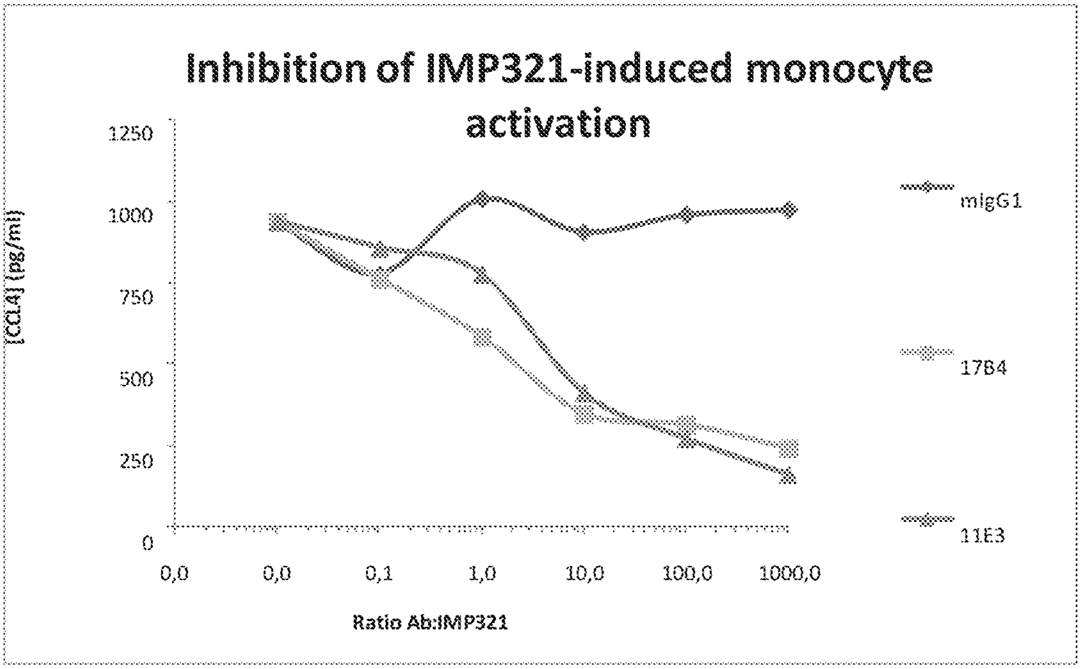

Inhibition of IMP321-Induced Monocyte Activation by Antibodies that Block Binding of LAG-3 to MHC Class II Molecules IMP321 (20 ng/ml) was preincubated with 17B4 or 11E3 antibody (5 minutes at 37° C.), before incubation of the mixture with THP-1 cells for 4 hours at 37° C. The amount of CCL4 secretion by the THP-1 cells was used to determine the level of monocyte activation. The results of two experiments are shown in FIG. 12.

The results demonstrate that IMP321-induced monocyte activation is inhibited by the blocking anti-LAG-3 mAbs 17B4 and 11E3. This indicates that the ability of IMP321 to activate monocytes is dependent on binding of IMP321 to MHC class II molecules.

Example 9

Activation of Primary Antigen-Presenting Cells (APCs) by LAG-3 Derivatives

Figure 13:
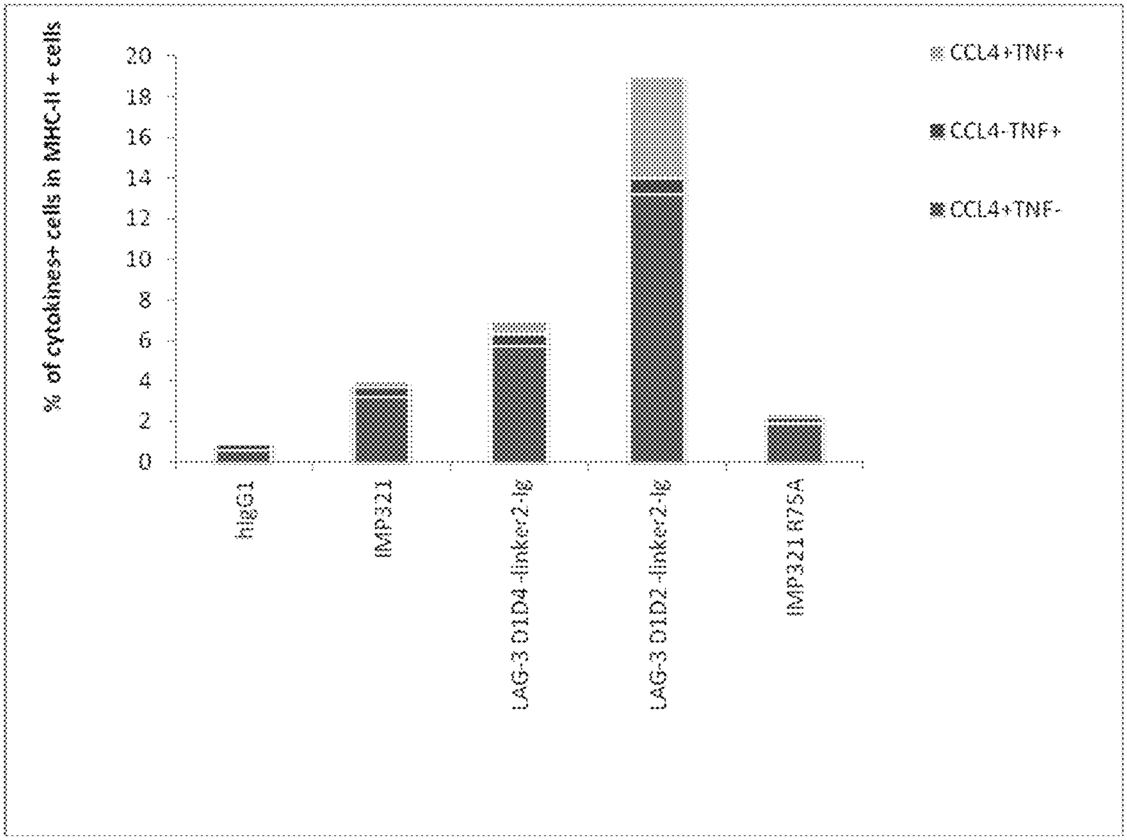
FIG. 13. Shows activation of antigen-presenting cells (APCs) by LAG-3 derivatives.

Human peripheral blood mononuclear cells (PBMCs) were incubated for 4 hours at 37° C. with the LAG-3 derivatives illustrated in FIG. 7, or with human IgG1 as a negative control, in the presence of brefeldin, a secretion inhibitor. The cytokine response of the APCs present in the PBMCs was determined by intracellular staining of CCL4, a chemokine known to favour the Th1 and CD8-positive response, and TNF-α, a multifunctional cytokine which directly inhibits tumorigenesis. The results were analyzed by cytometry. The results, represented by the percentage of cells expressing CCL4 and/or TNF-α in MHC class II-positive cells, are shown in FIG. 13.

The results show that all the LAG-3 derivatives tested induced the production of CCL4, and TNF-α in primary APCs.

Example 10

Activation of $CD8^+$ T Cells by LAG-3 Derivatives

Figure 14:
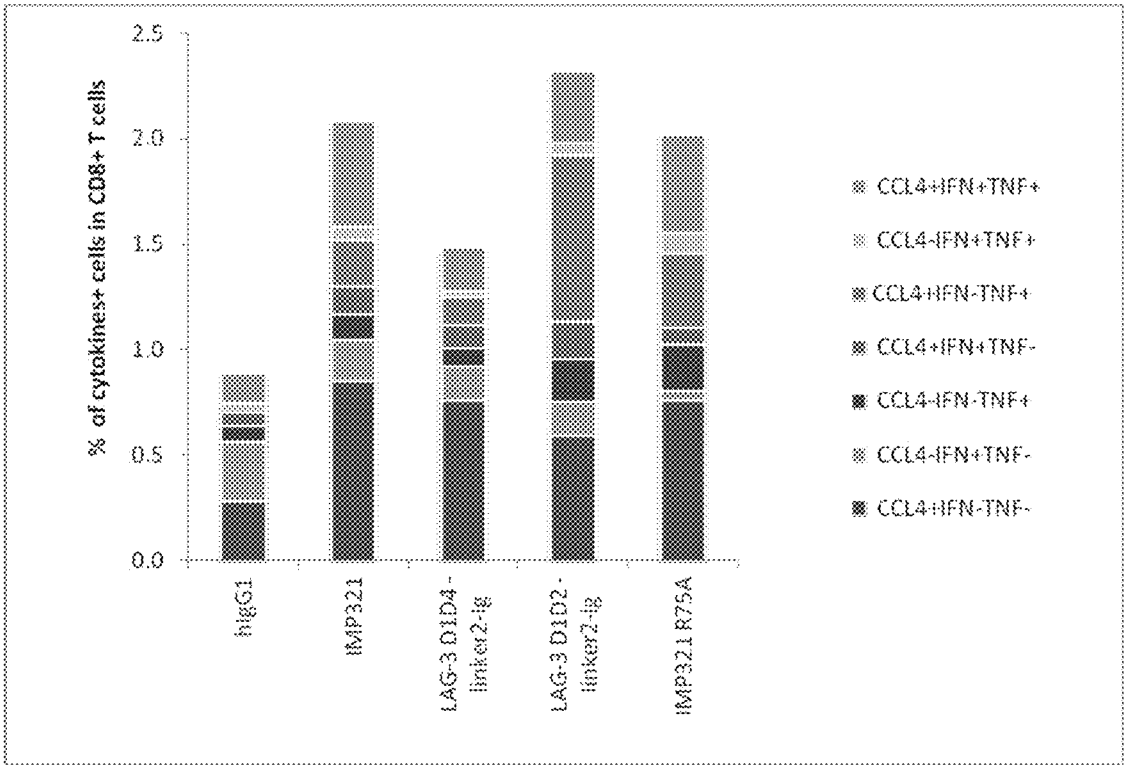
FIG. 14. Shows activation of CD8-positive T cells by LAG-3 derivatives.

Human PBMCs were incubated for 18 hours with the LAG-3 derivatives illustrated in FIG. 7, or with human IgG1 as a negative control. Brefeldin was present for the last 16 hours of the incubation. The cytokine response of $CD8^+$ T cells after 18 hour exposure to LAG-3 derivatives was followed by intracellular staining of CCL4, IFN-γ and TNF-α and analyzed by cytometry. The results, represented as the percentage of cells expressing CCL4, IFN-γ and/or TNF-α in $CD3^+/CD8^+$ T cells, are shown in FIG. 14.

The results show that all of the LAG-3 derivatives tested induced activation of Type 1 cytotoxic CD8-positive T cells (Tc1 cells). It is concluded that, through binding to MHC class II molecules expressed by APCs, the LAG-3 derivatives induced activation of Tc1 cells. Activation of Tc1 cells forms the main anti-tumor immune response.

Example 11

Effect of LAG-3Ig and Anti-PD-L1 on the Expression of Activation Markers Induced by Antigenic Stimulation This example demonstrates the effect of a soluble derivative of LAG-3 (LAG-3Ig), and an anti-PD-L1 antibody, on the expression of T cell activation markers.

PBMCs from 12 healthy donors ($0.2\times10^6$ cells/well, at 1M/ml in complete RPMI+10% FBS) were incubated with a pool of peptides covering the sequence of CMV pp35 in triplicate, without any additive (Medium), with 30 ng/ml or 3000 ng/ml of anti-PD-L1 humanized antibody (BPS Bioscience, catalog #71213), with 30 ng/ml LAG-3Ig, or with 30 ng/ml of LAG-3Ig and 30 ng/ml of anti-PD-L1 antibody.

The T cell response was evaluated by phenotyping the cells for the expression of three activation markers (LAG-3, CD69 and CD25) three days post-stimulation by flow cytometry.

Figures 16A, 16B, 16C:
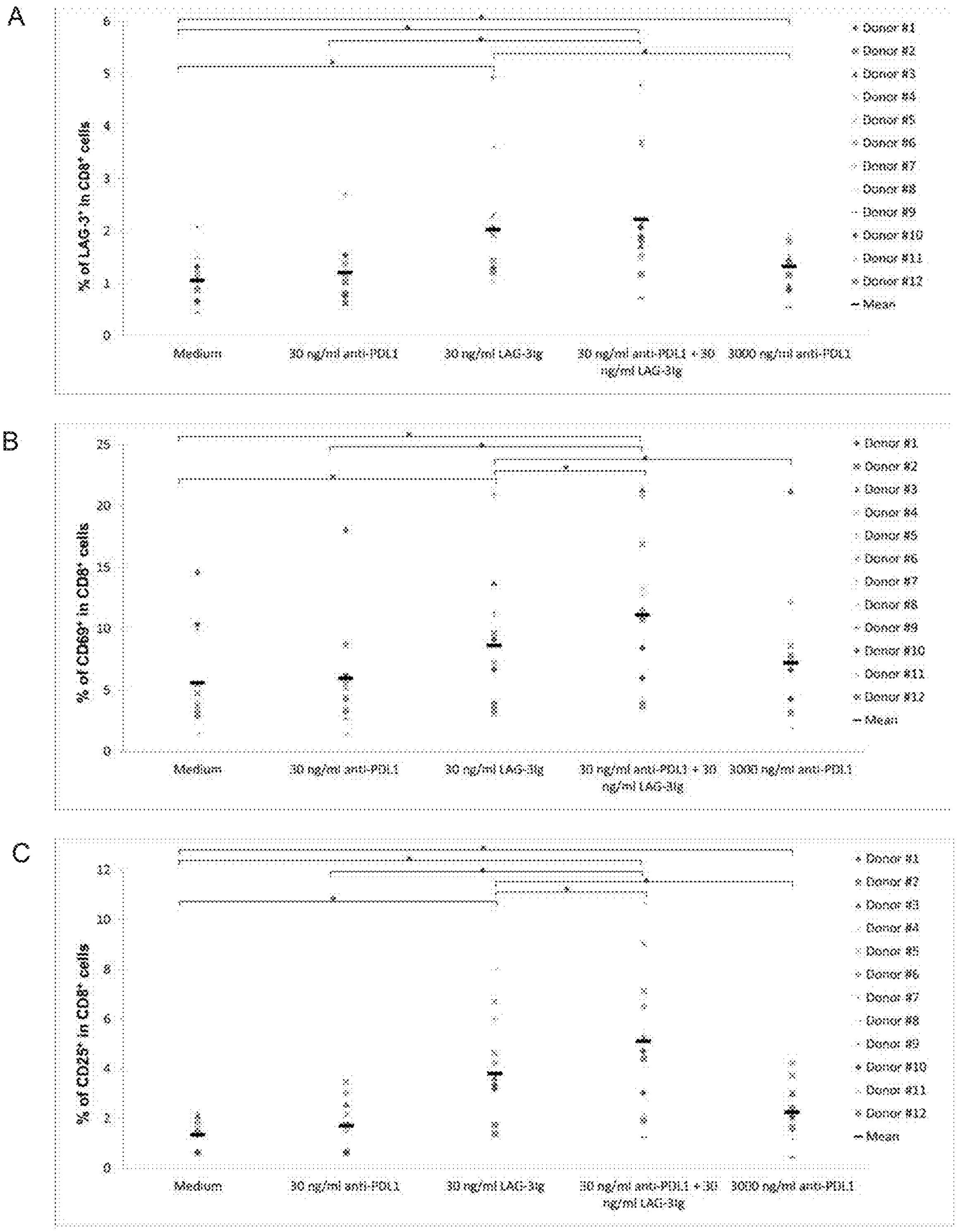
FIGS. 16A-16E. Show the effect of LAG-3Ig and anti-PD-L1 antibody on the expression of activation markers induced by antigenic stimulation. (A) Percent (%) of Lag3+ in CD8+ cells; (B) % of CD69+ in CD8+ cells; (C) % of CD25 in CD8+ cells; (D) % of activation markers in CD8+ cells; (E) % of Lag3+, CD69+, CD25+ in CD8+ cells.
Figure 16D:
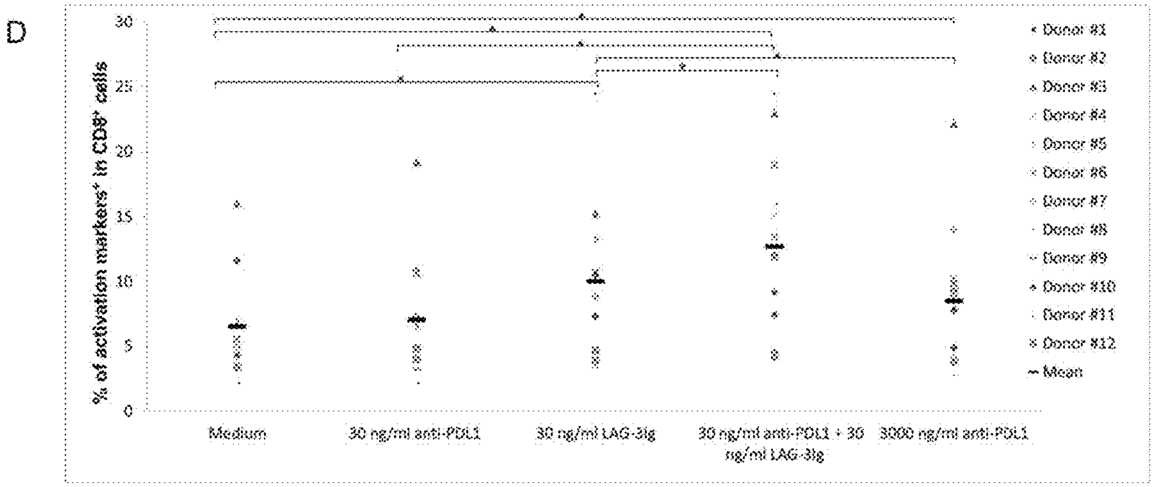
Figure 16E:
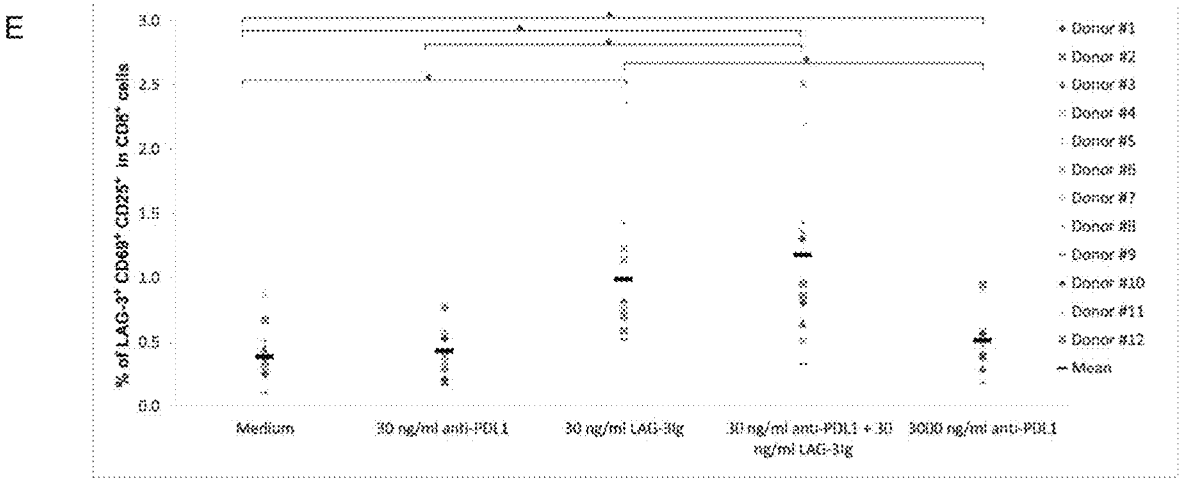

The percentage of CD8 cells expressing LAG-3, CD69 or CD25, at least one of the three activation markers (LAG-3, CD69 or CD25), or all three of the activation markers (LAG-3, CD69 and CD25), in the pooled triplicates, for each condition of stimulation, is recorded in Tables 18-22 below. The means of the results obtained for the 12 donors are shown in Table 23, and the increase of the means above mean background is shown in Table 24. The results for each donor are also plotted in FIG. 16, and the statistical differences (*$p<0.05$) are shown in black.

TABLE 18

Percentage of CD8 cells expressing LAG-3 for each different stimulation condition

| Stimulation condition | | Percentage of CD8 cells expressing LAG-3 | | | | | | | | | | | |
|---|---|---|---|---|---|---|---|---|---|---|---|---|---|
| [Anti-PD-L1] | [LAG-3Ig] | Donor | | | | | | | | | | | |
| (ng/ml) | (ng/ml) | 1 | 2 | 3 | 4 | 5 | 6 | 7 | 8 | 9 | 10 | 11 | 12 |
| — | — | 1.33 | 0.65 | 1.07 | 0.86 | 1.11 | 1.21 | 2.08 | 0.83 | 0.45 | 0.67 | 1.52 | 0.90 |
| 30 | — | 1.54 | 0.81 | 0.63 | 1.39 | 1.18 | 1.36 | 2.70 | 1.11 | 0.66 | 0.76 | 1.22 | 1.02 |
| — | 30 | 2.05 | 1.44 | 2.07 | 1.92 | 2.29 | 1.43 | 4.93 | 3.60 | 1.01 | 1.29 | 1.05 | 1.22 |

TABLE 18-continued

| Percentage of CD8 cells expressing LAG-3 for each different stimulation condition | | | | | | | | | | | | | |
|---|---|---|---|---|---|---|---|---|---|---|---|---|---|
| Stimulation condition | | Percentage of CD8 cells expressing LAG-3 | | | | | | | | | | | |
| [Anti-PD-L1] | [LAG-3Ig] | Donor | | | | | | | | | | | |
| (ng/ml) | (ng/ml) | 1 | 2 | 3 | 4 | 5 | 6 | 7 | 8 | 9 | 10 | 11 | 12 |
| 30 | 30 | 2.06 | 1.83 | 1.72 | 2.14 | 3.69 | 1.53 | 4.79 | 3.62 | 0.72 | 1.89 | 1.49 | 1.17 |
| 3000 | — | 1.43 | 1.16 | 0.95 | 1.36 | 1.50 | 1.79 | 1.84 | 1.13 | 0.55 | 0.87 | 1.92 | 1.37 |

TABLE 19

| Percentage of CD8 cells expressing CD69 for each different stimulation condition | | | | | | | | | | | | | |
|---|---|---|---|---|---|---|---|---|---|---|---|---|---|
| Stimulation condition | | Percentage of CD8 cells expressing CD69 | | | | | | | | | | | |
| [Anti-PD-L1] | [LAG-3Ig] | Donor | | | | | | | | | | | |
| (ng/ml) | (ng/ml) | 1 | 2 | 3 | 4 | 5 | 6 | 7 | 8 | 9 | 10 | 11 | 12 |
| — | — | 10.33 | 2.91 | 14.62 | 4.70 | 5.49 | 3.44 | 9.91 | 1.46 | 3.11 | 3.93 | 4.09 | 2.99 |
| 30 | — | 6.19 | 4.32 | 18.07 | 8.70 | 5.21 | 5.58 | 8.79 | 1.40 | 2.69 | 3.43 | 3.54 | 3.28 |
| — | 30 | 9.15 | 3.79 | 13.73 | 9.63 | 11.16 | 7.24 | 20.89 | 11.01 | 4.04 | 6.70 | 3.08 | 3.28 |
| 30 | 30 | 5.96 | 10.79 | 21.35 | 13.21 | 16.88 | 11.55 | 20.82 | 12.70 | 3.53 | 8.44 | 4.23 | 3.88 |
| 3000 | — | 6.62 | 7.79 | 21.20 | 7.31 | 8.61 | 7.19 | 12.14 | 1.93 | 3.20 | 4.27 | 3.21 | 3.17 |

TABLE 20

| Percentage of CD8 cells expressing CD25 for each different stimulation condition | | | | | | | | | | | | | |
|---|---|---|---|---|---|---|---|---|---|---|---|---|---|
| Stimulation condition | | Percentage of CD8 cells expressing CD25 | | | | | | | | | | | |
| [Anti-PD-L1] | [LAG-3Ig] | Donor | | | | | | | | | | | |
| (ng/ml) | (ng/ml) | 1 | 2 | 3 | 4 | 5 | 6 | 7 | 8 | 9 | 10 | 11 | 12 |
| — | — | 1.78 | 0.63 | 2.14 | 1.45 | 1.59 | 1.89 | 1.59 | 0.65 | 0.64 | 0.61 | 1.74 | 1.36 |
| 30 | — | 1.54 | 0.62 | 2.57 | 3.47 | 2.16 | 3.02 | 1.71 | 0.76 | 0.71 | 0.62 | 1.60 | 1.74 |
| — | 30 | 3.34 | 1.73 | 3.64 | 4.61 | 6.71 | 4.23 | 5.99 | 8.03 | 1.34 | 3.18 | 1.38 | 1.37 |
| 30 | 30 | 3.03 | 4.41 | 5.19 | 7.13 | 9.03 | 6.50 | 5.30 | 10.65 | 1.25 | 4.70 | 2.18 | 1.91 |
| 3000 | — | 2.06 | 2.42 | 3.00 | 3.72 | 3.00 | 4.24 | 1.95 | 1.18 | 0.43 | 1.57 | 1.64 | 1.65 |

TABLE 21

| Percentage of CD8 cells expressing any one of the three activation markers (LAG-3, CD69, or CD25) for each different stimulation condition | | | | | | | | | | | | | |
|---|---|---|---|---|---|---|---|---|---|---|---|---|---|
| Stimulation condition | | Percentage of CD8 cells expressing any one of the three activation markers (LAG-3, CD69, or CD25) | | | | | | | | | | | |
| [Anti-PD-L1] | [LAG-3Ig] | Donor | | | | | | | | | | | |
| (ng/ml) | (ng/ml) | 1 | 2 | 3 | 4 | 5 | 6 | 7 | 8 | 9 | 10 | 11 | 12 |
| — | — | 11.59 | 3.34 | 15.98 | 5.53 | 6.84 | 4.97 | 11.58 | 2.15 | 3.50 | 4.27 | 4.79 | 3.38 |
| 30 | — | 7.22 | 4.81 | 19.17 | 10.62 | 6.55 | 7.28 | 10.97 | 2.14 | 3.21 | 3.92 | 4.09 | 3.99 |
| — | 30 | 10.52 | 4.66 | 15.20 | 10.75 | 13.22 | 8.79 | 24.48 | 13.28 | 4.47 | 7.26 | 3.47 | 3.88 |
| 30 | 30 | 7.42 | 11.95 | 22.97 | 15.16 | 18.99 | 13.42 | 24.43 | 15.94 | 3.98 | 9.11 | 4.62 | 4.40 |
| 3000 | — | 7.77 | 9.22 | 22.14 | 9.82 | 10.16 | 8.93 | 13.95 | 2.78 | 3.56 | 4.83 | 4.21 | 3.78 |

TABLE 22

Percentage of CD8 cells expressing all three activation markers (LAG-3, CD69, and CD25) for each different stimulation condition

| Stimulation condition [Anti-PD-L1] (ng/ml) | [LAG-3Ig] (ng/ml) | Percentage of CD8 cells expressing all three activation markers (LAG-3, CD69, and CD25) Donor 1 | 2 | 3 | 4 | 5 | 6 | 7 | 8 | 9 | 10 | 11 | 12 |
|---|---|---|---|---|---|---|---|---|---|---|---|---|---|
| — | — | 0.38 | 0.32 | 0.45 | 0.28 | 0.28 | 0.30 | 0.51 | 0.23 | 0.11 | 0.25 | 0.88 | 0.67 |
| 30 | — | 0.53 | 0.29 | 0.19 | 0.55 | 0.39 | 0.34 | 0.59 | 0.37 | 0.19 | 0.21 | 0.80 | 0.77 |
| — | 30 | 0.82 | 0.59 | 0.77 | 1.13 | 1.23 | 0.75 | 1.42 | 2.35 | 0.52 | 0.78 | 0.79 | 0.70 |
| 30 | 30 | 0.81 | 0.96 | 0.65 | 1.36 | 2.51 | 0.52 | 1.43 | 2.19 | 0.34 | 1.30 | 1.19 | 0.86 |
| 3000 | — | 0.57 | 0.40 | 0.29 | 0.58 | 0.49 | 0.52 | 0.50 | 0.39 | 0.18 | 0.39 | 0.92 | 0.95 |

TABLE 23

Mean percentage of CD8 cells expressing LAG-3, CD69, CD25, any one of the three activation markers (LAG-3, CD69, or CD25), or all three of the activation markers (LAG-3, CD69, and CD25) for each different stimulation condition

| Stimulation condition [Anti-PD-L1] (ng/ml) | [LAG-3Ig] (ng/ml) | Mean percentage of CD8 cells expressing activation marker(s) LAG-3 | CD69 | CD25 | Any one | All three |
|---|---|---|---|---|---|---|
| — | — | 1.06 | 5.58 | 1.34 | 6.49 | 0.39 |
| 30 | — | 1.20 | 5.93 | 1.71 | 7.00 | 0.43 |
| — | 30 | 2.03 | 8.64 | 3.80 | 10.00 | 0.99 |
| 30 | 30 | 2.22 | 11.11 | 5.10 | 12.70 | 1.18 |
| 3000 | — | 1.32 | 7.22 | 2.24 | 8.43 | 0.51 |

TABLE 24

Increase in mean percentage of CD8 cells expressing LAG-3, CD69, CD25, any one of the three activation markers (LAG-3, CD69, or CD25), or all three of the activation markers (LAG-3, CD69, and CD25) above mean background for each different stimulation condition

| Stimulation condition [Anti-PD-L1] (ng/ml) | [LAG-3Ig] (ng/ml) | Increase in mean percentage of CD8 cells expressing activation marker(s) LAG-3 | CD69 | CD25 | Any one | All three |
|---|---|---|---|---|---|---|
| 30 | — | 0.14 | 0.35 | 0.37 | 0.51 | 0.04 |
| — | 30 | 0.97 | 3.06 | 2.46 | 3.51 | 0.60 |
| 30 | 30 | 1.16 | 5.53 | 3.76 | 6.21 | 0.79 |
| 3000 | — | 0.26 | 1.64 | 0.90 | 1.94 | 0.12 |

The results show that stimulation with 30 ng/ml anti-PD-L1 antibody and 30 ng/ml LAG-3Ig, resulted in a synergistic increase in the mean percentage of CD8 cells expressing any, or all three of the activation markers.

The results also show that stimulation with 30 ng/ml anti-PD-L1 antibody and 30 ng/ml LAG-3Ig resulted in significantly higher mean percentage of CD8 cells expressing any, or all three of the activation markers than stimulation with 3000 ng/ml anti-PD-L1 antibody alone.

It was concluded from these results that in vitro $CD8^+$ T cell response (as measured by expression of T cell activation markers) induced by relatively low doses of anti-PD-L1 antibody is synergistically increased by a soluble LAG-3 derivative. It was also concluded that a dramatically improved in vitro $CD8^+$ T cell response is obtained using 100 times less anti-PD-L1 antibody if this is combined with a soluble LAG-3 derivative.

Since PD-1 pathway inhibitors (such as Keytruda and Opdivo) are known to activate CD8+ T cells, and this activation is associated with anti-cancer effects, the results presented in the above examples provide evidence that improved anti-cancer effects may be obtained by co-administration of a PD-1 pathway inhibitor with a LAG-3 protein, or a derivative thereof that is able to bind to MHC class II molecules. Alternatively, similar anti-cancer effects may be achieved by co-administration of a PD-1 pathway inhibitor with a LAG-3 protein (or a derivative thereof that is able to bind to MHC class II molecules) at lower doses (for example, 30 to 100 times lower doses) of the PD-1 pathway inhibitor compared with administration of the PD-1 pathway inhibitor as a monotherapy. Such co-administration is expected to reduce the side effects caused by the PD-1 pathway inhibitor.

Similarly, since activation of $CD8^+$ T cells is also known to be effective against infection, including chronic or persistent infection, the results presented in the above examples also provide evidence that co-administration of a PD-1 pathway inhibitor with a LAG-3 protein, or a derivative thereof that is able to bind to MHC class II molecules, can be used to prevent, treat or ameliorate infection more effectively. Alternatively, similar effects against infection may be achieved by co-administration of a PD-1 pathway inhibitor with a LAG-3 protein (or a derivative thereof that is able to bind to MHC class II molecules) at lower doses (for example, 30 to 100 times lower doses) of the PD-1 pathway inhibitor compared with administration of the PD-1 pathway inhibitor as a monotherapy. Such co-administration is expected to reduce the side effects caused by the PD-1 pathway inhibitor.

Example 12

Effect of LAG-3Ig and Various Anti-PD-1 or Anti-PD-L1 Antibodies on IFN-γ and TNF-α Production Induced by Antigenic Stimulation This example demonstrates the effect of a soluble derivative of LAG-3 (LAG-3Ig) and various different anti-PD-1 or anti-PD-L1 antibodies on T-cell activation in vitro using IFN-γ and TNF-α secretion assays.

PBMCs from healthy donors ($0.2\times10^6$ cells/well at 1M/ml in complete RPMI+10% FBS) were incubated with a pool of peptides covering the sequence of CMV pp35 in triplicate, without any additive (Medium), with 30 ng/ml or 1000 ng/ml of anti-PD-1 antibody (Ab1 or Ab2) or anti-PD-L1 antibody (Ab3, Ab4, Ab5 or Ab6), with 10 or 30 ng/ml LAG-3Ig, or with 10 or 30 ng/ml LAG-3Ig and 30 ng/ml anti-PD-1 or anti-PD-L1 antibody.

The T cell response was evaluated by measuring the concentration of IFN-γ and TNF in cell culture supernatant three days post stimulation using BD Cytometric Bead Array.

Anti-PD-1: Ab1 (clone MIH4 from BD Pharmingen, catalog #557823) and Ab2 (humanized anti-PD-1 from BPS bioscience, catalog #71120); Anti-PD-L1: Ab3 (clone MIH1 from eBioscience, catalog #16-5983-82), Ab4 (clone MIH5 from eBioscience catalog #16-5982-81), Ab5 (Clone 1-111A from eBioscience catalog #14-9971-81) and Ab6 (humanized anti-PD-L1 from BPS bioscience, catalog #71213).

Figures 17A, 17B, 17C, 17D:
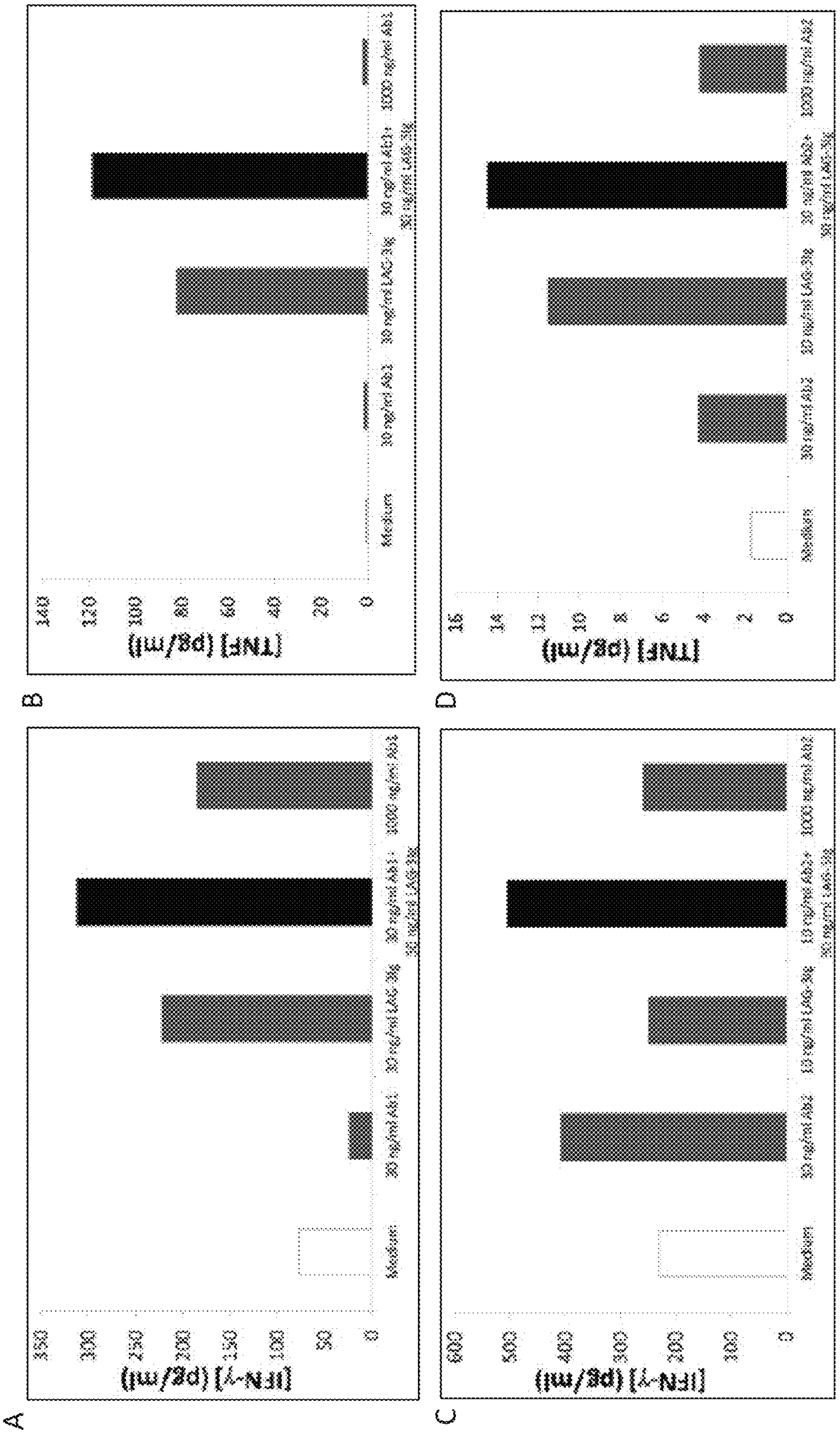
FIGS. 17A-17D. Show the effect of LAG-3Ig and different anti-PD-1 antibodies (Ab1 and Ab2) on the secretion of IFN-γ and TNF-α induced by antigenic stimulation. (A) Effect of Ab1 on IFN-γ; (B) Effect of Ab1 on TNF-α; (C) Effect of Ab2 on IFN-γ; (D) Effect of Ab2 on TNF-α.

The concentrations of IFN-γ and TNF-α in the pooled triplicates for each condition of stimulation for the anti-PD-1 antibodies are recorded in Table 25. The results are plotted in FIG. 17.

TABLE 25

Secretion of IFN-γ and TNF-α induced by antigen in the presence of anti-PD-1 antibody with and without LAG-3Ig

| Anti-PD-1 antibody | Stimulation condition [Anti-PD-1] (ng/ml) | [LAG-3Ig] (ng/ml) | Concentration (pg/ml) IFNγ | TNF-α | Increase in concentration (pg/ml) above background IFNγ | TNF-α |
|---|---|---|---|---|---|---|
| Ab1 | — | — | 77.7 | 0.2 | — | — |
| | 30 | — | 24.4 | 1.1 | −53.3 | 0.9 |
| | — | 30 | 222.3 | 82.4 | 144.6 | 82.2 |
| | 30 | 30 | 312.8 | 118.9 | 235.1 | 118.7 |
| | 1000 | | 185.4 | 1.8 | 107.7 | 1.6 |
| Ab2 | — | — | 230.8 | 1.692 | — | — |
| | 30 | — | 406.9 | 4.255 | 176.1 | 2.563 |
| | | 10 | 249.0 | 11.55 | 18.2 | 9.858 |
| | 30 | 10 | 504.6 | 14.47 | 273.8 | 12.778 |
| | 1000 | | 258.1 | 4.186 | 27.3 | 2.494 |

The results show that, for each anti-PD-1 antibody, secretion of IFN-γ was increased when the PBMCs were incubated in the presence of LAG-3Ig and lower concentrations of anti-PD-1 antibody, compared with anti-PD-1 antibody alone. For example, the increase in concentration of IFN-γ above the background level (i.e. the concentration of IFN-γ in the absence of anti-PD-1 and LAG-3Ig) in the presence of 30 ng/ml LAG-3Ig and 30 ng/ml Ab1 anti-PD-1 antibody, or 10 ng/ml LAG-3Ig and 30 ng/ml Ab2 anti-PD-1 antibody was greater than the sum of the corresponding increase in the presence of LAG-3Ig alone and 30 ng/ml anti-PD-1 antibody alone (i.e. for Ab1, 235.1>−53.3+144.6; for Ab2, 273.8>176.1+18.2). The effect of the combination of LAG-3Ig and each different anti-PD-1 antibody was, therefore, synergistic.

The results also show that secretion of IFN-γ induced by a combination of LAG-3Ig and a relatively low concentration of anti-PD-1 antibody (30 ng/ml) was much higher than secretion of IFN-γ induced by a much higher concentration (1000 ng/ml, over 30 times higher) of anti-PD-1 antibody alone (i.e. for Ab1, 235.1>107.7; for Ab2, 273.8>27.3).

Regarding TNF-α secretion, neither anti-PD-1 antibody alone (at relatively low or high concentration) had a significant effect on TNF-α secretion. However, for each anti-PD-1 antibody, secretion of TNF-α was increased when the PBMCs were incubated in the presence of LAG-3Ig and lower concentrations of anti-PD-1 antibody, compared with anti-PD-1 antibody alone. For example, the increase in concentration of TNF-α above the background level (i.e. the concentration of TNF-α in the absence of anti-PD-1 and LAG-3Ig) in the presence of 30 ng/ml LAG-3Ig and 30 ng/ml Ab1 anti-PD-1 antibody, or 10 ng/ml LAG-3Ig and 30 ng/ml Ab2 antibody was greater than the sum of the corresponding increase in the presence of LAG-3Ig alone and 30 ng/ml anti-PD-1 antibody alone (i.e. for Ab1, 118.7>0.9+82.2; for Ab2, 12.778>2.563+9.858). The effect of the combination of LAG-3Ig and each different anti-PD-1 antibody was, therefore, synergistic.

The results also show that secretion of TNF-α induced by a combination of LAG-3Ig and a relatively low concentration of anti-PD-1 antibody (30 ng/ml) was dramatically higher than secretion of TNF-α induced by a much higher concentration (1000 ng/ml, over 30 times higher) of anti-PD-1 antibody alone (i.e. for Ab1, 118.7>1.6; for Ab2, 12.778>2.494).

It was concluded from these results that in vitro T cell response (as measured by IFN-γ and TNF-α secretion) induced by relatively low doses of anti-PD-1 antibody is synergistically increased by a soluble LAG-3 derivative. It was also concluded that a significantly greater in vitro T cell response is obtained using over 30 times less anti-PD-1 antibody if this is combined with a soluble LAG-3 derivative. These effects were seen with different anti-PD-1 antibodies.

Figures 18A, 18B, 18C, 18D, 18E, 18F, 18G, 18H:
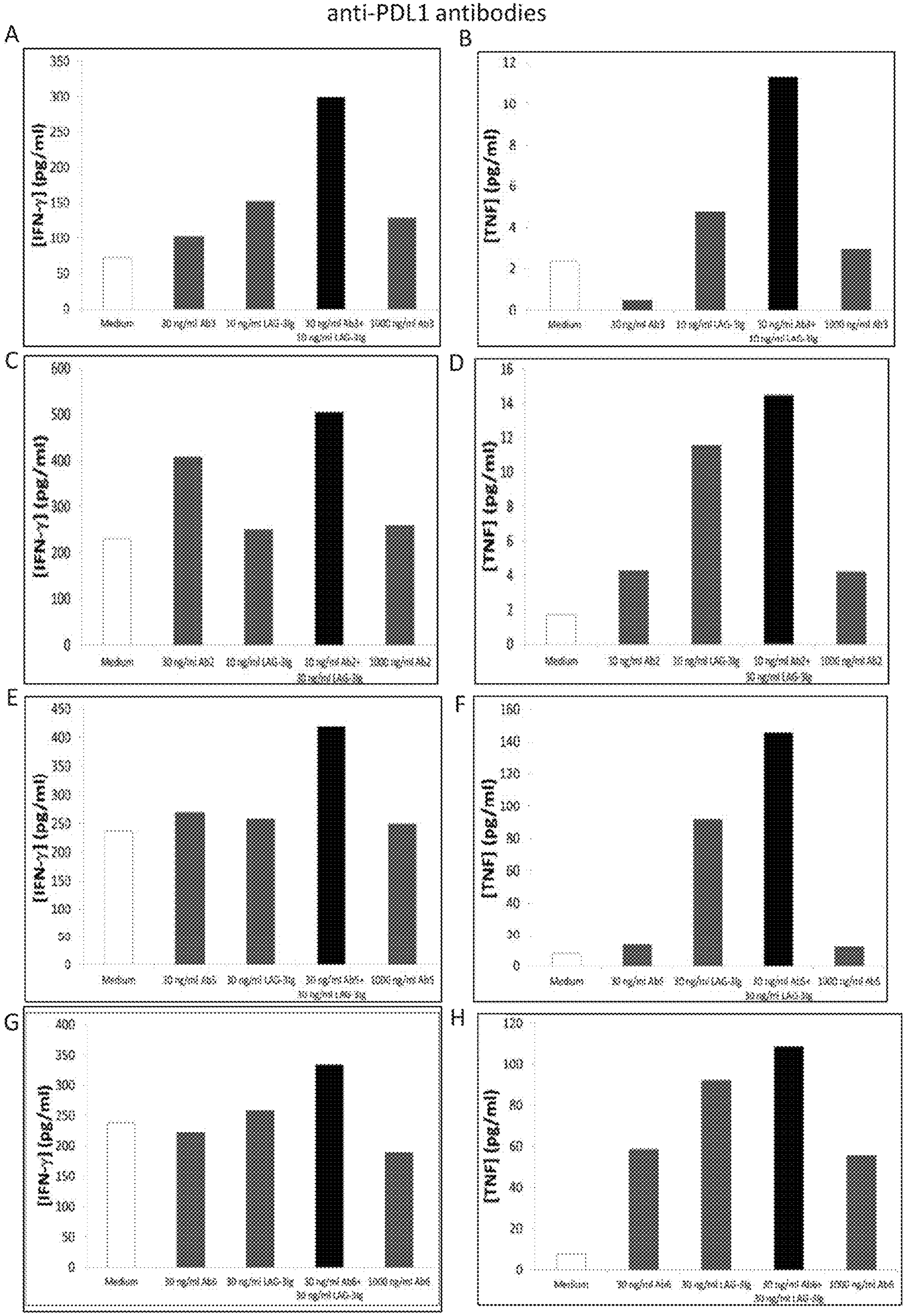
FIGS. 18A-18H. Show the effect of LAG-3Ig and different anti-PD-L1 antibodies (Ab3, Ab4, Ab5, and Ab6) on the secretion of IFN-γ and TNF-α induced by antigenic stimulation. (A) Effect of Ab3 on IFN-γ; (B) Effect of Ab3 on TNF-α; (C) Effect of Ab4 on IFN-γ; (D) Effect of Ab4 on TNF-α. (E) Effect of Ab5 on IFN-γ; (F) Effect of Ab5 on TNF-α; (G) Effect of Ab6 on IFN-γ; (H) Effect of Ab6 on TNF-α.

The concentrations of IFN-γ and TNF-α in the pooled triplicates for each condition of stimulation for the anti-PD-L1 antibodies are recorded in Table 26. The results are plotted in FIG. 18.

TABLE 26

Secretion of IFN-γ and TNF-α induced by antigen in the presence of anti-PD-L1 antibody with and without LAG-3Ig

| Anti-PD-L1 antibody | Stimulation condition [Anti-PD-L1] (ng/ml) | [LAG-3Ig] (ng/ml) | Concentration (pg/ml) IFNγ | TNF-α | Increase in concentration (pg/ml) above background IFNγ | TNF-α |
|---|---|---|---|---|---|---|
| Ab3 | — | — | 72.9 | 2.3 | — | — |
| | 30 | — | 101.4 | 0.5 | 28.5 | −1.8 |
| | — | 10 | 152.0 | 4.7 | 79.1 | 2.4 |
| | 30 | 10 | 299.4 | 11.3 | 226.5 | 9.0 |
| | 1000 | | 128.4 | 2.9 | 55.5 | 0.6 |
| Ab4 | — | — | 50.06 | 5.57 | — | — |
| | 30 | — | 52.37 | 7.65 | 2.31 | 2.08 |
| | | 10 | 58.06 | 64.28 | 8.00 | 58.71 |
| | 30 | 10 | 176.09 | 85.91 | 126.03 | 80.34 |
| | 1000 | | 39.40 | 8.07 | −10.66 | 2.50 |
| Ab5 | — | — | 238.21 | 7.70 | — | — |
| | 30 | — | 268.32 | 13.23 | 30.11 | 5.53 |
| | — | 30 | 258.05 | 91.94 | 19.84 | 84.21 |
| | 30 | 30 | 418.55 | 145.54 | 180.34 | 137.84 |
| | 1000 | | 249.10 | 11.70 | 10.89 | 4.00 |
| Ab6 | — | — | 238.21 | 7.70 | — | — |
| | 30 | — | 221.70 | 58.47 | −16.51 | 50.77 |
| | | 30 | 258.05 | 91.94 | 19.84 | 84.24 |
| | 30 | 30 | 333.35 | 108.69 | 95.14 | 100.99 |
| | 1000 | | 188.60 | 55.51 | -49.61 | 47.81 |

The results show that, for each anti-PD-L1 antibody, secretion of IFN-γ was increased when the PBMCs were incubated in the presence of LAG-3Ig and lower concentrations of anti-PD-L1 antibody, compared with anti-PD-L1 antibody alone. For example, the increase in concentration of IFN-γ above the background level (i.e. the concentration of IFN-γ in the absence of anti-PD-L1 and LAG-3Ig) in the presence of 10 or 30 ng/ml LAG-3Ig and 30 ng/ml anti-PD-L1 antibody, was greater than the sum of the corresponding increase in the presence of 10 or 30 ng/ml LAG-3Ig alone and 30 ng/ml anti-PD-L1 antibody alone (i.e. for Ab3, 226.5>28.5+79.1; for Ab4, 126.03>2.31+8.00; for Ab5, 180.34>19.84+30.11; for Ab6, 95.14>−16.51+19.84). The effect of the combination of LAG-3Ig and each different anti-PD-L1 antibody was, therefore, synergistic.

The results also show that secretion of IFN-γ induced by a combination of LAG-3Ig and a relatively low concentration of anti-PD-L1 antibody (30 ng/ml) was dramatically higher than secretion of IFN-γ induced by a much higher concentration (1000 ng/ml, over 30 times higher) of anti-PD-L1 antibody alone (i.e. for Ab3, 226.5>55.5; for Ab4, 126.03>−10.66; for Ab5, 180.34>10.89; for Ab6 95.14>−49.61).

Regarding TNF-α secretion, for anti-PD-L1 antibodies Ab3, Ab4, and Ab5, secretion of TNF-α was increased when the PBMCs were incubated in the presence of LAG-3Ig and lower concentrations of anti-PD-L1 antibody, compared with anti-PD-L1 antibody alone. For example, the increase in concentration of TNF-α above the background level (i.e. the concentration of TNF-α in the absence of anti-PD-L1 and LAG-3Ig) in the presence of 10 or 30 ng/ml LAG-3Ig and 30 ng/ml Ab3, Ab4, or Ab5 anti-PD-L1 antibody was greater than the sum of the corresponding increase in the presence of LAG-3Ig alone and 30 ng/ml Ab3, Ab4, or Ab5 anti-PD-L1 antibody alone (i.e. for Ab3, 9.0>−1.8+2.4; for Ab4, 80.34>2.08+58.71; for Ab5, 137.84>5.53+84.21). The effect of the combination of LAG-3Ig and these different anti-PD-L1 antibodies was, therefore, synergistic.

Although no synergistic effect on TNF-α secretion was observed for anti-PD-L1 antibody Ab6 in combination with LAG-3Ig, this may be due to the high level of TNF-α secretion in the presence of this antibody alone. Nevertheless, the level of TNF-α secretion in the presence of the combination of Ab6 and LAG-3Ig was higher than in the presence of Ab6 antibody alone (at 30 ng/ml and at 1000 ng/ml).

The results also show that secretion of TNF-α induced by a combination of LAG-3Ig and a relatively low concentration of anti-PD-L1 antibody (30 ng/ml) was dramatically higher than secretion of TNF induced by a much higher concentration (1000 ng/ml, over 30 times higher) of anti-PD-L1 antibody alone (i.e. for Ab3, 9.0>0.6; for Ab4, 80.34>2.50; for Ab5, 137.84>4.00; for Ab6 100.99>47.81).

It was concluded from these results that in vitro T cell response (as measured by IFN-γ and TNF secretion) induced by relatively low doses of anti-PD-L1 antibody is synergistically increased by a soluble LAG-3 derivative. It was also concluded that a significantly greater in vitro T cell response is obtained using over 30 times less anti-PD-L1 antibody if this is combined with a soluble LAG-3 derivative. These effects were seen with different anti-PD-L1 antibodies.

Example 13

Effect of LAG-3 Derivatives and Anti-PD-1 Antibody on IFN-γ Production Induced by Antigenic Stimulation This example demonstrates the effect of various different soluble derivatives of LAG-3 (derivatives (i), (ii), and (iv) described in Example 5 and illustrated in FIG. 7) and anti-PD-1 antibody on T-cell activation in vitro using an IFN-γ secretion assay.

PBMCs from healthy donors ($0.2\times10^6$ cells/wells at 1M/ml in complete RPMI+10% FBS) were incubated with a pool of peptides covering the sequence of CMV pp35 in triplicate, without any additive (Medium), with 30 ng/ml or 1000 ng/ml of anti-PD-1 antibody (EH12 clone), with 30 ng/ml LAG-3 derivative (IMP321, IMP321 R75A, or LAG3 D1D4-linker2-Ig), or with 30 ng/ml of LAG-3 derivative and 30 ng/ml of anti-PD-1.

The T cell response was evaluated by measuring the concentration of IFN-γ in cell culture supernatant three days post stimulation using BD Cytometric Bead Array.

Figure 19:
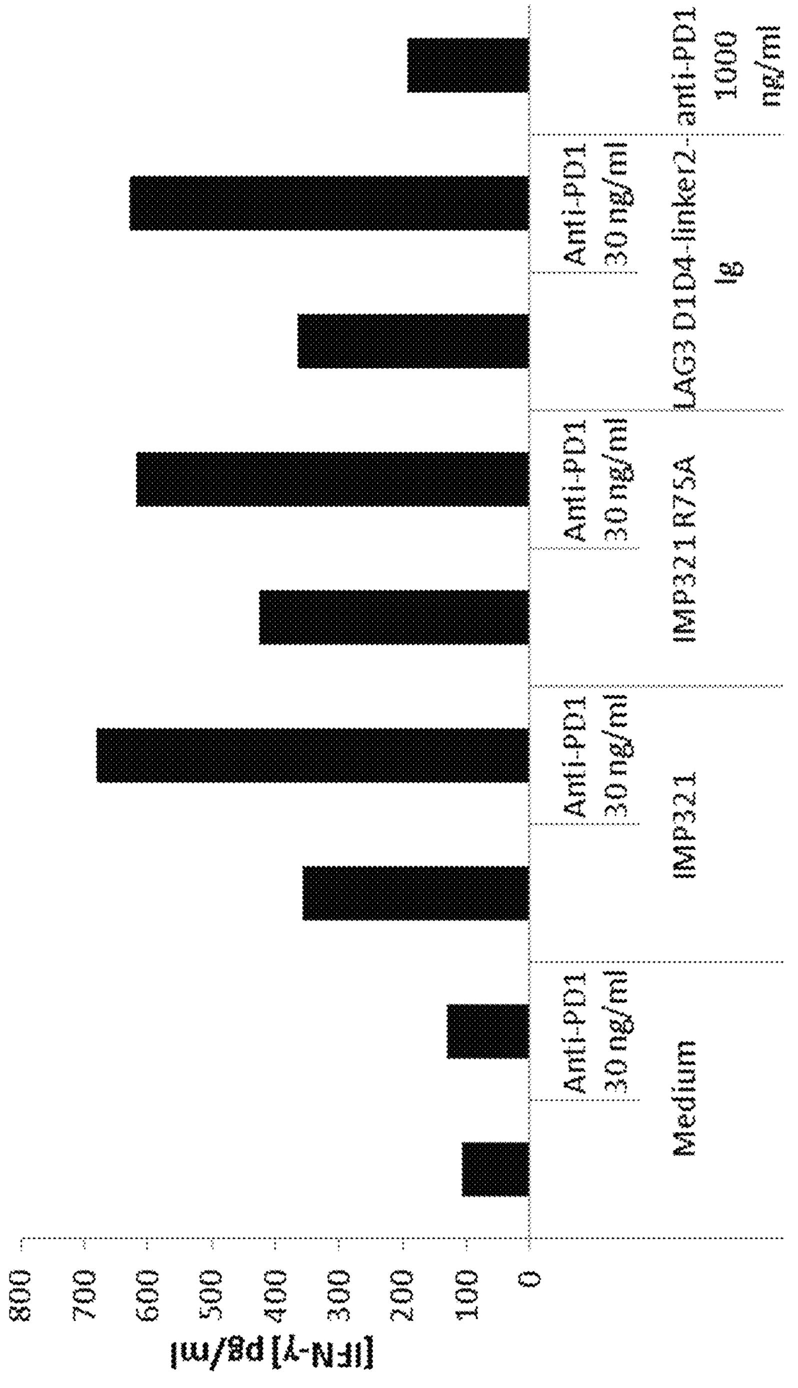
FIG. 19. Shows the effect of different LAG-3 derivatives (IMP321, IMP321 R75A, LAG3 D1D4-linker2-Ig) and anti-PD-1 antibody on the secretion of IFN-γ induced by antigenic stimulation.

The concentration of IFN-γ in the pooled triplicates for each condition of stimulation is recorded in Table 27. The results are plotted in FIG. 19.

TABLE 27

Secretion of IFN-γ induced by antigen in the presence of anti-PD-1 antibody with and without different derivatives of LAG-3

| Stimulation condition | | IFNγ | Increase in [IFNγ] |
|---|---|---|---|
| [Anti-PD-1] (ng/ml) | LAG-3 derivative (30 ng/ml) | Concentration (pg/ml) | (pg/ml) above background |
| — | — | 107.5 | — |
| 30 | — | 129.8 | 22.3 |
| — | IMP321 | 357.2 | 249.7 |
| 30 | IMP321 | 679.8 | 572.3 |
| — | IMP321 R75A | 424.8 | 317.3 |
| 30 | IMP321 R75A | 618.7 | 511.2 |
| — | LAG3 D1D4-linker2-Ig | 365.5 | 258.0 |
| 30 | LAG3 D1D4-linker2-Ig | 628.2 | 520.7 |
| 1000 | — | 193.4 | 85.9 |

The results show that for each LAG-3 derivative, secretion of IFN-γ was increased when the PBMCs were incubated in the presence of 30 ng/ml LAG-3 derivative and 30 ng/ml anti-PD-1 antibody, compared with 30 ng/ml LAG-3 derivative or 30 ng/ml anti-PD-1 antibody alone. For example, the increase in concentration of IFN-γ above the background level (i.e. the concentration of IFN-γ in the absence of anti-PD-1 and LAG-3 derivative) in the presence of 30 ng/ml LAG-3 derivative and 30 ng/ml anti-PD-1 antibody, was greater than the sum of the corresponding increase in the presence of 30 ng/ml LAG-3 derivative alone and 30 ng/ml anti-PD-1 antibody alone (i.e. for IMP321, 572.3>249.7+22.3; for IMP321 R75A, 511.2>317.3+22.3; for LAG3 D1D4-linker2-Ig, 520.7>258.0+22.3). The effect of the combination of anti-PD-1 antibody and each different LAG-3 derivative was, therefore, synergistic.

The results also show that secretion of IFN-γ induced by a combination of each LAG-3 derivative and a relatively low concentration of anti-PD-1 antibody (30 ng/ml) was dramatically higher than secretion of IFN-γ induced by a much higher concentration (1000 ng/ml, over 30 times higher) of anti-PD-1 antibody alone (i.e. for IMP321, 572.3>85.9; for IMP321 R75A, 511.2>85.9; for LAG3 D1D4-linker2-Ig, 520.7>85.9).

It was concluded from these results that in vitro T cell response (as measured by IFN-γ secretion) induced by relatively low doses of anti-PD-1 antibody is synergistically increased by various different soluble LAG-3 derivatives, each of which retains ability to bind MHC class II-positive cells. It was also concluded that a significantly greater in vitro T cell response is obtained using over 30 times less anti-PD-1 antibody if this is combined with any of the soluble LAG-3 derivatives.

The invention claimed is:

1. A method of treating or ameliorating a cancer in a subject in need thereof, the method comprising administering to the subject an effective amount of:

a human LAG-3 protein, or a derivative thereof which is a soluble fragment, variant, or mutant of human LAG-3 protein that is able to bind to MHC class II molecules, wherein the derivative comprises domain D1 and domain D2 of human LAG3 protein, and wherein the derivative is fused to an Immunoglobulin Fc sequence; and a programmed cell death protein-1 (PD-1) pathway inhibitor, wherein the PD-1 pathway inhibitor is (i) an anti-PD-1 antibody, or a fragment thereof that retains ability to inhibit binding of PD-1 to PD-L1 and/or PD-L2; or (ii) an anti-PD-L1 antibody, or a fragment thereof that retains ability to inhibit binding of PD-L1 to PD-1;

wherein the LAG-3 protein or the derivative of LAG-3 protein binds to MHC class II molecules on antigen-presenting cells (APCs), thereby activating APCs and further activating T cells.

2. The method according to claim 1, wherein the LAG-3 protein, or derivative thereof, and the PD-1 pathway inhibitor are administered sequentially or co-administered to the subject.

3. The method according to claim 2, wherein the LAG-3 protein, or derivative thereof, and the PD-1 pathway inhibitor are administered to the subject within 96 hours of each other.

4. The method according to claim 1, wherein the LAG-3 protein, or derivative thereof, is administered after the PD-1 pathway inhibitor.

5. The method according to claim 1, wherein the LAG-3 protein, or derivative thereof, is administered to the subject at a dose which is a molar equivalent of 0.25-30 mg of LAG-3Ig fusion protein IMP321.

6. The method according to claim 1, wherein a plurality of doses of the LAG-3 protein, or derivative thereof, is administered to the subject and/or a plurality of doses of the PD-1 pathway inhibitor is administered to the subject.

7. The method according to claim 6, wherein a dose of the LAG-3 protein, or derivative thereof, is administered before, with, or after each administration of two or more doses of the PD-1 pathway inhibitor.

8. The method according to claim 1, wherein the PD-1 pathway inhibitor is pembrolizumab or nivolumab or pidilizumab.

9. The method according to claim 1, wherein the PD-1 pathway inhibitor is BMS-936559, MEDI4736, MPDL3280A, or MSB0010718C.

10. The method according to claim 1, wherein the LAG-3 protein or derivative thereof, and the PD-1 pathway inhibitor, are administered in any of the combinations of dosage amounts shown in the Table below:

| Type of PD-1 pathway inhibitor | Dose of PD-1 pathway inhibitor: mg/kg [mg dose for 70 kg human] | Human dose of LAG-3 protein or derivative thereof (given as a mg dose of IMP321, or a molar equivalent thereof) |
|---|---|---|
| Pembrolizumab | 0.001-5 mg/kg [0.07-350 mg] | 0.25-30 mg |
| | 0.001-2.5 mg/kg [0.07-175 mg] | 0.25-30 mg |
| | 0.001-1 mg/kg [0.07-70 mg] | 0.25-30 mg |
| | 0.001-<1 mg/kg [0.07-<70 mg] | 0.25-30 mg |
| | 0.001-0.5 mg/kg [0.07-35 mg] | 0.25-30 mg |
| | 0.001-0.1 mg/kg [0.07-7 mg] | 0.25-30 mg |
| | 0.002-5 mg/kg [0.14-350 mg] | 0.25-30 mg |
| | 0.002-2.5 mg/kg [0.14-175 mg] | 0.25-30 mg |

-continued

| Type of PD-1 pathway inhibitor | Dose of PD-1 pathway inhibitor: mg/kg [mg dose for 70 kg human] | Human dose of LAG-3 protein or derivative thereof (given as a mg dose of IMP321, or a molar equivalent thereof) |
|---|---|---|
| | 0.002-1 mg/kg [0.14-70 mg] | 0.25-30 mg |
| | 0.002-<1 mg/kg [0.14-<70 mg] | 0.25-30 mg |
| | 0.002-0.5 mg/kg [0.14-35 mg] | 0.25-30 mg |
| | 0.002-0.1 mg/kg [0.14-7 mg] | 0.25-30 mg |
| Pembrolizumab | 0.001-5 mg/kg [0.07-350 mg] | 1-30 mg |
| | 0.001-2.5 mg/kg [0.07-175 mg] | 1-30 mg |
| | 0.001-1 mg/kg [0.07-70 mg] | 1-30 mg |
| | 0.001-<1 mg/kg [0.07-<70 mg] | 1-30 mg |
| | 0.001-0.5 mg/kg [0.07-35 mg] | 1-30 mg |
| | 0.001-0.1 mg/kg [0.07-7 mg] | 1-30 mg |
| | 0.002-5 mg/kg [0.14-350 mg] | 1-30 mg |
| | 0.002-2.5 mg/kg [0.14-175 mg] | 1-30 mg |
| | 0.002-1 mg/kg [0.14-70 mg] | 1-30 mg |
| | 0.002-1 mg/kg [0.14-70 mg] | 1-30 mg |
| | 0.002-<1 mg/kg [0.14-<70 mg] | 1-30 mg |
| | 0.002-0.5 mg/kg [0.14-35 mg] | 1-30 mg |
| Pembrolizumab | 0.001-5 mg/kg [0.07-350 mg] | 6-30 mg |
| | 0.001-2.5 mg/kg [0.07-175 mg] | 6-30 mg |
| | 0.001-1 mg/kg [0.07-70 mg] | 6-30 mg |
| | 0.001-<1 mg/kg [0.07-<70 mg] | 6-30 mg |
| | 0.001-0.5 mg/kg [0.07-35 mg] | 6-30 mg |
| | 0.001-0.1 mg/kg [0.07-7 mg] | 6-30 mg |
| | 0.002-5 mg/kg [0.14-350 mg] | 6-30 mg |
| | 0.002-2.5 mg/kg [0.14-175 mg] | 6-30 mg |
| | 0.002-1 mg/kg [0.14-70 mg] | 6-30 mg |
| | 0.002-<1 mg/kg [0.14-<70 mg] | 6-30 mg |
| | 0.002-0.5 mg/kg [0.14-35 mg] | 6-30 mg |
| | 0.002-0.1 mg/kg [0.14-7 mg] | 6-30 mg |
| Nivolumab | 0.001-5 mg/kg [0.07-350 mg] | 0.25-30 mg |
| | 0.001-2.5 mg/kg [0.07-175 mg] | 0.25-30 mg |
| | 0.001-1 mg/kg [0.07-70 mg] | 0.25-30 mg |
| | 0.001-<1 mg/kg [0.07-<70 mg] | 0.25-30 mg |
| | 0.001-0.5 mg/kg [0.07-35 mg] | 0.25-30 mg |
| | 0.001-0.1 mg/kg [0.07-7 mg] | 0.25-30 mg |
| | 0.002-5 mg/kg [0.14-350 mg] | 0.25-30 mg |
| | 0.002-2.5 mg/kg [0.14-175 mg] | 0.25-30 mg |
| | 0.002-1 mg/kg [0.14-70 mg] | 0.25-30 mg |
| | 0.002-<1 mg/kg [0.14-<70 mg] | 0.25-30 mg |
| | 0.002-0.5 mg/kg [0.14-35 mg] | 0.25-30 mg |
| | 0.002-0.1 mg/kg [0.14-7 mg] | 0.25-30 mg |
| Nivolumab | 0.001-5 mg/kg [0.07-350 mg] | 1-30 mg |
| | 0.001-2.5 mg/kg [0.07-175 mg] | 1-30 mg |
| | 0.001-1 mg/kg [0.07-70 mg] | 1-30 mg |
| | 0.001-<1 mg/kg [0.07-<70 mg] | 1-30 mg |
| | 0.001-0.5 mg/kg [0.07-35 mg] | 1-30 mg |
| | 0.001-0.1 mg/kg [0.07-7 mg] | 1-30 mg |
| | 0.002-5 mg/kg [0.14-350 mg] | 1-30 mg |
| | 0.002-2.5 mg/kg [0.14-175 mg] | 1-30 mg |
| | 0.002-1 mg/kg [0.14-70 mg] | 1-30 mg |
| | 0.002-<1 mg/kg [0.14-<70 mg] | 1-30 mg |
| | 0.002-0.5 mg/kg [0.14-35 mg] | 1-30 mg |
| | 0.002-0.1 mg/kg [0.14-7 mg] | 1-30 mg |
| Nivolumab | 0.001-5 mg/kg [0.07-350 mg] | 6-30 mg |
| | 0.001-2.5 mg/kg [0.07-175 mg] | 6-30 mg |
| | 0.001-1 mg/kg [0.07-70 mg] | 6-30 mg |
| | 0.001-<1 mg/kg [0.07-<70 mg] | 6-30 mg |
| | 0.001-0.5 mg/kg [0.07-35 mg] | 6-30 mg |
| | 0.001-0.1 mg/kg [0.07-7 mg] | 6-30 mg |
| | 0.002-5 mg/kg [0.14-350 mg] | 6-30 mg |
| | 0.002-2.5 mg/kg [0.14-175 mg] | 6-30 mg |
| | 0.002-1 mg/kg [0.14-70 mg] | 6-30 mg |
| | 0.002-<1 mg/kg [0.14-<70 mg] | 6-30 mg |
| | 0.002-0.5 mg/kg [0.14-35 mg] | 6-30 mg |
| | 0.002-0.1 mg/kg [0.14-7 mg] | 6-30 mg. |

11. The method according to claim 1, wherein the derivative of LAG-3 protein comprises domains D1, D2, D3, and optionally D4, of human LAG-3 protein.

12. The method according to claim 1, wherein the derivative of LAG-3 protein is the recombinant soluble human LAG-3Ig fusion protein IMP321.

13. The method according to claim 1, wherein the cancer is a PD-L1-positive or a PD-L2-positive cancer.

14. The method according to claim 1, wherein the cancer is skin, lung, ovarian, renal, colon, colorectal, breast, gastric, esophageal, pancreatic, bladder, urothelial, or liver cancer, or a melanoma a prostate cancer, a head and neck cancer, a cervical cancer, a thyroid cancer, a glioblastoma, a glioma, leukemia, a lymphoma, an adrenal gland cancer, an AIDS-associated cancer, an alveolar soft part sarcoma, an astrocytic tumor, bone cancer, a brain and spinal cord cancer, a metastatic brain tumor, a carotid body tumor, a chondrosarcoma, a chordoma, a chromophobe renal cell carcinoma, a clear cell carcinoma, cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gestational trophoblastic disease, a germ cell tumor, a haematological malignancy, hepatocellular carcinoma, an islet cell tumor, a Kaposi's sarcoma, a kidney cancer, a lipoma/benign lipomatous tumor, a liposarcoma/malignant lipomatous tumor, a medulloblastoma, a meningioma, a Merkel cell carcinoma, a multiple endocrine neoplasia, a multiple myeloma, a myelodysplasia syndrome, a neuroblastoma, a neuroendocrine tumor, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a soft-tissue sarcoma, a squamous cell cancer, a stomach cancer, a synovial sarcoma, a testicular cancer, a thymic carcinoma, a thymoma, a thyroid metastatic cancer, or a uterine cancer.

15. The method of claim 14, wherein (i) the lung cancer is squamous or nonsquamous non-small-cell lung carcinoma (NSCLC), (ii) the melanoma is metastatic malignant melanoma;

(iii) the prostate cancer is hormone refractory prostate adenocarcinoma;

(iv) the head and neck cancer is squamous cell carcinoma of the head and neck; or (v) the lymphoma is a B cell lymphoma.

* * * * *

SEQUENCE LISTING

```
Sequence total quantity: 2
SEQ ID NO: 1           moltype = AA  length = 502
FEATURE                Location/Qualifiers
source                 1..502
                       mol_type = protein
                       organism = Homo sapiens
SEQUENCE: 1
LQPGAEVPVV WAQEGAPAQL PCSPTIPLQD LSLLRRAGVT WQHQPDSGPP AAAPGHPLAP  60
GPHPAAPSSW GPRPRRYTVL SVGPGGLRSG RLPLQPRVQL DERGRQRGDF SLWLRPARRA  120
DAGEYRAAVH LRDRALSCRL RLRLGQASMT ASPPGSLRAS DWVILNCSFS RPDRPASVHW  180
FRNRGQGRVP VRESPHHHLA ESFLFLPQVS PMDSGPWGCI LTYRDGFNVS IMYNLTVLGL  240
EPPTPLTVYA GAGSRVGLPC RLPAGVGTRS FLTAKWTPPG GGPDLLVTGD NGDFTLRLED  300
VSQAQAGTYT CHIHLQEQQL NATVTLAIIT VTPKSFGSPG SLGKLLCEVT PVSGQERFVW  360
SSLDTPSQRS FSGPWLEAQE AQLLSQPWQC QLYQGERLLG AAVYFTELSS PGAQRSGRAP  420
GALPAGHLLL FLTLGVLSLL LLVTGAFGFH LWRRQWRPRR FSALEQGIHP QAQSKIEELE  480
QEPEPEPEPE PEPEPEPEPE QL                                            502

SEQ ID NO: 2           moltype = AA  length = 30
FEATURE                Location/Qualifiers
source                 1..30
                       mol_type = protein
                       organism = Homo sapiens
SEQUENCE: 2
GPPAAAPGHP LAPGPHPAAP SSWGPRPRRY                                    30
```